US009895385B2

(12) United States Patent
Eagle et al.

(10) Patent No.: US 9,895,385 B2
(45) Date of Patent: Feb. 20, 2018

(54) METHODS FOR TREATING PULMONARY NON-TUBERCULOUS MYCOBACTERIAL INFECTIONS

(71) Applicant: Insmed Incorporated, Bridgewater, NJ (US)

(72) Inventors: Gina Eagle, Morristown, NJ (US); Renu Gupta, Moorestown, NJ (US)

(73) Assignee: INSMED INCORPORATED, Bridgewater, NJ (US)

( * ) Notice: Subject to any disclaimer, the term of this patent is extended or adjusted under 35 U.S.C. 154(b) by 0 days.

(21) Appl. No.: 14/713,926

(22) Filed: May 15, 2015

(65) Prior Publication Data

US 2015/0328244 A1 Nov. 19, 2015

Related U.S. Application Data

(60) Provisional application No. 61/993,439, filed on May 15, 2014, provisional application No. 62/042,126, filed on Aug. 26, 2014, provisional application No. 62/048,068, filed on Sep. 9, 2014, provisional application No. 62/056,296, filed on Sep. 26, 2014.

(51) Int. Cl.
*A61K 31/7036* (2006.01)
*A61K 9/00* (2006.01)
*A61K 45/06* (2006.01)
*A61K 9/127* (2006.01)

(52) U.S. Cl.
CPC ........ *A61K 31/7036* (2013.01); *A61K 9/0078* (2013.01); *A61K 9/127* (2013.01); *A61K 45/06* (2013.01)

(58) Field of Classification Search
None
See application file for complete search history.

(56) References Cited

U.S. PATENT DOCUMENTS

| | | |
|---|---|---|
| 3,091,572 A | 5/1963 | Luedemann et al. |
| 3,136,704 A | 6/1964 | Chamey |
| 4,235,871 A | 11/1980 | Paphadjopoulos et al. |
| 4,372,949 A | 2/1983 | Kodama et al. |
| 4,394,448 A | 7/1983 | Szoka, Jr. et al. |
| 4,396,630 A | 8/1983 | Riedl et al. |
| 4,451,447 A | 5/1984 | Kaplan et al. |
| 4,515,736 A | 5/1985 | Deamer |
| 4,522,803 A | 6/1985 | Lenk et al. |
| 4,547,490 A | 10/1985 | Ecanow et al. |
| 4,588,578 A | 5/1986 | Fountain et al. |
| 4,606,939 A | 8/1986 | Frank et al. |
| 4,684,625 A | 8/1987 | Eppstein et al. |
| 4,693,999 A | 9/1987 | Axelsson et al. |
| 4,721,612 A | 1/1988 | Janoff et al. |
| 4,767,874 A | 8/1988 | Shima et al. |
| 4,833,134 A | 5/1989 | Kishimoto et al. |
| 4,857,311 A | 8/1989 | Domb et al. |
| 4,895,452 A | 1/1990 | Yioumas et al. |
| 4,895,719 A | 1/1990 | Radhakrishnan et al. |
| 4,897,384 A | 1/1990 | Janoff et al. |
| 4,933,121 A | 6/1990 | Law et al. |
| 4,952,405 A | 8/1990 | Yau-Young |
| 4,963,367 A | 10/1990 | Ecanow |
| 4,975,282 A | 12/1990 | Cullis et al. |
| 4,981,692 A | 1/1991 | Popescu et al. |
| 5,000,958 A | 3/1991 | Fountain et al. |
| 5,006,343 A | 4/1991 | Benson et al. |
| 5,008,050 A | 4/1991 | Cullis et al. |
| 5,023,087 A | 6/1991 | Yau-Young |
| 5,030,453 A | 7/1991 | Lenk et al. |
| 5,041,278 A | 8/1991 | Janoff et al. |
| 5,049,388 A | 9/1991 | Knight et al. |

(Continued)

FOREIGN PATENT DOCUMENTS

| | | |
|---|---|---|
| CA | 2215716 C | 12/1999 |
| CA | 2614764 | 1/2007 |

(Continued)

OTHER PUBLICATIONS

National Jewish Health; Third sputum smear teast negative fro XDR TB patient Andrew Speaker; https://www.nationaljewish.org/about/news/press-releases/2007/smear-test-3; Jun. 5, 2007.*
International Search Report and Written Opinion for International Application No. PCT/US2015/031079, dated Aug. 5, 2015, 8 pages.
British Thoracic Society Nebuliser Project Group, Thorax, 1997, vol. 52 (Suppl. 2), S1-S24.
International Search Report and Written Opinion for International Application No. PCT/US2008/062469, dated Sep. 18, 2008, 9 pages.
International Preliminary Report on Patentability for International Application No. PCT/US2008/062469, dated Nov. 10, 2009, 7 pages.
International Search Report and Written Opinion for International Application No. PCT/US2008/062868, dated Sep. 18, 2008, 7 pages.
International Preliminary Report on Patentability for International Application No. PCT/US2008/062868, dated Nov. 10, 2009, 5 pages.
Supplementary European Search Report for European Application No. 09821103.0, dated Aug. 12, 2015, 10 pages.
International Preliminary Report on Patentability for International Application No. PCT/US2009/060468, dated Apr. 19, 2011, 4 pages.

(Continued)

*Primary Examiner* — Celeste A Roney
(74) *Attorney, Agent, or Firm* — Cooley LLP

(57) ABSTRACT

Provided herein are methods for treating a pulmonary infection in a patient in need thereof, for example, a nontuberculous mycobacterial pulmonary infection for at least one treatment cycle. The method comprises administering to the lungs of the patient a pharmaceutical composition comprising a liposomal complexed aminoglycoside comprising a lipid component comprising electrically neutral lipids and an aminoglycoside. Administration comprises aerosolizing the pharmaceutical composition to provide an aerosolized pharmaceutical composition comprising a mixture of free aminoglycoside and liposomal complexed aminoglycoside, and administering the aerosolized pharmaceutical composition via a nebulizer to the lungs of the patient. The methods provided herein result in a change from baseline on the semi-quantitative scale for mycobacterial culture for a treated patient, and/or NTM culture conversion to negative during or after the administration period.

30 Claims, 9 Drawing Sheets

(56) References Cited

U.S. PATENT DOCUMENTS

| | | | |
|---|---|---|---|
| 5,049,389 A | 9/1991 | Radhakrishnan |
| 5,059,421 A | 10/1991 | Loughrey et al. |
| 5,059,591 A | 10/1991 | Janoff et al. |
| 5,077,056 A | 12/1991 | Bally et al. |
| 5,169,637 A | 12/1992 | Lenk et al. |
| 5,178,876 A | 1/1993 | Khokhar et al. |
| 5,192,549 A | 3/1993 | Barenolz et al. |
| 5,211,955 A | 5/1993 | Legros et al. |
| 5,252,339 A | 10/1993 | Cristofori et al. |
| 5,264,618 A | 11/1993 | Feigner et al. |
| 5,269,979 A | 12/1993 | Fountain |
| 5,279,833 A | 1/1994 | Rose |
| 5,316,771 A | 5/1994 | Barenholz et al. |
| 5,320,906 A | 6/1994 | Eley et al. |
| 5,334,761 A | 8/1994 | Gebeyehu et al. |
| 5,409,704 A | 4/1995 | Bally et al. |
| 5,459,127 A | 10/1995 | Feigner et al. |
| 5,508,269 A | 4/1996 | Smith et al. |
| 5,540,936 A | 7/1996 | Coe et al. |
| 5,543,152 A | 8/1996 | Webb et al. |
| 5,549,102 A | 8/1996 | Lintl et al. |
| 5,569,464 A | 10/1996 | Endo et al. |
| 5,578,320 A | 11/1996 | Janoff et al. |
| 5,596,982 A | 1/1997 | Blaha-Schnabel |
| 5,610,198 A | 3/1997 | Barry, III et al. |
| 5,614,216 A | 3/1997 | Janoff |
| 5,616,334 A | 4/1997 | Janoff et al. |
| 5,631,018 A | 5/1997 | Zalipsky et al. |
| 5,641,662 A | 6/1997 | Debs et al. |
| 5,643,599 A | 7/1997 | Lee et al. |
| 5,662,929 A | 9/1997 | Legace et al. |
| 5,665,383 A | 9/1997 | Grinstaff et al. |
| 5,723,147 A | 3/1998 | Kim et al. |
| 5,736,155 A | 4/1998 | Bally et al. |
| 5,740,966 A | 4/1998 | Blaha-Schnabel |
| 5,741,516 A | 4/1998 | Webb et al. |
| 5,753,613 A | 5/1998 | Ansell et al. |
| 5,756,120 A | 5/1998 | Hersch et al. |
| 5,756,121 A | 5/1998 | Bracken |
| 5,756,353 A | 5/1998 | Debs |
| 5,759,571 A | 6/1998 | Hersch et al. |
| 5,766,627 A | 6/1998 | Sankaram et al. |
| 5,785,987 A | 7/1998 | Hope et al. |
| 5,795,589 A | 8/1998 | Mayer et al. |
| 5,814,335 A | 9/1998 | Webb et al. |
| 5,820,848 A | 10/1998 | Boni et al. |
| 5,837,279 A | 11/1998 | Janoff et al. |
| 5,837,282 A | 11/1998 | Fenske et al. |
| 5,840,702 A | 11/1998 | Bedwell |
| 5,843,473 A | 12/1998 | Woodle et al. |
| 5,849,490 A | 12/1998 | Schonwetter et al. |
| 5,861,159 A | 1/1999 | Pardoll et al. |
| 5,871,710 A | 2/1999 | Bogdanov et al. |
| 5,875,776 A | 3/1999 | Vaghefi |
| 5,922,350 A | 7/1999 | Janoff et al. |
| 5,945,122 A | 8/1999 | Abra et al. |
| 5,957,389 A | 9/1999 | Wunderlich et al. |
| 5,958,449 A | 9/1999 | Hersch et al. |
| 5,965,549 A | 10/1999 | Purwar et al. |
| 5,972,379 A | 10/1999 | Guo et al. |
| 5,993,850 A | 11/1999 | Sankaram et al. |
| 6,000,394 A | 12/1999 | Blaha-Schnabel et al. |
| 6,045,828 A | 4/2000 | Bystrom et al. |
| 6,051,251 A | 4/2000 | Zalipsky et al. |
| 6,051,549 A | 4/2000 | Roberts et al. |
| 6,085,741 A | 7/2000 | Becker |
| 6,086,851 A | 7/2000 | Boni et al. |
| 6,090,407 A | 7/2000 | Knight et al. |
| 6,106,479 A | 8/2000 | Wunderlich et al. |
| 6,106,858 A | 8/2000 | Ye et al. |
| 6,124,273 A | 9/2000 | Drohan et al. |
| 6,147,060 A | 11/2000 | Zasloff et al. |
| 6,162,462 A | 12/2000 | Bolotin et al. |
| 6,176,237 B1 | 1/2001 | Wunderlich et al. |
| 6,211,162 B1 | 4/2001 | Dale et al. |
| 6,221,388 B1 | 4/2001 | Hersch et al. |
| 6,228,346 B1 | 5/2001 | Zhang et al. |
| 6,228,393 B1 | 5/2001 | DiCosmo et al. |
| 6,235,177 B1 | 5/2001 | Borland et al. |
| 6,274,175 B1 | 8/2001 | Gombotz et al. |
| 6,338,859 B1 | 1/2002 | Leroux et al. |
| 6,348,069 B1 | 2/2002 | Vacanti et al. |
| 6,352,996 B1 | 3/2002 | Cao et al. |
| 6,387,886 B1 * | 5/2002 | Montgomery ....... A61K 9/0073 514/34 |
| 6,419,901 B2 | 7/2002 | Placke et al. |
| 6,440,393 B1 | 8/2002 | Waldrep et al. |
| 6,443,898 B1 | 9/2002 | Unger et al. |
| 6,447,753 B2 | 9/2002 | Edwards et al. |
| 6,451,784 B1 | 9/2002 | Placke et al. |
| 6,458,373 B1 | 10/2002 | Lambert et al. |
| 6,468,532 B1 | 10/2002 | Hsei et al. |
| 6,475,779 B2 | 11/2002 | Mathiowitz et al. |
| 6,481,438 B1 | 11/2002 | Gallem et al. |
| 6,492,560 B2 | 12/2002 | Wilbur et al. |
| 6,497,901 B1 | 12/2002 | Royer |
| 6,509,323 B1 | 1/2003 | Davis et al. |
| 6,511,676 B1 | 1/2003 | Boulikas |
| 6,513,727 B1 | 2/2003 | Jaser et al. |
| 6,521,211 B1 | 2/2003 | Unger et al. |
| 6,521,736 B2 | 2/2003 | Watterson et al. |
| 6,546,927 B2 | 4/2003 | Litherland et al. |
| 6,554,201 B2 | 4/2003 | Klimowicz et al. |
| 6,596,305 B1 | 7/2003 | Edgerly-Plug |
| 6,599,912 B1 | 7/2003 | Au et al. |
| 6,606,990 B2 | 8/2003 | Stapleton et al. |
| 6,613,352 B2 | 9/2003 | Lagace et al. |
| 6,615,824 B2 | 9/2003 | Power |
| 6,629,646 B1 | 10/2003 | Ivri |
| 6,676,034 B2 | 1/2004 | Tanaka et al. |
| 6,679,251 B1 | 1/2004 | Gallem et al. |
| 6,843,942 B2 | 1/2005 | Katinger et al. |
| 6,845,770 B2 | 1/2005 | Klimowicz et al. |
| 6,855,296 B1 | 2/2005 | Baker et al. |
| 6,900,184 B2 | 5/2005 | Cohen et al. |
| 6,915,962 B2 | 7/2005 | Power et al. |
| 6,916,490 B1 | 7/2005 | Garver et al. |
| 6,948,491 B2 | 9/2005 | Loeffler et al. |
| 6,962,151 B1 | 11/2005 | Knoch et al. |
| 6,983,747 B2 | 1/2006 | Gallem et al. |
| 6,991,809 B2 | 1/2006 | Anderson |
| 7,059,320 B2 | 6/2006 | Feiner et al. |
| 7,063,860 B2 | 6/2006 | Chancellor et al. |
| 7,077,126 B2 | 7/2006 | Kummer et al. |
| 7,100,600 B2 | 9/2006 | Loeffler et al. |
| 7,104,463 B2 | 9/2006 | Litherland et al. |
| 7,131,440 B2 | 11/2006 | Sonntag |
| 7,252,085 B2 | 8/2007 | Kunschir |
| 7,255,106 B2 | 8/2007 | Gallem et al. |
| 7,297,344 B1 | 11/2007 | Fleischer et al. |
| 7,331,339 B2 | 2/2008 | Smith et al. |
| 7,368,102 B2 | 5/2008 | Tarara et al. |
| D583,928 S | 12/2008 | Knoch |
| 7,458,372 B2 | 12/2008 | Feiner et al. |
| 7,472,701 B2 | 1/2009 | Pfichner et al. |
| 7,544,369 B2 | 6/2009 | Boni et al. |
| 7,600,511 B2 | 10/2009 | Power et al. |
| 7,686,014 B2 | 3/2010 | Boehm et al. |
| 7,718,189 B2 | 5/2010 | Boni et al. |
| 7,748,377 B2 | 7/2010 | Smith et al. |
| 7,758,886 B2 | 7/2010 | Jauernig et al. |
| 7,771,642 B2 | 8/2010 | Power et al. |
| 7,779,838 B2 | 8/2010 | Hetzer et al. |
| 7,879,351 B2 | 2/2011 | Li et al. |
| 7,891,352 B2 | 2/2011 | Gallem et al. |
| 7,931,212 B2 | 4/2011 | Urich et al. |
| D638,117 S | 5/2011 | Eckstein et al. |
| 7,958,887 B2 | 6/2011 | Kelliher et al. |
| 7,971,588 B2 | 7/2011 | Fink et al. |
| 7,980,247 B2 | 7/2011 | Boehm et al. |
| 8,006,698 B2 | 8/2011 | Boehm et al. |
| D652,908 S | 1/2012 | Eckstein et al. |
| 8,100,162 B2 | 1/2012 | Joern et al. |
| 8,113,194 B2 | 2/2012 | Boehm et al. |

(56) References Cited

U.S. PATENT DOCUMENTS

| | | | |
|---|---|---|---|
| D656,604 S | 3/2012 | Eckstein et al. |
| 8,226,975 B2 | 7/2012 | Weers |
| 8,263,645 B2 | 9/2012 | Keller |
| 8,333,187 B2 | 12/2012 | Gallem et al. |
| 8,342,171 B2 | 1/2013 | Boehm et al. |
| 8,347,878 B2 | 1/2013 | Schuschnig et al. |
| 8,387,895 B2 | 3/2013 | Stangl |
| 8,398,001 B2 | 3/2013 | Borland et al. |
| D680,214 S | 4/2013 | Eckstein et al. |
| 8,459,252 B2 | 6/2013 | Gallem et al. |
| 8,511,581 B2 | 8/2013 | Urich et al. |
| 8,596,264 B2 | 12/2013 | Sommer |
| 8,616,195 B2 | 12/2013 | Power et al. |
| 8,632,804 B2 | 1/2014 | Weers |
| 8,642,075 B2 | 2/2014 | Weers |
| 8,671,933 B2 | 3/2014 | Boehm et al. |
| 8,673,348 B2 | 3/2014 | Weers |
| 8,673,349 B2 | 3/2014 | Weers |
| 8,679,532 B2 | 3/2014 | Wears |
| 8,720,432 B2 | 5/2014 | Borgschulte et al. |
| 8,720,435 B2 | 5/2014 | Gallem et al. |
| 8,739,777 B2 | 6/2014 | Kreutzmann et al. |
| 8,802,137 B2 | 8/2014 | Boni et al. |
| 8,852,557 B2 | 10/2014 | Keller et al. |
| 8,985,100 B2 | 3/2015 | Minocchieri et al. |
| 9,016,272 B2 | 4/2015 | Gallem et al. |
| 9,027,548 B2 | 5/2015 | Borgschulte et al. |
| 9,046,092 B2 | 6/2015 | Boehm et al. |
| 9,061,303 B2 | 6/2015 | Waldner et al. |
| 9,072,464 B2 | 7/2015 | Haartsen et al. |
| 9,084,862 B2 | 7/2015 | Blakey et al. |
| 9,095,676 B2 | 8/2015 | Gallem et al. |
| 9,108,211 B2 | 8/2015 | Ivri |
| 9,114,081 B2 | 8/2015 | Gupta |
| 9,119,783 B2 | 9/2015 | Gupta |
| 9,119,930 B2 | 9/2015 | Kreutzmann et al. |
| 9,149,588 B2 | 10/2015 | Gordon et al. |
| 9,161,963 B2 | 10/2015 | Keller et al. |
| 9,168,556 B2 | 10/2015 | Pumm et al. |
| 9,198,859 B2 | 12/2015 | Keller et al. |
| 9,265,900 B2 | 2/2016 | Loenner et al. |
| 9,333,214 B2 | 5/2016 | Gupta |
| 9,402,845 B2 | 8/2016 | Weers |
| 9,511,082 B2 | 12/2016 | Weers |
| 9,549,925 B2 | 1/2017 | Weers |
| 9,549,939 B2 | 1/2017 | Weers |
| 2001/0006660 A1 | 7/2001 | Legace et al. |
| 2002/0035061 A1 | 3/2002 | Krieger et al. |
| 2002/0052390 A1 | 5/2002 | Ponikau |
| 2002/0086852 A1 | 7/2002 | Cantor et al. |
| 2002/0187105 A1 | 12/2002 | Zou et al. |
| 2003/0039615 A1* | 2/2003 | Katz ............... A61K 9/0073 424/46 |
| 2003/0059375 A1 | 3/2003 | Perez-Soler et al. |
| 2003/0096774 A1 | 5/2003 | Gonda et al. |
| 2003/0099697 A1 | 5/2003 | Panzner et al. |
| 2003/0118636 A1 | 6/2003 | Friesen et al. |
| 2003/0138481 A1 | 7/2003 | Zadi |
| 2003/0148964 A1* | 8/2003 | Dunne ............... A61K 31/7052 514/28 |
| 2003/0224039 A1 | 12/2003 | Boni et al. |
| 2004/0009126 A1 | 1/2004 | Pilkiewicz et al. |
| 2004/0032037 A1 | 2/2004 | Katinger et al. |
| 2004/0101553 A1 | 5/2004 | Lee et al. |
| 2004/0142025 A1 | 7/2004 | MacLachlan et al. |
| 2004/0142026 A1 | 7/2004 | Boni et al. |
| 2004/0180082 A1 | 9/2004 | Kang et al. |
| 2005/0019926 A1 | 1/2005 | Gonda et al. |
| 2005/0025822 A1 | 2/2005 | Wong et al. |
| 2005/0042341 A1 | 2/2005 | Thomas et al. |
| 2005/0113337 A1 | 5/2005 | Taneja et al. |
| 2005/0214224 A1 | 9/2005 | Weers et al. |
| 2005/0217666 A1 | 10/2005 | Fink et al. |
| 2005/0220752 A1 | 10/2005 | Charmot et al. |
| 2005/0249795 A1 | 11/2005 | Zhang et al. |
| 2006/0062738 A1 | 3/2006 | Hofmann et al. |
| 2006/0067998 A1 | 3/2006 | Kurzrock et al. |
| 2006/0073198 A1 | 4/2006 | Boni et al. |
| 2006/0217603 A1 | 9/2006 | Nagai et al. |
| 2007/0065367 A1* | 3/2007 | Condos ............... A61K 38/21 424/45 |
| 2007/0077290 A1 | 4/2007 | Li et al. |
| 2007/0081963 A1 | 4/2007 | Oh et al. |
| 2007/0196461 A1* | 8/2007 | Weers ............... A61K 9/0073 424/450 |
| 2007/0267010 A1 | 11/2007 | Fink et al. |
| 2008/0089927 A1 | 4/2008 | Malinin |
| 2008/0108104 A1* | 5/2008 | Eckstein ............... C12Q 1/04 435/34 |
| 2008/0131497 A1 | 6/2008 | Perkins et al. |
| 2008/0246472 A1 | 10/2008 | Igney et al. |
| 2009/0104256 A1* | 4/2009 | Gupta ............... A61K 9/0078 424/450 |
| 2009/0269396 A1 | 10/2009 | Cipolla et al. |
| 2009/0274754 A1 | 11/2009 | Cipolla et al. |
| 2010/0068257 A1 | 3/2010 | Boni et al. |
| 2010/0196455 A1 | 8/2010 | Malinin |
| 2010/0260829 A1 | 10/2010 | Boni et al. |
| 2011/0064796 A1 | 3/2011 | Cipolla et al. |
| 2011/0159079 A1 | 6/2011 | Li et al. |
| 2012/0010162 A1 | 1/2012 | Norling |
| 2012/0077786 A1* | 3/2012 | Byron ............... A61K 31/203 514/167 |
| 2012/0192861 A1 | 8/2012 | Surber |
| 2012/0244206 A1 | 9/2012 | Cipolla et al. |
| 2013/0028960 A1 | 1/2013 | Weers |
| 2013/0034534 A1* | 2/2013 | Kroneberg ........... A61M 11/005 424/94.6 |
| 2013/0052260 A1 | 2/2013 | Weers |
| 2013/0064883 A1 | 3/2013 | Weers |
| 2013/0071468 A1 | 3/2013 | Weers |
| 2013/0071469 A1 | 3/2013 | Weers |
| 2013/0089598 A1 | 4/2013 | Gupta |
| 2013/0136788 A1 | 5/2013 | Gupta |
| 2013/0330400 A1 | 12/2013 | Perkins et al. |
| 2013/0330440 A1 | 12/2013 | Fulgham |
| 2014/0018431 A1* | 1/2014 | Wade ............... A61K 31/557 514/569 |
| 2014/0072620 A1 | 3/2014 | Weers |
| 2014/0248335 A1 | 9/2014 | Malinin |
| 2014/0314835 A1 | 10/2014 | Boni et al. |
| 2015/0272880 A1 | 10/2015 | Seidel et al. |
| 2016/0113927 A1 | 4/2016 | Weers |
| 2016/0143849 A1 | 5/2016 | Gupta |
| 2016/0151402 A1 | 6/2016 | Gupta |
| 2016/0184301 A1 | 6/2016 | Weers |
| 2016/0184302 A1 | 6/2016 | Weers |
| 2016/0271125 A1 | 9/2016 | Boni et al. |
| 2016/0317563 A1 | 11/2016 | Weers |
| 2016/0317564 A1 | 11/2016 | Weers |
| 2016/0354371 A1 | 12/2016 | Weers |
| 2017/0014342 A1 | 1/2017 | Li et al. |
| 2017/0087155 A1 | 3/2017 | Weers |
| 2017/0100420 A1 | 4/2017 | Boni et al. |
| 2017/0360816 A1 | 12/2017 | Eagle et al. |

FOREIGN PATENT DOCUMENTS

| | | |
|---|---|---|
| CA | 2838111 | 6/2007 |
| EP | 0069307 | 1/1983 |
| EP | 0274431 | 5/1994 |
| EP | 2457609 | 5/2012 |
| GB | 2145107 | 3/1985 |
| JP | S63-500175 | 1/1988 |
| JP | S63-239213 | 10/1988 |
| JP | H10-511363 | 11/1998 |
| JP | 2006-028069 | 2/2006 |
| UA | 27298 | 10/2007 |
| UA | 27804 | 11/2007 |
| WO | WO 85/00968 | 3/1985 |
| WO | WO 86/06959 | 12/1986 |
| WO | WO 87/00043 | 1/1987 |
| WO | WO 87/02219 | 4/1987 |

(56) References Cited

FOREIGN PATENT DOCUMENTS

| WO | WO 88/04573 | 6/1988 |
|---|---|---|
| WO | WO 91/16882 | 11/1991 |
| WO | WO 93/12240 | 6/1993 |
| WO | WO 94/12155 | 6/1994 |
| WO | WO 94/12156 | 6/1994 |
| WO | WO 94/22430 | 10/1994 |
| WO | WO 96/08235 | 3/1996 |
| WO | WO 96/19199 | 6/1996 |
| WO | WO 96/19972 | 7/1996 |
| WO | WO 97/29851 | 8/1997 |
| WO | WO 99/30686 | 6/1999 |
| WO | WO 99/61003 | 12/1999 |
| WO | WO 99/65466 | 12/1999 |
| WO | WO 00/27359 | 5/2000 |
| WO | WO 00/29103 | 5/2000 |
| WO | WO 00/45791 | 8/2000 |
| WO | WO 01/05373 | 1/2001 |
| WO | WO 01/18280 | 3/2001 |
| WO | WO 01/32246 | 5/2001 |
| WO | WO 2002/032400 | 4/2002 |
| WO | WO 2002/043699 | 6/2002 |
| WO | WO 2003/045965 | 6/2003 |
| WO | WO 2003/075889 | 9/2003 |
| WO | WO 2003/075890 | 9/2003 |
| WO | WO 2004/002453 | 1/2004 |
| WO | WO 2004/047802 | 6/2004 |
| WO | WO 2004/054499 | 7/2004 |
| WO | WO 2004/110346 | 12/2004 |
| WO | WO 2006/108556 | 10/2006 |
| WO | WO 2007/011940 | 1/2007 |
| WO | WO 2007/012191 | 2/2007 |
| WO | WO 2007/067520 | 6/2007 |
| WO | WO 2007/117509 | 10/2007 |
| WO | WO 2007/117550 | 10/2007 |
| WO | WO 2008/039989 | 4/2008 |
| WO | WO 2008/137717 | 11/2008 |
| WO | WO 2008/137917 | 11/2008 |
| WO | WO-2009-045116 * | 4/2009 |
| WO | WO 2010/045209 | 4/2010 |
| WO | WO 2012/069531 | 5/2012 |
| WO | WO 2013/177226 | 11/2013 |
| WO | WO 2015/017807 | 2/2015 |
| WO | WO 2015/175939 | 11/2015 |

OTHER PUBLICATIONS

Written Opinion for International Application No. PCT/US2009/060468, dated Jun. 24, 2010, 3 pages.
Supplementary European Search Report for European Application No. 03816990.0, dated Jan. 12, 2009, 5 pages.
International Search Report for International Application No. PCT/US2003/034240, dated Jul. 12, 2005, 1 page.
International Preliminary Report on Patentability for International Application No. PCT/US2003/034240, dated May 6, 2013, 5 pages.
Supplementary European Search Report for European Application No. 06787716.7, dated Dec. 29, 2011, 7 pages.
Generics [UK] Ltd.'s Notice of Opposition for European Application No. 06787716.7, filed Jun. 4, 2014, 17 pages.
Patentee's Response to Notice of Opposition and Declaration of Lee Leserman for European Application No. 06787716.7, filed Jan. 16, 2015, 58 pages.
International Search Report and Written Opinion for International Application No. PCT/US2006/027859, dated Aug. 14, 2007, 8 pages.
International Preliminary Report on Patentability for International Application No. PCT/US2006/027859, dated Jan. 22, 2008, 6 pages.
Supplementary European Search Report for European Application No. 07754853, dated Jan. 16, 2013, 8 pages.
International Search Report and Written Opinion for International Application No. PCT/US2007/008404, dated Sep. 26, 2008, 6 pages.
International Preliminary Report on Patentability for International Application No. PCT/US2007/008404, dated Oct. 21, 2008, 4 pages.
European Search Report for European Patent Application No. 11159754.8, dated Jun. 22, 2011, 5 pages.
European Search Report for European Patent Application No. 13175824.5, dated Sep. 16, 2013, 8 pages.
European Search Report for European Application No. 14183066.1, dated Dec. 16, 2014, 11 pages.
Supplementary European Search Report for European Application No. 06847502.9, dated Dec. 5, 2012, 7 pages.
International Search Report and Written Opinion for International Application No. PCT/US2006/046360, dated Oct. 17, 2007, 5 pages.
International Preliminary Report on Patentability for International Application No. PCT/US2006/046360, dated Jun. 11, 2008, 5 pages.
European Search Report for European Application No. 16156100.6, dated Jul. 25, 2016, 6 pages.
European Search Report for European Application No. 16156099.0, dated Jul. 25, 2016, 7 pages.
Supplementary European Search Report and Written Opinion for European Application No. 07754936.8, dated Jan. 18, 2013, 9 pages.
International Search Report and Written Opinion for International Application No. PCT/US2007/008500, dated Sep. 26, 2008, 9 pages.
International Preliminary Report on Patentability for International Application No. PCT/US2007/008500, dated Oct. 21, 2008, 8 pages.
Supplementary European Search Report for European Application No. 13793204.2, dated Sep. 25, 2015, 5 pages.
International Search Report and Written Opinion for International Application No. PCT/US2013/042113, dated Sep. 4, 2013, 13 pages.
International Preliminary Report on Patentability for International Application No. PCT/US2013/042113, dated Nov. 25, 2014, 9 pages.
Allen, T. M. et al., "Effect of liposome size and drug release properties of pharmacokinetics of encapsulated drug to rats," The Journal of Pharmacology and Experimental Therapeutics, 226(2):539-544 (1983).
Alton et al., "Cationic lipid-mediated CFTR gene transfer to the lungs and nose of patients with cystic fibrosis: a double-blind placebo-controlled trial," The Lancet, 353(9157):947-954 (1999).
Andrews, J. M., "Determination of minimum inhibitory concentrations," Journal of Antimicrobial Chemotherapy, 48(S1):5-14 (2001).
Antos, M. et al., "Antibacterial activity of liposomal amikacin against Pseudomonas aeruginosa in vitro," Pharmacological Research, 32(1/2):84-87 (1995).
Bakker-Woudenberg, I. et al., "Efficacy of gentamicin or ceftazidine entrapped in liposomes with prolonged blood circulation and enhanced localization in Klebsiella pneumoniae-infected lung tissue," The Journal Infectious Diseases, 171:938-947 (1995).
Bakker-Woudenberg, I. A. J. M. et al., "Long-Circulating Sterically Stabilized Liposomes in the Treatment of Infections," Method in Enzymology, Available online Feb. 21, 2005, 391:228-260 (2005).
Bakker-Woudenberg et al. (2002). Ciprofloxacin in polyethylene glycol-coated liposomes: efficacy in rat models of acute or chronic Pseudomonas aeruginosa infection. Antimicrobial Agents and Chemotherapy 46(8), pp. 2575-2581.
Bakker-Woudenberg et al. (2001). Improved efficacy of ciprofloxacin administered in polyethylene glycol-coated liposomes for treatment of Klebsiella pneumoniae pneumonia in rats. Antimicrobial Agents and Chemotherapy 45(5), pp. 1487-1492.
Ball, V. et al., "Complexation mechanism of bovine serum albumin and poly(allylamine hydrochloride)," J. Phys. Chem. B., 106(9):2357-2364 (2002).
Bangham, A. D. et al., "Diffusion of univalent ions across the lamellae of swollen phospholipids," J. Mol. Biol., 13(1):238-252 (1965).

(56) References Cited

OTHER PUBLICATIONS

Bangham, A. D., Introduction, "Liposomes: An Historical Perspective," in: Liposomes, Ostro, M. J. (ed.), pp. 1-25, Marcel Dekker, Inc., New York (1983).
Bargoni, A. et al., "Transmucosal transport of tobramycin incorporated in solid lipid nanoparticles (SLN) after duodenal administration to rats. Part II—Tissue distribution," Pharmacological Research, 43(5):497-502 (2001).
Beaulac, C. et al., "Eradication of Mucoid Pseudomonas aeruginosa with Fluid Liposome-Encapsulated Tobramycin in an Animal Model of Chronic Pulmonary Infection," Antimicrobial Agents and Chemotherapy, 40(3):665-669 (1996).
Beaulac, C. et al., "In-vitro bactericidal efficacy of sub-MIC concentrations of liposome-encapsulated antibiotic against Gram-negative and Gram-positive bacteria," Journal of Antimicrobial Chemotherapy, 41:35-41 (1998).
Beaulac, C. et al., "Aerolization of low phase transition temperature liposomal tobramycin as a dry powder in an animal model of chronic pulmonary infection caused by Pseudomonas aeruginosa," Journal Drug Targeting, 7(1):33-41 (1999).
Beaulac, C. et al., "In vitro kinetics of drug release and pulmonary retention of microencapsulated antibiotic in liposomal formulations in relation to the lipid composition," Journal Microencapsulation 14(3):335-348 (1997).
Bedard et al. (1989). Interaction of the fluoroquinolone antimicrobial agents ciprofloxacin and enoxacin with liposomes. Antimicrobial Agents and Chemotherapy 33(8), pp. 1379-1382.
Bermudez, L. E. et al., "Treatment of disseminated *Mycobacterium avium* complex infection of beige mice with liposome-encapsulated aminoglycosides," The Journal of Infectious Diseases, 161(6):1262-1268 (1990).
Bhavane, R. et al., "Agglomerated vesicle technology: a new class of particles for controlled and modulated pulmonary drug delivery," Journal of Controlled Release 93(1):15-28 (Nov. 2003).
Bhavane (2006). Nanoparticle agglomerates for pulmonary drug delivery. A dissertation presented to the faculty of the University of Texas Health Science Center at Houston of Health Information Sciences. UMI No. 3237380.
Bilodeau, M. et al., "Kanamycin aerosol therapy in 200 cases of bronchopulmonary suppurations," Can. Med. Assoc. J., 89:537-541 (1963) (with English Abstract).
Blaser, J. et al., "Once daily dosing of aminoglycosides," Eur. Clin. Microbiol. Infect. Dis., 14(12):1029-1038 (1995).
Bucke, W. E. et al., "Surface-modified amikacin-liposomes: organ distribution and interaction with plasma proteins," Journal of Drug Targeting, 5(2):99-108 (1997).
Bunderberg de Jong, H. G. et al., Koazevation (Entmischung in Kolloidalen Systemen), Koll, Zeitsch, 50(10):39-48 (1930).
Cantin, A. M. et al., "Aerosolized prolastin suppresses bacterial proliferation in a model of chronic pseudomonas aeruginosa lung infection," Am. J. Respir. Crit. Care Med., 160:1130-1135 (1999).
Carlier, M. B. et al., "Inhibition of lysosomal phospholipases by aminoglycoside antibiotics: in vitro comparative studies," Antimicrobial Agents and Chemotherapy, 23(3):440-449 (1983).
Cash, H. A. et al., "A rat model of chronic respiratory infection with Pseudomonas aeruginosa," American Review of Respiratory Disease, 119(3):453-459 (1979).
Challoner, P. B. et al., "Gamma Scintigraphy Lung Deposition Comparison of TOBI in the PARI LC PLUS Nebulizer and the Aerodose Inhaler," American Thoracic Society 97th International Conference, San Francisco, California, Aerogen, Inc. (2001).
Chambless, J. D. et al., "A three-dimensional computer model of four hypothetical mechanisms protecting biofilms from antimicrobials," Appl. Environ. Microbiol., 72(3):2005-2013 (2006).
Chan, C. H. S. et al., "Mycobacteria as a cause of infective exacerbation in bronchiectasis," Postgrad. Med. J., 68:896-899 (1992).
Chapman, D., "Physicochemical Properties of Phospholipids and Lipid-Water Systems," In: Liposome Technology, Chapter 1, vol. I, Preparation of Liposomes, Gregoriadis G. (ed.), CRC Press, Inc., Boca Raton, Florida, pp. 1-18 (1984).
Chmiel, J. F. et al., "State of the art: why do the lungs of patents with cystic fibrosis become infected and why can't they clear the infection?", Respiratory Research, 4:8-20 (2003).
Ciofu, O. et al., "Occurrence of Hypermutable Pseudomonas aeruginosa in Cystic Fibrosis Patients Is Associated with the Oxidative Stress Caused by Chronic Lung Inflammation," Antimicrobial Agents and Chemotherapy, 49(6):2276-2282 (Jun. 2005).
Clancy, J. P. et al., "Phase II studies of nebulised Arikace in CF patients with Pseudomonas aeruginosa infection," Thorax, 68(9):818-825 (2013).
Clay. M. M. et al., "Assessment of jet nebulisers for lung aerosol therapy," Lancet, 2:592-594 (1983).
ClinicalTrials.gov, "Safety and Efficacy Study of Ciprofloxacin for Inhalation in Patients With Non-Cystic Fibrosis Bronchiectasis 'ORBIT-1'", Identifier: NCT00889967, First Received: Apr. 27, 2009, 3 pages.
Colardyn, F., "The efficacy and safety of isepamicin and ceftazidime compared with amikacin and ceftazidime in acute lower respiratory tract infection," Journal of Chemotherapy, 7(2):129-135 (1995).
Coleman, L. T. et al., "Bronchiectasis in children," Journal of Thoracic Imaging, 10(4)268-279 (1995).
Comis, R. L., "Carboplatin in the treatment of non-small cell lung cancer: a review," Oncology, 50(2):37-41 (1993).
Conley et al., "Aerosol Delivery of Liposome-Encapsulated Ciprofloxacin: Aerosol Characterization and Efficacy against Francisella tularensis Infection in Mice," Antimicrobial Angents, 41(6):1288-1292 (Jun. 1997).
Cooksey, R. C. et al., "Antimicrobial susceptibility patterns of *Streptococcus pneumoniae*," Antimicrobial Agents and Chemotherapy, 13(4):645-648 (1978).
Costerton, J. W. et al., "Bacterial biofilms: A common cause of persistent infections," Science, 284:1318-1322 (1999).
Couvreur, P. et al., "Liposomes and nanoparticles in the treatment of intracellular bacterial infections," Pharmaceutical Research, 8(9):1079-1085 (1991).
Cremades, M. J. et al., "Repeated pulmonary infection by Nocardia asteroides complex in a patent with bronchiectasis," Respiration, 65:211-213 (1998).
Crowther, N. R. et al., "Inhaled aminoglycoside (gentamicin) in bronchiectasis: Dry powder vs. nebulization vs. intravenous therapy," Clinical and Investigative Medicine, Annual Meeting of the Canadian Society for Clinical Investigation, The Royal College of Physicians and Surgeons of Canada and Participating Societies, Toronto, Canada, Abstract 530 (Sep. 24-27, 1998).
Currie, D. C., "Nebulisers for bronchiectasis," Thorax, 52(Suppl. 2):S72-S74 (1997).
Cymbala, A. A. et al., "The Disease-Modifying Effects of Twice-Weekly Oral Azithromycin in Patients with Bronchiectasis," Treat Respir. Med. 2005;4(2):117-122.
Cynamon, M. H. et al., "Liposome-Encapsulated-Amikacin Therapy of *Mycobacterium avium* Complex Infection in Geige Mice," Antimicrobial Agents and Chemotherapy, 33(8):1179-1183 (1989).
Dally, M. B. et al., "Ventilatory effects of aerosol gentamicin," Thorax, 33:54-56 (1978).
Damaso, D. et al., "Susceptibility of current clinical isolates of Pseudomonas aeruginosa and enteric gram-negative bacilli to amikacin and other aminoglycoside antibiotics," The Journal of Infectious Diseases, 134:S394-S390 (1976).
Deamer, D. W. et al., "Liposome Preparation: Methods and Mechanisms," Chapter 1 in: Liposomes, Ostro, M. J. (ed.), Marcel Dekker, Inc., New York (1983), 27 pages.
Dees, C. et al., "The mechanism of enhanced intraphagocytic killing of bacteria by liposomes containing antibiotics," Veterinary Immunology and Immunopathology, 24:135-146 (1990).
Del Porto, P. et al., "Dysfunctional CFTR alters the bactericidal activity of human macrophages against Pseudomonas aeruginosa," PLoS ONE, 6(5):e19970 (2011).
Demaeyer, P. et al., "Disposition of liposomal gentamicin following intrabronchial administration in rabbits," Journal Microencapsulation, 10(1):77-88 (1993).

(56) References Cited

OTHER PUBLICATIONS

Deol, P. et al., "Lung specific stealth liposomes: stability, biodistribution and toxicity of liposomal antitubular drugs in mice," Biochimica et Biophysica Acta, 1334:161-172 (1997).
Dequin, P. F. et al., "Urinary excretion reflects lung deposition of aminoglycoside aerosols in cystic fibrosis," Eur. Respir. J., 18(2):316-322 (2001).
Desai et al., "A facile method of delivery of liposomes by nebulization," Journal of Controlled Release, 84(1-2):69-78 (2002).
Desai, T. R. et al., "Determination of surface free energy of interactive dry powder liposome formulations using capillary penetration technique," Colloids and Surfaces B: Biointerfaces, 22:107-113 (2001).
Desai, "Delivery of liposomes in dry powder form: aerodynamic dispersion properties," European Journal of Pharmaceutical Sciences 20:459-467 (2003).
Di Ninno et al. (1993). Liposome-encapsulated ciprofloxacin is effective in the protection and treatment of BALB/c mice against Francisella tularensis. The Journal of Infectious Diseases 168, pp. 793-794.
Dickie, K. J. et al., "Ventilatory effects of aerosolized kanamycin and polymyxin," Chest, 63(5):694-697 (1973).
Dong, C. et al., "Acacia-gelatin microencapsulated liposomes: preparation, stability and release of acetylsalicylic acid," Pharmaceutical Research, 10(1):141-146 (1993).
Doring, G. et al., "Antibiotic therapy against Pseudomonas aeruginosa in cystic fibrosis: a European consensus," Eur Respir J., 16(4):749-767 (2000).
Drenkard, E. et al., "Pseudomonas biofilm formation and antibiotic resistance are linked to phenotypic variation," Nature, 416:740-743 (2002).
Eboka (2005). Aqueous solubility of ciprofloxacin in the presence of metal cations. Tropical Journal of Pharmaceutical Research, 4(1), pp. 349-354.
Ehlers, S. et al., "Liposomal amikacin for treatment of *M. avium* Infections in clinically relevant experimental settings," Zbl. Bakt., 284:218-231 (1996).
Eigen (1995). A multicenter study of alternate-day prednisone therapy in patients with cystic fibrosis. The Journal of Pediatrics, 126(4), pp. 515-523.
El-Din, M. A. T. et al., "Nebulizer therapy with antibiotics in chronic suppurative lung disease," Journal of Aerosol Medicine, 7(4):345-350 (1994).
Eller, J. M. et al., "The therapy of bronchiectasis," Deutsche Medizinische Wochenschrift, 118(44):1608-1610 (1993).
Farber, J. E. et al., "The use of aerosol penicillin and streptomycin in bronchopulmonary infections," California Medicine, 73(3):214-217 (1950).
Fielding, R. M. et al., "Pharmacokinetics and Urinary Excretion of Amikacin in Low-Clearance Unilamellar Liposomes after a Single or Repeated Intravenous Administration in the Rhesus Monkey," Antimicrobial Agents and Chemotherapy, 43(3):503-509 (1999).
Finke, W., "Long-term antibiotic therapy in chronic bronchitis and infectious asthma. Control and prevention of bronchopulmonary disease." Antibiotics and Chemotherapy, 4(3):319-329 (1954).
Finlay, W. H. et al., "Regional lung deposition of nebulized liposome-encapsulated ciprofloxacin," International Journal of Pharmaceutics (Amsterdam), 167(1-2):121-127 (Jun. 1, 1998).
Fountain, M. W. et al., "Treatment of *Brucella canis* and *Brucella abortus* In vitro and in vivo by stable plurilamellar vesicle-encapsulated aminoolycosides," The Journal of Infectious Diseases, 152(3):529-535 (1985).
Garcia, A. T., "Efficacy of amikacin sulfate in lower respiratory infections," Investigacion Medica Internacional, 9(3):235-240 (1982) (with English Abstract).
Geller, D. E. et al., "Pharmacokinetics and bioavailability of aerosolized tobramycin in cystic fibrosis," Chest, 122(1):219-226 (2002).
Gibson, R. L. et al., "Pathophysiology and management of pulmonary infections in cystic fibrosis," American Journal of Respiratory and Critical Care Medicine, 168(8):918-951 (2003).
Gibson, R. L. et al., "Significant microbiological effect of inhaled tobramycin in young children with cystic fibrosis," American Journal of Respiratory and Critical Care Medicine, 167(6):841-849 (2003).
Gilbert, B. E. et al., "Tolerance of volunteers to cyclosporine A-dilauroylphosphatidylcholine liposome aerosol," American Journal of Respiratory and Critical Care Medicine, 156(6):1789-1793 (1997).
Gleiser, C. A. et al., "Pathology of experimental respiratory anthrax in Macaca mulatta," Brit. J. Exp. Path., 44:416-426(1963).
Goldman, J. M. et al., "Inhaled micronised gentamicin powder: a new delivery system," Thorax, 45:939-940 (1990).
Gonzales-Rothi, R. J. et al., "Liposomes and pulmonary alveolar macrophages: functional and morphologic interactions," Experimental Lung Research, 17:687-705 (1991).
Goss, C. H. et al., "Update on cystic fibrosis epidemiology," Current Opinion in Pulmonary Medicine, 10(6):510-514 (2004).
Graczyk, J. et al., "Staphylococcal pneumonia—analysis of material of patients treated in lung diseases hospital in years 1981-1994," Pneumonologia | Alergologia Polska, 65(11-12):767-774 (1997) (with English Abstract).
Greene, K. E. et al., "Radiographic changes in acute exacerbations of cystic fibrosis in adults: A pilot study," AJR, 163:557-562 (1994).
Gunther, A. et al., "Surfactant alteration and replacement in acute respiratory distress syndrome," Respiratory Research, 2(6): 353-364 (2001).
Gursoy et al. (1997). Characterization of ciprofloxacin liposomes; derivative ultraviolet spectrophotometric determinations. J. Microencapsulation 14(6), pp. 769-776.
Hagwood, S. et al., "Structure and properties of surfactant protein B," Biochimica et Biophysics Acta., 1408:150-160 (1998).
Hansen, C. R. et al., "Long-term azithromycin treatment of cystic fibrosis patients with chronic pseudomonas aeruginosa infection: an observational cohort study," Journal of Cystic Fibrosis, 4(1):35-40 (2005).
Helbich, T. et al., "High-resolution computed tomography of the lung in young patients with cystic fibrosis," Radiologe, 33(3):142-146 (1993) (English Abstract).
Hess, D. et al., "Medication nebulizer performance. Effects of diluent volume, nebulizer flow, and nebulizer brand," Chest, 110:498-505 (1996).
Hess, D. R., "Nebulizers: Principles and Performance," Respiratory Care, 45(6):609-622 (2000).
Hewitt, W. L. et al., "Antibiotic therapy of abscess of the lung and bronchiectasis," California Medicine, 76(5):319-324 (1952).
Hoffman, L. R. et al., "Aminoglycoside antibiotics induce bacterial biofilm formation," Nature, 436:1171-1175 (2005).
Honeybourne, D., "Antibiotic penetration in the respiratory tract and implications for the selection of antimicrobial therapy," Current Opinion in Pulmonary Medicine 1997, 3(2):170-174.
Howell, S. B., "Clinical applications of a novel sustained-release injectable drug delivery system: Depofoam Technology," Cancer Journal, 7:219-227 (2001).
Hrkach, J. S. et al., "Synthesis of poly(L-lactic acid-co-L-lysine) graft copolymers," Macromolecules, 28:4736-4739 (1995).
Hrkach, J. S. et al., "Poly(L-Lactic acid-co-amino acid) graft copolymers: A class of functional biodegradable biomaterials," In: Hydrogels and Biodegradable Polymers for Bioapplications, Chapter 8, ACS Symposium Series No. 627, Ottenbrite, R. M. et al. (ads.), American Chemical Society, pp. 93-102 (1996).
Huang, L. et al., "Progress of liposome's applications in biomedicine," International Journal of Biologicals, 29(3):130-132 and 137 (2006).
Huang et al. (2006). Pulmonary delivery of insulin by liposomal carriers. Journal of Controlled Release 113, pp. 9-14.
Hubble, D., "Discussion on respiratory catarrh in children," Proceedings of the Royal Society of Medicine, 52(9):701-710 (1959).
Hung, O. R. et al., "Pharmacokinetics of inhaled liposome-encapsulated fentanyl," Anesthesiology, 83(2): 277-284 (Aug. 1995).

(56) References Cited

OTHER PUBLICATIONS

Hung, J. C. et al., "Evaluation of two commercial jet nebulisers and three compressors for the nebulisation of antibiotics," Archives of Disease in Childhood, 71(4):335-338 (Oct. 1994).
Hunt, B. E. et al., "Macromolecular mechanisms of sputum inhibition of tobramycin activity," Antimicrobial Agents and Chemotherapy, 39(1):34-39 (1995).
Ikegami, M. et al., "Surfactant protein metabolism in vivo," Biochimica et Biophysics Acta, 1408:218-225 (1998).
Ikemoto, H. et al., "Susceptibility of bacteria isolated from the patients with lower respiratory tract infections to antibiotics," The Japanese Journal of Antibiotics, 42(11):2350-2353 (1989).
Ip, M. S. M. et al., "Bronchiectasis and related disorders," Respirology, 1:107-114 (1996).
Ishii, F. et al., "Procedure for Preparation of Lipid Vesicles (Liposomes) Using the Coacervation (Phase Separation) Technique," Langmuir, 11(2):483-486 (1995).
Janoff, A. S. et al., "Unusual lipid structures selectively reduce the toxicity of amphotericin B," Proc. Nat. Acad. Sci. USA, 85:6122-6126 (1988).
Jayaraman, S. et al., "Noninvasive in vivo fluorescence measurement of airway-surface liquid depth, salt concentration, and pH," J. Clin. Invest. 107:317-324 (2001).
Johansson, J., "Structure and properties of surfactant protein C," Biochimica et Biophysica Acta, 1408:161-172 (1998).
Johnston, M. J. W. et al., "Therapeutically optimized rates of drug release can be achieved by varying the drug-to-lipid ratio in liposomal vincristine formulations," Biochimica et Biophysica Acta, 1758:55-64 (2006).
Katare, O. P. et al., "Enhanced in vivo Performance of LiposomalIndomethacin Derived From Effervescent Granule Based Proliposomes," J. Microencapsulation, 12(5):487-493 (1995).
Kesavalu, L. et al., "Differential effects of free and liposome encapsulated amikacin on the survival of *Mycobacterium avium* complex in mouse peritoneal macrophages," Tubercle, 71:215-218 (1990).
Kim, E. K. et al., "Pharmacokinetics of intravitreally injected liposomes encapsulated tobramycin in normal rabbits," Yonsei Medical Journal, 31(4):308-314 (1990).
Klemens, S. P. et al., "Liposome-encapsulated-gentamicin therapy of *Mycobacterium avium* complex infection in beige mice," Antimicrobial Agents and Chemotherapy, 34(6):967-970 (1990).
Knoch, M. et al., "The customised electronic nebuliser: a new category of liquid aerosol drug delivery systems," Expert Opin. Drug Deliv., 2(2):377-390 (2005).
Knox, K. et al., "Chronic bronchitis. An attempt to control chronic infection with Haemophilus influenzae by aerosol therapy," The Lancet, pp. 120-122 (1955).
Labiris, N. R. et al., "Pulmonary drug delivery. Part II: The role of inhalant delivery devices and drug formulations in Therapeutic effectiveness of aerosolized medications," Br.J.Clin.Pharmacol., 56(6):600-612 (2003).
Lagace, J. et al., "Liposome-encapsulated antibiotics: preparation, drug release and antimicrobial activity against Pseudomona aeruginosa," Journal Microencapsulation, 8(1) 53-61 (1991).
Landyshev, Y. S. et al., "Clinical and experimental aspects of liposomal hydrocortisone treatment of bronchial asthma," Ter. Arkh., 74(8):45-48 (2002) (with English Abstract).
Lass, J. S. et al., "New advances in aerosolised drug delivery: vibrating membrane nebuliser technology," Expert Opin Drug Deliv., 3(5):693-702 (2006).
Le Brun, P. P. H. et al., "A review of the technical aspects of drug nebulization," Pharmacy World & Science, 22(3):75-81 (2000).
Le Brun, P. P. H. et al., "Inhalation of tobramycin in cystic fibrosis part 1: The choice of a nebulizer," International Journal of Pharmaceutics, 189:205-214 (1999).
Le Brun, P. P. H. et al., "Inhalation of tobramycin in cystic fibrosis part 2: Optimization of the tobramycin solution for a jet and ultrasonic nebulizer," International Journal of Pharmaceutics, 189:215-225 (1999).

Le Brun, P. P. H. et al., "Dry powder inhalation of antibiotics in cystic fibrosis therapy: part 2. Inhalation of a novel colistin dry powder formulation: a feasibility study in healthy volunteers and patients," European Journal of Pharmaceutics and Biopharmaceutics, 54:25-32 (2002).
Li, Z. et al., "Nebulization of liposomal amikacin formulations: SLIT Amikacin," Respiratory Drug Delivery, 3:801-804 (2006).
Li, Z. et al., "Characterization of nebulized liposomal amikacin (Arikace) as a function of droplet size," Journal of Aerosol Medicine and Pulmonary Drug Delivery, 21(3):245-253 (2008).
Lin, H.-C. et al., "Inhaled gentamicin reduces airway neutrophil activity and mucus secretion in bronchiectasis," Am. J. Respir. Crit. Care Med., 155:2024-2029 (1997).
Lutwyche, P. et al., "Intracellular delivery and antibacterial activity of gentamicin encapsulated in pH-sensitive liposomes," Antimicrobial Agents and Chemotherapy, 42(10):2511-2520 (1998).
Magallanes, M. et al., "Liposome-incorporated ciprofloxacin in treatment of murine salmonellosis," Antimicrobial Agents and Chemotherapy, Nov. 1993, 37(11):2293-2297.
Majumdar, S. et al., "Efficacies of Liposome-Encapsulated Streptomycin and Ciprofloxacin against *Mycobacterium avium-M. intracellulare* Complex Infections in Human Peripheral Blood Monocyte/Macrophages," Antimicrobial Agents and Chemotherapy, 36(12):2808-2815 (Dec. 1992).
Marcotte, G. V. et al., "Chronic productive cough and bronchiectasis in a 40-year-old woman," Annals of Allergy, Asthma & Immunology, 78(6):559-564 (1997).
Marier, J. F. et al., "Liposomal tobramycin against pulmonary infections of Pseudomonas aeruginosa: a pharmacokinetic and efficacy study following single and multiple intratracheal administrations in rats," Journal Antimicrobial Chemotherapy, 52:247-252 (2003).
Marier, J-F. et al., "Pharmacokinetics and efficacies of liposomal and conventional formulations of tobramycin after intratracheal administration in rats with pulmonary burkholderia cepacia infection," Antimicrobial Agents and Chemotherapy, 46(12):3776-3781 (2002).
Mariotti, A. B. et al., "Aerosol therapy with tobramycin in exacerbations of chronic obstructive lung disease (7 cases)," 66(2):198-202 (1996) (with English Abstract).
Martini, W. Z. et al., "Lung surfactant kinetics in conscious pigs," Am J Physiol., 277(1 Pt 1): E187-E195 (1999).
Marwah, O. S. et al., "Bronchiectasis. How to identify, treat and prevent," Postgrad. Med., 97(2):149-150, 153-156, 159 (1995) (Abstract).
Maurer, N. et al., "Anomalous solubility behavior of the antibiotic ciprofloxacin encapsulated in liposomes: a 1H-NMR study," Biochimica et Biophysica Act, 1374:9-20 (1998).
McAllister, S. M. et al., "Antimicrobial properties of liposomal polymyxin B," Journal of Antimicrobial Chemotherapy, 43:203-210 (1999).
Meers, P. et al., "Biofilm penetration, triggered release and in vivo activity of inhaled liposomal amikacin in chronic Pseudomonas aeruginosa lung infections," Journal of Antimicrobial Chemotherapy, 61(4):859-868 (2008).
Mendelman, P. M. et al., "Aminoglycoside penetration, inactivation, and efficacy in cystic fibrosis sputum," American Review of Respiratory Disease, 132(4):761-765 (1985).
Mercer, R. R. et al., "Cell Number and Distribution in Human and Rat Airways," Am. J. Respir. Cell Mol. Biol., vol. 10, pp. 613-624 (1994).
Mohanty, B. et al., "Systematic of alcohol-induced simple coacervation in aqueous gelatin solutions," Biomacromolecules, 4:1080-1086 (2003).
Mombelli, G. et al., "Anfi-pseudomonas activity in bronchial secretions of patients receiving amikacin or tobramycin as a continuous infusion," Antimicrobial Agents and Chemotherapy, 19(1):72-75 (1981).
Montero et al. (1998). Fluoroquinolone-biomembrane interactions: monolayer and calorimetric studies. Langmuir 14(9), pp. 2451-2454.

(56) References Cited

OTHER PUBLICATIONS

Morgan, J. R. et al., "Preparation and properties of liposome-associated gentamicin," Antimicrobial Agents and Chemotherapy, 17(4):544-548 (1980).
Myers, M. A. et al., "Pulmonary effects of chronic exposure to liposome aerosols in mice," Experimental Lung Research, 19:1-19 (1993).
Nakazawa, S. et al., "Studies on a new aminoglycoside antibiotic, amikacin (BB-K8) in pediatrics," The Japanese Journal of Antibiotics, 27(4):438-445 (1974).
Nasu, M. et al., "Appropriate use of antimicrobial agents," Selection of Anti-infective, Clinic in Japan (Special Number) Infection Disease Study in New Era (first volume), 2003, 61st issue, pp. 718-723.
Newton, D. W. et al., Chapter 4: "Coacervation: Principles and Applications," In: Polymers for Controlled Drug Delivery, Tarcha, P. J. (ed.), CRC Press, Boca Raton, pp. 67-81 (1991).
Nightingale, S. D. et al., "Liposome-encapsulated gentamicin treatment of *Mycobacterium avium-Mycobacterium intracellulare* complex bacteremia in AIDS patients," Antimicrobial Agents and Chemotherapy, 37(9):1869-1872 (1993).
Niven, R. W. et al., "Nebulization of liposomes. I. Effects of lipid composition, 7(11):1127-1133 (1990)"Pharmaceutical Research, 7(11):1127-1133 (1990).
Niven, R. W. et al., "Nebulization of liposomes. II. The effects of size and modeling of solute release profiles," Pharmaceutical Research, 8(2):217-221 (1991).
Niven, R. W. et al., "Nebulization of liposomes. III. The effects of operating conditions and local environment," Pharmaceutical Research, 9(4):515-520 (1992).
Oh, Y-K et al., "Formulation and Efficacy of Liposome-Encapsulated Antibiotics for Therapy of Intracellular *Mycobacterium avium* Infection," Antimicrobial Agents and Chemotherapy, 39(9):2104-2111 (Sep. 1995).
Oizumi, K. et al., "Therapeutic effect of amikacin for infections with gram-negative bacilli, especially for stubborn respiratory infections," The Japanese Journal of Antibiotics, 31(1):15-23 (1978).
Olsen, A. M., "Streptomycin aerosol in the treatment of chronic bronchiectasis: preliminary report," Staff Meetings of the Mayo Clinic, pp. 53-54 (1946).
Olsen, A. M., "Nebulization therapy in bronchiectasis: The use of penicillin and streptomycin aerosols," In: Collected Papers of The Mayo Clinic and The Mayo Foundation, Hewitt, R. M. et al. (eds.), 38:579-586 (1946).
Olsen, A. M., "Nebulization therapy in bronchiectasis: The use of penicillin and streptomycin aerosols," J.A.M.A., 134(11):947-953 (1947).
Omri, A. et al., "Incorporation, release and in-vitro antibacterial activity of liposomal aminoglycosides against Pseudomonas aeruginosa," Journal of Antimicrobial Chemotherapy, 36(4):631-639 (1995).
Omri, A. et al., "Comparison of the bactericidal action of amikacin, netilmicin and tobramtcin in free and liposomal formulation against pseudomonas aeruginosa," Chemotherapy, 42:170-176 (1996).
Omri, A. et al., "Pulmonary retention of free and liposome-encapsulated tobramycin after intratracheal administration in uninfected rats and rats infected with Pseudomonas aeruginosa," Antimicrobial Agents and Chemotherapy, 38(5):1090-1095 (1994).
Pai, V. B. et al., "Efficacy and safety of aerosolized tobramycin in cystic fibrosis," Pediatric Pulmonology, 32(4):314-327 (2001).
Papahadjopoulos, D. et al., "Phospholipid model membranes. I. Structural characteristics of hydrated liquid crystals," Biochimica et Biophysica Acta., 135:624-638 (1967).
Paradisi, F. et al, "Acute and chronic bronchopulmonary infections and aminoglycoside antibiotics," Chemioterapia Antimicrobica, 1(2):224-227 (1978).
Parsek, M. R. et al., "Acyl-homoserine lactone quorum sensing gram-negative bacteria: a signaling mechanism involved in associations with higher organisms," Proc. Nat. Acad. Sci., 97(16):6789-6793 (2000).

Patton, J. S. et al., "The lungs as a portal of entry for systemic drug delivery," Proc. Am. Thor. Soc., 1:338-344 (2004).
Perkins, W. R. et al., "Aerosolization of liposomal amikacin (Arikace) using different nebulizers: Selection of the eflow nebulizer," Poster and Oral Presentation at North American Cystic Fibrosis Conference (Oct. 2007), Pediatric Pulmonology, 42(30):356-357, abs. 434, 12 pages.
Perkins, W. R. et al., "Role of lipid polymorphism in pulmonary surfactant," Science, 273:330-332 (Jul. 1996).
Petersen, E. A. et al., "Liposomal amikacin: improved treatment of *Mycibacterium avium* complex infection in the beige mouse model," Journal Antimicrobial Chemotherapy, 38:819-828 (1996).
Petkowicz, J. et al., "Hypoglycemic Effect of Liposome-Entrapped Insulin Administered by Various Routes into Normal Rats," Pol. J. Pharmacol. Pharm., 41:299-304 (1989).
Pilewski, J. M. et al., "Role of CFTR in airway disease," Physiological Reviews, 79(1):S215-S255 (1999).
Pines, A. et al., "Treatment of severe pseudomonas infections of the bronchi," British Medical Journal, 1:663-665 (1970).
Pines, A. et al., "Gentamicin and colistin in chronic purulent bronchial infections," British Medical Journal, 2:543-545 (1967).
Potter, B. P., "Aerosol antibiotic therapy in suppurative diseases of the lung and bronchi," Aerosol Antibiotic Therapy, 25:436-448 (1949).
Poyner, E. A. et al., "A comparative study on the pulmonary delivery of tobramycin encapsulated into liposomes and PLA microspheres following intravenous and endotracheal delivery," Journal of Controlled Release, 35(1):41-48 (1995).
Poyner, E. A. et al., "Preparation, properties and the effects of free and liposomal tobramycin on siderophore production by Pseudomonas aeruginosa," Journal of Antimicrobial Chemotherapy, 34:43-52 (1993).
Press Release, "Transave Announces Positive Phase II Results for Once-Daily Arikace in the Treatment of Cystic Fibrosis Patents Who Have Pseudomonas Lung Infections," Presented at the European Cystic Fibrosis Society Conference, Monmouth Junction, NJ, Jun. 13, 2008, 3 pages.
Price, C. I. et al., "Liposome delivery of aminoglycosides in burn wounds," Surgery, Gynecology & Obstetrics, 174:414-418 (1992).
Price, C. I. et al., "Liposome encapsulation: a method for enhancing the effectiveness of local antibiotics," Surgery, 115(4):480-487 (1994).
Price, C. I. et al., "Enhanced effectiveness of intraperitoneal antibiotics administered via liposomal carrier," Arch Surgery, 124:1411-1415 (1989).
Price, K. E. et al., "Amikacin, an aminoglycoside with marked activity against antibiotic-resistant clinical isolates," The Journal of Infectious Diseases, 134:S249-S261 (1976).
Ramsammy, L. S. et al., "The effect of gentamicin on the biophysical properties of phosphatidic acid liposomes is influenced by the O—C=O group of the lipid," Biochemistry, 27:8249-8254 (1988).
Ramsey, B. W. et al., "Intermittent administration of inhaled tobramycin in patients with cystic fibrosis. Cystic Fibrosis Inhaled Tobramycin Study Group," The New England Journal of Medicine, 340(1):23-30 (1999).
Ramsey, B. W. et al., "Efficacy of aerosolized tobramycin in patients with cystic fibrosis," The New England Journal of Medicine, 328:1740-1746 (1993).
Rastogi et al. (2006). Particulate and vesicular drug carriers in the management of tuberculosis. Current Drug Delivery 3(1), pp. 121-128.
Rau, J. L. et al., "Performance Comparison of Nebulizer Designs: Constant-Output, Breath-Enhanced, and Dosimetric," Respir. Care 2004;49(2):174-179.
Roehrborn, A. A. et al., "Lipid-based slow-release formulation of amikacin sulfate reduces foreign body-associated infections in mice," Antimicrobial Agents and Chemotherapy, 39(8):1752-1755 (1995).
Sabra, W. et al., "Physiological responses of pseudomonas aeruginosa PAO1 to oxidative stress in controlled microaerobic and aerobic cultures," Microbiology, 148:3195-3202 (2002).

(56) References Cited

OTHER PUBLICATIONS

Schaad, U. B. et al., "Efficacy of inhaled amikacin as adjunct to intravenous combination therapy (ceftazidime and amikacin) in cystic fibrosis," Journal of Pediatrics, 111(4):599-605 (Oct. 1987).
Schentag, J. J., Antimicrobial action and pharmacokinetics/pharmacodynamics: the use of AUIC to improve efficacy and avoid resistance, Journal of Chemotherapy, 11(6):426-439 (1999).
Schiffelers, R. et al., "Liposome-encapsulated aminoglycosides in pre-clinical and clinical studies," Journal of Antimicrobial Chemotherapy, 48:333-344 (2001).
Schiffelers, R. M. et al., "Therapeutic efficacy of liposomal gentamicin in clinically relevant rat models," International Journal of Pharmaceutics, 214:103-105 (2001).
Schiffelers, R. M. et al., "In vivo synergistic interaction of liposomecoencapsulated gentamicin and ceftazidime," Journal Pharmacology Experimental Therapeutics, 298(1):369-375 (2001).
Schlegel, L. et al., "In-vitro killing activity of combinations of beta-lactam agents with aminoglycosides against penicillin-resistant pneumococci," The Journal of Antimicrobial Chemotherapy, 39(1):95-98 (1997).
Schreier, H. et al., "Pulmonary delivery of amikacin liposomes and acute liposome toxicity in the sheep," International Journal of Pharmaceutics, 87(1-3):183-193 (1992).
Schreier, H. et al., "Pulmonary delivery of liposomes," Journal of Controlled Release, 24(1):209-223 (1993).
Sermet-Gaudelus, I. et al., "Nebulized antibiotics in cystic fibrosis," Pediatric Drugs, 4(7):455-467 (2002).
Shah, S. P. et al., "Liposomal amikacin dry powder inhaler: effect of fines on in vitro performance," AAPS PharmSciTech, 5(4):e65:1-7 (2004).
Shima, K. et al., "A study of amikacin (BB-K8) on the clinical effects on the respiratory infection," Chemotherapy, 23(6):2128-2130 (1975) (with English Abstract).
Singh, P. K. et al., "Quorum-sensing signals indicate that cystic fibrosis lungs are infected with bacterial biofilms," Nature, 407:762-764 (2000).
Skubitz, K. M. et al., "Inhalational interleukin-2 liposomes for pulmonary metastases: a phase I clinical trial," Anti-Cancer Drugs, 11(7): 555-563 (2000).
Smith, A. L. et al., "Safety of aerosol tobramycin administration for 3 months to patients with cystic fibrosis," Pediatric Pulmonology, 7(4):265-271 (1989).
Smith et al. (1986). Pharmacokinetics and sputum penetration of ciprofloxacin in patients with cystic fibrosis. Antimicrobial Agents and Chemotherapy 30(4), pp. 614-616.
Stott, P. W. et al., "Characterization of complex coacervates of some tricyclic antidepressants and evaluation of their potential for enhancing transdermal flux," Journal of Controlled Release, 41(3):215-227 (1996).
Sweeney et al. (2005). Spray-freeze-dried liposomal ciprofloxacin powder for inhaled aerosol drug delivery. International Journal of Pharmaceutics 305, pp. 180-185.
Swenson, K. A. et al., "Pharmacokinetics and in vivo activity of liposome-encapsulated gentamicin," Antimicrobial Agents and Chemotherapy, 34(2)235-240 (1990).
Swenson, C. E. et al., "Liposomal aminoglycosides and TLC G-65," Aids Patient Care, pp. 290-296 (1991).
Szoka, F. Jr. et al., "Comparative properties and methods of preparation of lipid vesicles (liposomes)," Ann. Rev. Biophys. Bioeng., 9:467-508 (1980).
Tarran, R., "Regulation of Airway Surface Liquid Volume and Mucus Transport by Active Ion Transport," Proc. Am. Thorac. Soc., vol. 1, pp. 42-46, 2004.
Takamoto, M. et al., "Imipenem/cilastatin sodium alone or combined with amikacin sulfate in respiratory infections," The Japanese Journal of Antibiotics, 47(9):1131-1144 (1994) (with English Abstract).

Tateda, K. et al., "Efficacy of beta-lactam antibiotics combined with gentamicin against penicillin-resistant pneumococcal pneumonia in CBA/J mice," The Journal of Antimicrobial Chemotherapy, 43(3):367-371 (1999).
Taylor, K. M. G. et al., "The influence of liposomal encapsulation on sodium cromoglycate pharmacokinetics in man," Pharmaceutical Research, 6(7):633-636 (1989).
Ten, R. M. et al., "Interleukin-2 liposomes for primary immune deficiency using the aerosol route," International Immunopharmacology, 2(2-3):333-344 (2002).
Terzano, C. et al., "Tobramycin aerosol: could the delivery system influence the particle size and deposition in the lower airways?" Recenti. Prog. Med., 89(5):245-249 (1998) (English Abstract).
Thomas, D. A. et al., "Acute effects of liposome aerosol inhalation on pulmonary function in healthy human volunteers," Chest, 99(5):1268-1270 (1991).
Thomasin, C. et al., "Drug microencapsulation by PLA/PLGA coacervation in the light of thermodynamics. 2. Parameters determining microsphere formation," Journal of Pharmaceutical Sciences, 87(3):269-275 (1998).
Trafny, E. A. et al., "Effects of free and liposome-encapsulated antibiotics on adherence of Pseudomonas aeruginosa to collagen type I," Antimicrobial Agents and Chemotherapy, 39(12):2645-2649 (1995).
Ulrich, A. S., "Biophysical aspects of using liposomes as delivery vehicles," Bioscience Reports, 22(2):129-150 (Apr. 2002).
Van Der Straeten, M. et al., "Amikacin in the treatment of gram-negative bronchopulmonary infections," The Journal of Infectious Diseases, 134:S391-S393 (1976).
Vecellio, L., "The mesh nebuliser: a recent technical innovation for aerosol delivery," Breathe, 2(3):253-260 (2006).
Veldhuizen, R. et al., "The role of lipids in pulmonary surfactant," Biochimica et Biophysics Acta, 1408:90-108 (1998).
Vidgren, M. et al., "A study of $^{99m}$, technetium-labelled beclomethasone dipropionate dilauroylphosphatidylcholine liposome aerosol in normal volunteers," International Journal of Pharmaceutics, 115:209-216 (1995).
Vitas, A. I. et al., "Effect of composition and method of preparation of liposomes on their stability and interaction with murine monocytes infected with *Brucella abortus*," Antimicrobial Agents and Chemotherapy, 40(1):146-151 (1996).
Wang, W. et al., "Research progress in pulmonary administration of liposome," Journal of Shenyang Pharmaceutical University, 17(3):226-229 (2000).
Webb, M. S. et al., "Antibacterial Efficacy against an In Vivo *Salmonella typhimurium* Infection Model and Pharmacokinetics of a Liposomal Ciprofloxacin Formulation," Antimicrobial Agents and Chemotherapy, 42(1):45-52 (Jan. 1998).
Weber et al. (1997). Effect of nebulizer type and antibiotic concentration on device performance. Pediatric Pulmonology 23, pp. 249-260.
Wise et al. (1983). In vitro activity of Bay 09867, a new quinolone derivate compared with those of other antimicrobial agents. Antimicrobial Agents and Chemotherapy 23(4), pp. 559-564.
Westerman, E. M. et al., "Effect of nebulized colistin sulphate and colistin sulphomethate on lung function in patents with cystic fibrosis: a pilot study," Journal of Cystic Fibrosis, 3(1):23-28 (2004).
Whitehead, T. C. et al., "Kinetics and Toxicity of Liposomal and Conventional Amikacin in a Patient with Multidrug-Resistant Tuberculosis," Eur J Clin Microbiol. Infect. Dis., 17:794-797 (1998).
Wichert, B. V. et al., "Amikacin liposomes: characterization, aerosolization, and in vitro activity against *Mycobacterium avium-intracellulare* in alveolar macrophages," International Journal of Pharmaceutics, 78(13):227-235 (1992).
Wolff, R. K. et al., "Toxicologic testing of inhaled pharmaceutical aerosols," Critical Reviews in Toxicology, 23(4):343-369 (1993).
Worlitzsch, D. et al., "Effects of reduced mucus oxygen concentration in airway pseudomonas infections of cystic fibrosis patients," J. Clin. Invest., 109:317-325 (2002).

(56) References Cited

OTHER PUBLICATIONS

Xiu, L. et al., "Drug Resistant Analysis of Pseudomonas Aeruginosa in Patients with Mechanical Ventilation," Med. J. Chin. PLA, 27(6):544-545 (2002) (with English Abstract).

Yanagihara, K. et al., "Design of anti-bacterial drug and anti-Mycobacterial drug for drug delivery system," Current Pharmaceutical Design, 8:475-482 (2002).

Yim, D. et al., "The Development of Inhaled Liposome-Encapsulated Ciprofloxacin to Treat Cystic Fibrosis," Respiratory Drug Delivery, pp. 425-428 (2006).

Zeng, S. et al., "Intravitreal Pharmacokinetics of Liposome-encapsulated Amikacin in a Rabbit Model," Ophthamology, 100:1640-1644 (1993).

Zhang, J. H. et al., "A Novel Method to Prepare Liposomes Containing Amikacin," Journal Microencapsulation, 16(4):511-516 (1999).

Zhang, X. et al., "Antibacterial drug treatment of community acquired pneumonia," Chinese Journal of Respiratory and Critical Care Medicine, 4(4):258-260 (2005).

Zlatanov, Z. et al., "Gentamycin-pharmachim. Aerosol inhalation treatment of patients with chronic bronchitis," Medico Biologic Information 2, pp. 5-8 (1976).

Biller, J. A. et al., "Efficacy of Liposomal Amikacin for Inhalation (LAI) in Achieving Nontuberculous Mycobacteria (NTM) Culture Negativity in Patients Whose Lung Infection Is Refractory to Guideline-Based Therapy," Poster presented at the ATS 2015 International Conference, May 15-20, 2015, Denver, CO, USA, 1 page.

Biller, J. A. et al., "Efficacy of Liposomal Amikacin for Inhalation (LAI) in Achieving Nontuberculous Mycobacteria (NTM) Culture Negativity in Patients Whose Lung Infection Is Refractory to Guideline-Based Therapy," Abstract, D108 Diagnosis and Management of Nontuberculous Mycobacteria Infections, Poster Discussion Session, May 20, 2015, Colorado Convention Center, Am J Respir Crit Care Med 191;2015:A6295, Online Abstracts Issue, 1 page.

Winthrop, K. L. et al., "Subgroup Analyses of Baseline Demographics and Efficacy in Patents With Refractory Nontuberculous Mycobacteria (NTM) Lung Infection Treated With Liposomal Amikacin for Inhalation (LAI)," Poster presented at the ATS 2015 International Conference, May 15-20, 2015, Denver, CO, USA, 1 page.

Winthrop, K. L. et al., "Subgroup Analyses of Baseline Demographics and Efficacy in Patents With Refractory Nontuberculous Mycobacteria (NTM) Lung Infection Treated With Liposomal Amikacin for Inhalation (LAI)," Abstract, D108 Diagnosis and Management of Nontuberculous Mycobacteria Infections, Poster Discussion Session, May 20, 2015, Colorado Convention Center, Am J Respir Crit Care Med 191;2015:A6294, Online Abstracts Issue, 2 pages.

Concise explanation of relevance of Biller and Winthrop Posters and Abstracts (citations 1-4).

Extended European Search Report for European Application No. 15791964.8, dated Dec. 11, 2017, 10 pages.

Chuchalin et al., "A formulation of aerosolized tobramycin (Bramitob) in the treatment of patients with cystic fibrosis and Pseudomonas aeruginosa infection: a double-blind, placebo-controlled, multicenter study," Paediatric Drugs, 9(Suppl. 1), pp. 21-31, 2007.

Dupont et al., "A randomized placebo-controlled study of nebulized liposomal amikacin (Arikace) in the treatment of cystic fibrosis patients with chronic Pseudomonas aeruginosa lung infection," Journal of Cystic Fibrosis, 1(7):S26, Abstract 102, Jan. 2008.

Duzgunes, N. et al., "Treatment of intracellular *Mycobacterium avium* complex infection by free and liposome-encapsulated sparfloxacin," Antimicrobial Agents and Chemotherapy, 40(11):2618-2621 (Nov. 1996).

Nikolaizik et al., "A pilot study to compare tobramycin 80 mg injectable preparation with 300 mg solution for inhalation in cystic fibrosis patients," Canadian Respiratory Journal, 15(5):259-262, Jul./Aug. 2008.

Rose, S. J. et al., "Delivery of Aerosolized Liposomal Amikacin as a Novel Approach for the Treatment of Nontuberculous Mycobacteria in an Experimental Model of Pulmonary Infection," Sep. 2014, PLoS ONE 9(9): e108703. doi:10.1371/journal.pone.0108703.

\* cited by examiner

FIGURE 5
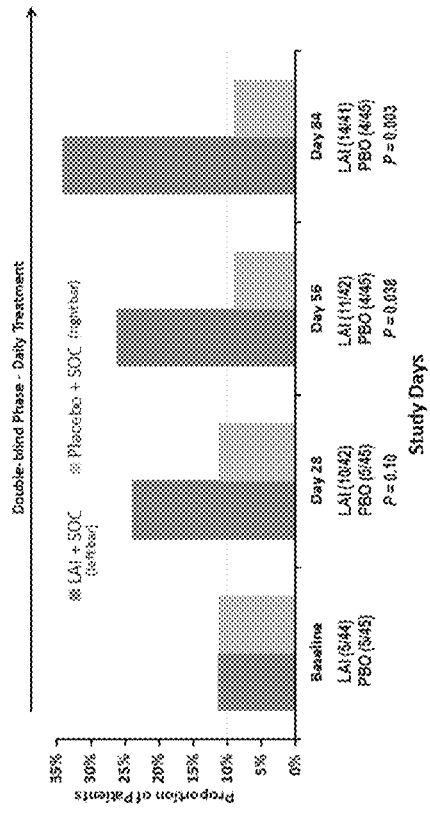
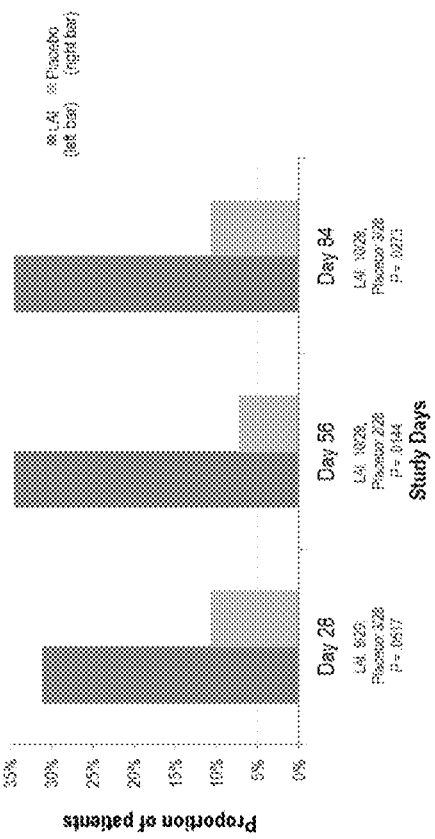

FIGURE 6

Patients with at least 1 NTM Culture Negative Result

| Treatment Arm | CF Patient | NTM Organism | Length of NTM Prior to Baseline (Months) | Prior Amikacin Use | SQS at Screening | Baseline | Day 28 | Day 56 | Day 94 | Day 112 | Day 140 | Day 168 | 28-Day Follow up |
|---|---|---|---|---|---|---|---|---|---|---|---|---|---|
| LAI | Non-CF | MAC | >24 | | 2 | | | | | | | | |
| | | | >24 | | 5 | | | | | | | | |
| | | | >24 | | 5 | | | | | | | | |
| | | | >24 | | 6 | | | | | | | | Early Term |
| | | | >12 - 24 | | 2 | | | | | | | | |
| | | | >12 - 24 | | 2 | | | | | | | | |
| | | | >12 - 24 | INH | 3 | | | | | | | | |
| | | | >12 - 24 | | 3 | | | | | | | | |
| | | | >12 - 24 | | 3 | | | | | | | | |
| | | | 6 - 12 | | 3 | | | | | | | | |
| | | M. abscessus | 6 - 12 | | 4 | | | | | | | | |
| | | MAC | 6 - 12 | | 3 | | | | | | | | |
| | | | >12 - 24 | IV | 5 | | | | | | | | Early Term |
| | CF | MAC | >12 - 24 | INH | 3 | | | | | | | | |
| | | | >24 | INH | 3 | | | | | | | | |
| | | M. abscessus | 6 - 12 | INH | 6 | | | | | | | | |
| PBO | Non-CF Patient | MAC | >24 | | 4 | | | | | | | | |
| | | | >24 | INH | 3 | | | | | | | | |
| | | | >24 | | 4 | | | | | | | | |
| | | | >12 - 24 | | 4 | | | | | | | | |
| | | | >12 - 24 | | 2 | | | | | | | | |
| | | | >12 - 24 | | 3 | | | | | | | | Early Term |
| | | | >12 - 24 | | 3 | | | | | | | | |
| | | | 6 - 12 | INH | 2 | | | | | | | | |
| | | | 6 - 12 | INH | 2 | | | | | | | | |
| | | | >24 | | 2 | | | | | | | | |
| | CF | M. abscessus | >24 | | 3 | | | | | | | | |
| | Number of patient with negative culture confirmed with no growth while being treated with LAI + SOC | | | | | | 10 | 10 | 11 | 19 | 19 | 21 | |
| | Number of patient with negative culture while being treated with PBO + SOC | | | | | | 4 | 3 | 3 | NA | NA | NA | |

*Note.* All negative cultures confirmed with no growth in liquid medium.
CF, cystic fibrosis; INH, inhalation; IV, intravenous; LAI, liposomal amikacin for inhalation; MAC, *Mycobacterium avium* complex; NA, not applicable; NTM, nontuberculous mycobacteria; PBO, placebo; SOC, standard of care; SQS, Semi-Qualitative Scale.

▓ = culture negative (LAI)
▒ = culture negative (PBO)
█ = culture negative (off treatment)

METHODS FOR TREATING PULMONARY NON-TUBERCULOUS MYCOBACTERIAL INFECTIONS

CROSS REFERENCE TO RELATED APPLICATIONS

This application claims priority from U.S. Provisional Application Ser. Nos. 61/993,439, filed May 15, 2014; 62/042,126, filed Aug. 26, 2014; 62/048,068, filed Sep. 9, 2014; and 62/056,296, filed Sep. 26, 2014, the disclosures of each of which are incorporated by reference in their entireties for all purposes.

BACKGROUND OF THE INVENTION

Certain technologies suitable for administration by inhalation employ liposomes and lipid complexes supply a prolonged therapeutic effect of drug in the lung. These technologies also provide the drug with sustained activities, and the ability to target and enhance the uptake of the drug into sites of disease.

Inhalation delivery of liposomes is complicated by their sensitivity to shear-induced stress during nebulization, which can lead to change in physical characteristics (e.g., entrapment, size). However, as long as the changes in characteristics are reproducible and meet acceptability criteria, they need not be prohibitive to pharmaceutical development.

Pulmonary infection with non-tuberculous *mycobacterium* (NTM) in the susceptible host can lead to potentially severe morbidity and even mortality among those affected. As infection rates are rising, pulmonary nontuberculous mycobacterial disease (PNTM) represents an emerging public health concern in the United States. NTM are ubiquitous in the environment. Over 80% of pulmonary NTM (PNTM) infections in the US are due to *Mycobacterium avium* complex (MAC). In addition, *M. Kansasii, M. abscessus*, and *M. fortuitum* are regularly isolated.

The prevalence of pulmonary NTM infections in the United States has more than doubled in the last 15 years. The ATS/IDSA PNTM reported 2-year period prevalence of pulmonary NTM infections is 8.6/100,000 persons. The prevalence of pulmonary NTM infections increases with age with 20.4/100,000 in those at least 50 years of age and is especially prevalent in females (median age: 66 years; female: 59%).

In the susceptible individual, pulmonary NTM infections can be serious or life threatening. Available therapies may be poorly tolerated, and may have significant adverse events. The present invention addresses this and other needs by providing methods for treating pulmonary NTM infections in patients in need thereof.

SUMMARY OF THE INVENTION

The present invention, in one aspect, provides methods for treating or providing prophylaxis against a nontuberculous mycobacterial (NTM) infection (pulmonary infection caused or due to one or more nontuberculous mycobacteria), via inhalation administration of an effective amount of a composition comprising a liposomal complexed aminoglycoside, or a pharmaceutically acceptable salt thereof, to a patient in need thereof. The patient in need of treatment, in one embodiment, is a cystic fibrosis patient, a bronchiectasis patient, suffers from asthma or suffers from chronic obstructive pulmonary disorder (COPD).

In one embodiment, the NTM infection is a pulmonary NTM infection selected from an *M. avium, M. avium* subsp. *hominissuis* (MAH), *M. abscessus, M. chelonae, M. bolletii, M. kansasii, M. ulcerans, M. avium, M. avium* complex (MAC) (*M. avium* and *M. intracellulare*), *M. conspicuum, M. kansasii, M. peregrinum, M. immunogenum, M. xenopi, M. marinum, M. malmoense, M. marinum, M. mucogenicum, M. nonchromogenicum, M. scrofulaceum, M. simiae, M. smegmatis, M. szulgai, M. terrae, M. terrae* complex, *M. haemophilum, M. genavense, M. gordonae, M. ulcerans, M. fortuitum, M. fortuitum* complex (*M. fortuitum* and *M. chelonae*) infection or a combination thereof. In a further embodiment, the NTM infection is an *M. avium* complex (MAC) (*M. avium* and *M. intracellulare*) infection. In one embodiment, the NTM infection is a pulmonary recalcitrant NTM infection.

In one embodiment, the composition comprising the liposomal complexed aminoglycoside is a dispersion (e.g., a liposomal solution or suspension). The liposomal portion of the composition comprises a lipid component that includes electrically neutral lipids. In a further embodiment, the electrically neutral lipids comprise a phosphatidylcholine and a sterol (e.g., dipalmitoylphosphatidylcholine and cholesterol). In a further embodiment, the aminoglycoside is amikacin or a pharmaceutically acceptable salt thereof. In even a further embodiment, the aminoglycoside is amikacin sulfate.

In one embodiment, the method for treating or providing prophylaxis against an NTM infection comprises administering an aerosolized pharmaceutical composition to the lungs of the patient in need thereof; wherein the aerosolized pharmaceutical composition comprises a mixture of free aminoglycoside and liposomal complexed aminoglycoside, and the lipid component of the liposome consists of electrically neutral lipids. In a further embodiment, the electrically neutral lipids comprise a phosphatidylcholine and a sterol (e.g., dipalmitoylphosphatidylcholine and cholesterol). In a further embodiment, the aminoglycoside is amikacin or a pharmaceutically acceptable salt thereof. In even a further embodiment, the aminoglycoside is amikacin sulfate.

The methods provided herein result in a change from baseline on the semi-quantitative scale for mycobacterial culture for a treated patient, and/or NTM culture conversion to negative during or after the administration period. For example, in one embodiment, the method provided herein results in the patient having an NTM culture conversion to negative after an administration period.

In one embodiment, the aminoglycoside or pharmaceutically acceptable salt thereof is amikacin, apramycin, arbekacin, astromicin, capreomycin, dibekacin, framycetin, gentamicin, hygromycin B, isepamicin, kanamycin, neomycin, netilmicin, paromomycin, rhodestreptomycin, ribostamycin, sisomicin, spectinomycin, streptomycin, tobramycin, verdamicin, a pharmaceutically acceptable salt thereof, or a combination thereof. In even a further embodiment, the aminoglycoside is amikacin. In another embodiment, the aminoglycoside is selected from an aminoglycoside set forth in Table 1, below, a pharmaceutically acceptable salt thereof, or a combination thereof.

TABLE 1

Aminoglycosides for use with the present invention

| AC4437 | dibekacin | K-4619 | sisomicin |
|---|---|---|---|
| amikacin | dactimicin | isepamicin | rhodestreptomycin |
| apramycin | etimicin | KA-5685 | sorbistin |
| arbekacin | framycetin | kanamycin | spectinomycin |

TABLE 1-continued

Aminoglycosides for use with the present invention

| | | | |
|---|---|---|---|
| astromicin | gentamicin | neomycin | sporaricin |
| bekanamycin | H107 | netilmicin | streptomycin |
| boholmycin | hygromycin | paromomycin | tobramycin |
| brulamycin | hygromycin B | plazomicin | verdamicin |
| capreomycin | inosamycin | ribostamycin | vertilmicin |

The pharmaceutical compositions provided herein in one embodiment are dispersions of liposomes (i.e., liposomal dispersions or aqueous liposomal dispersions which can be either liposomal solutions or liposomal suspensions). In one embodiment, the lipid component of the liposomes consists essentially of one or more electrically neutral lipids. In a further embodiment, the electrically neutral lipid comprises a phospholipid and a sterol. In a further embodiment, the phospholipid is dipalmitoylphosphatidylcholine (DPPC) and the sterol is cholesterol.

In one embodiment, the lipid to aminoglycoside weight ratio in the aminoglycoside pharmaceutical composition (aminoglycoside liposomal solution or suspension) is about 2:1, about 2:1 or less, about 1:1, about 1:1 or less, about 0.75:1 or less, or about 0.7:1. In another embodiment, the lipid to aminoglycoside weight ratio in the composition is from about 0.10:1 to about 1.25:1, from about 0.10:1 to about 1.0:1, from about 0.25:1 to about 1.25:1, from about 0.5:1 to about 1:1.

In one embodiment, the methods provided herein comprise administration of the liposomal aminoglycoside composition via nebulization or aerosolization. The method in this embodiment therefore entails generation of an aerosolized aminoglycoside composition. In one embodiment, upon nebulization, the aerosolized composition has an aerosol droplet size of about 1 µm to about 3.8 µm, about 1.0 µm to 4.8 µm, about 3.8 µm to about 4.8 µm, or about 4.0 µm to about 4.5 µm. In a further embodiment, the aminoglycoside is amikacin. In even a further embodiment, the amikacin is amikacin sulfate.

In one embodiment, about 70% to about 100% of the aminoglycoside present in the composition is liposomal complexed, e.g., encapsulated in a plurality of liposomes, prior to administration to the patient in need of treatment. In a further embodiment, the aminoglycoside is selected from an aminoglycoside provided in Table 1. In further embodiment, the aminoglycoside is an amikacin (e.g., as amikacin sulfate). In even a further embodiment, about 80% to about 100% of the amikacin is liposomal complexed, or about 80% to about 100% of the amikacin is encapsulated in a plurality of liposomes, prior to administration to the patient in need of treatment. In another embodiment, prior to administration to the patient in need of treatment (i.e., prior to nebulization), about 80% to about 100%, about 80% to about 99%, about 90% to about 100%, 90% to about 99%, or about 95% to about 99% of the aminoglycoside present in the composition is liposomal complexed.

In one embodiment, the percent liposomal complexed (also referred to herein as "liposomal associated") aminoglycoside post-nebulization is from about 50% to about 80%, from about 50% to about 75%, from about 50% to about 70%, from about 55% to about 75%, or from about 60% to about 70%. In a further embodiment, the aminoglycoside is selected from an aminoglycoside provided in Table 1. In a further embodiment, the aminoglycoside is amikacin. In even a further embodiment, the amikacin is amikacin sulfate. In one embodiment, the aerosolized composition (i.e., post nebulization) comprises from about 65% to about 75% liposomal complexed aminoglycoside and from about 25% to about 35% free aminoglycoside. In a further embodiment, the aminoglycoside is amikacin. In even a further embodiment, the amikacin is amikacin sulfate.

In one embodiment, the pulmonary infection treated by the methods provided herein is a *Mycobacterium abscessus* pulmonary infection or a *Mycobacterium avium* complex pulmonary infection. In one or more of the preceding embodiments, the patient is a cystic fibrosis patient, a bronchiectasis patient, an asthma patient or a COPD patient.

In one embodiment, a patient with cystic fibrosis is treated for a pulmonary infection with one of the compositions or systems provided herein. In a further embodiment, the pulmonary infection is caused by *Mycobacterium abscessus* or *Mycobacterium avium* complex.

In one embodiment, the concentration of the aminoglycoside in the liposomal aminoglycoside composition is about 50 mg/mL or greater. In a further embodiment, the concentration of the aminoglycoside in the liposomal complexed aminoglycoside is about 60 mg/mL or greater. In a further embodiment, the concentration of the aminoglycoside in the liposomal complexed aminoglycoside is about 70 mg/mL or greater, for example about 70 mg/mL to about 75 mg/mL. In a further embodiment, the aminoglycoside is selected from an aminoglycoside provided in Table 1. In even a further embodiment, the aminoglycoside is amikacin (e.g., amikacin sulfate).

BRIEF DESCRIPTION OF THE FIGURES

FIG. 5 (top) is a bar graph showing the proportion of patients with NTM culture conversion to negative at various time points during the randomized, double-blind, placebo controlled study (modified intent to treat population). FIG. 5 (bottom) is a bar graph showing the proportion of MAC patients with NTM culture conversion to negative at various time points.

FIG. 6 shows patients with at least 1 NTM culture negative result at various time points during the randomized, double-blind, placebo controlled study.

FIG. 8 (bottom) is a graph showing the mean change from baseline to Days 84 and 168 in distance walked (meters) in the 6MWT in patients with culture conversion to negative (≥3 negative cultures) vs. those without culture conversion to negative (last observation carried forward-modified intent to treat population).

DETAILED DESCRIPTION OF THE INVENTION

Figure 1:
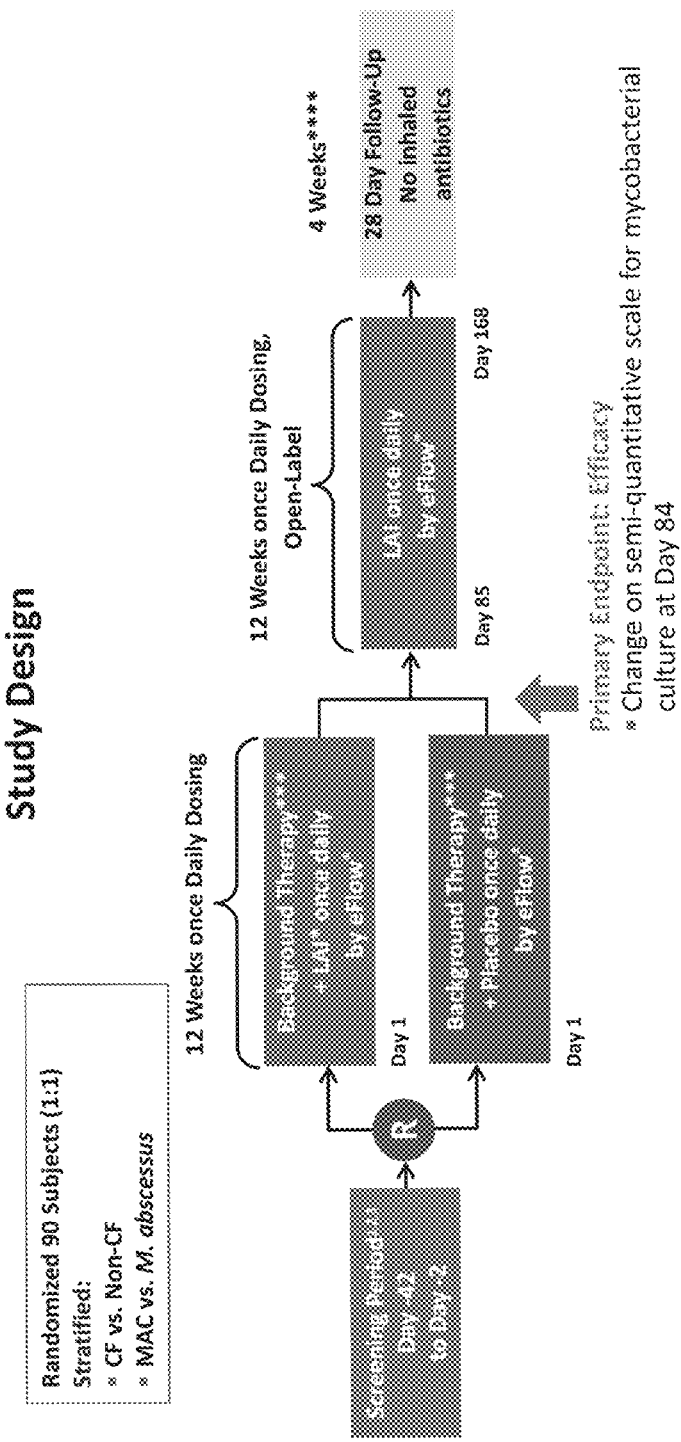
FIG. 1 shows the study design for a randomized, double-blind, placebo controlled study of liposomal complexed amikacin in patients with recalcitrant nontuberculous mycobacterial (NTM) lung infection, described in Example 1.

The invention described herein is directed, in part, to methods for treating a pulmonary infection in a patient in need thereof, e.g., administering an aminoglycoside pharmaceutical composition to the lungs of the patient, for example, via nebulization.

The term "about," as used herein, refers to plus or minus ten percent of the object that "about" modifies.

The term "treating" includes: (1) preventing or delaying the appearance of clinical symptoms of the state, disorder or condition developing in the subject that may be afflicted with or predisposed to the state, disorder or condition but does not yet experience or display clinical or subclinical symptoms of the state, disorder or condition; (2) inhibiting the state, disorder or condition (i.e., arresting, reducing or delaying the development of the disease, or a relapse thereof in case of maintenance treatment, of at least one clinical or subclinical symptom thereof); and/or (3) relieving the condition (i.e., causing regression of the state, disorder or condition or at least one of its clinical or subclinical symptoms). The benefit to a subject to be treated is either statistically significant or at least perceptible to the subject or to the physician.

"Prophylaxis," as used herein, can mean complete prevention of an infection or disease, or prevention of the development of symptoms of that infection or disease; a delay in the onset of an infection or disease or its symptoms; or a decrease in the severity of a subsequently developed infection or disease or its symptoms.

The term "antibacterial" is art-recognized and refers to the ability of the compounds of the present invention to prevent, inhibit or destroy the growth of microbes of bacteria. Examples of bacteria are provided above.

The term "antimicrobial" is art-recognized and refers to the ability of the aminoglycoside compounds of the present invention to prevent, inhibit, delay or destroy the growth of microbes such as bacteria, fungi, protozoa and viruses.

"Effective amount" means an amount of an aminoglycoside (e.g., amikacin) used in the present invention sufficient to result in the desired therapeutic response. The effective amount of the composition provided herein comprises both free and liposomal complexed aminoglycoside. For example, the liposomal complexed aminoglycoside, in one embodiment, comprises aminoglycoside encapsulated in a liposome, or complexed with a liposome, or a combination thereof.

"Liposomal dispersion" refers to a solution or suspension comprising a plurality of liposomes.

An "aerosol," as used herein, is a gaseous suspension of liquid particles. The aerosol provided herein comprises particles of the liposomal dispersion.

A "nebulizer" or an "aerosol generator" is a device that converts a liquid into an aerosol of a size that can be inhaled into the respiratory tract. Pneumonic, ultrasonic, electronic nebulizers, e.g., passive electronic mesh nebulizers, active electronic mesh nebulizers and vibrating mesh nebulizers are amenable for use with the invention if the particular nebulizer emits an aerosol with the required properties, and at the required output rate.

The process of pneumatically converting a bulk liquid into small droplets is called atomization. The operation of a pneumatic nebulizer requires a pressurized gas supply as the driving force for liquid atomization. Ultrasonic nebulizers use electricity introduced by a piezoelectric element in the liquid reservoir to convert a liquid into respirable droplets. Various types of nebulizers are described in Respiratory Care, Vol. 45, No. 6, pp. 609-622 (2000), the disclosure of which is incorporated herein by reference in its entirety. The terms "nebulizer" and "aerosol generator" are used interchangeably throughout the specification. "Inhalation device," "inhalation system" and "atomizer" are also used in the literature interchangeably with the terms "nebulizer" and "aerosol generator."

"Mass median diameter" or "MMD" is determined by laser diffraction or impactor measurements, and is the average particle diameter by mass.

"Mass median aerodynamic diameter" or "MMAD" is normalized regarding the aerodynamic separation of aqua aerosol droplets and is determined impactor measurements, e.g., the Anderson Cascade Impactor (ACI) or the Next Generation Impactor (NGI). The gas flow rate, in one embodiment, is 28 Liter per minute by the Anderson Cascade Impactor (ACI) and 15 Liter per minute by the Next Generation Impactor (NGI). "Geometric standard deviation" or "GSD" is a measure of the spread of an aerodynamic particle size distribution.

Nontuberculous mycobacteria are organisms found in the soil and water that can cause serious lung disease in susceptible individuals, for which there are currently limited effective treatments and no approved therapies. The prevalence of NTM disease is reported to be increasing, and according to reports from the American Thoracic Society is believed to be greater than that of tuberculosis in the U.S. According to the National Center for Biotechnology Information, epidemiological studies show that presence of NTM infection is increasing in developing countries, perhaps because of the implementation of tap water. Women with characteristic phenotype are believed to be at higher risk of acquiring NTM infection along with patients with defects on cystic fibrosis transmembrane conductance regulators. Generally, high risk groups with NTM lung disease for increased morbidity and mortality are those with cavitary lesions, low BMI, advanced age, and a high comorbidity index.

NTM lung disease is often a chronic condition that can lead to progressive inflammation and lung damage, and is characterized by bronchiectasis and cavitary disease. NTM infections often require lengthy hospital stays for medical management. Treatment usually involves multidrug regimens that can be poorly tolerated and have limited effectiveness, especially in patients with severe disease or in those who have failed prior treatment attempts. According to a company-sponsored patient chart study conducted by Clarity Pharma Research, approximately 50,000 patients suffering from NTM lung disease visited physician offices in the U.S. during 2011.

Management of pulmonary disease caused by nontuberculous mycobacteria (NTM) infection includes lengthy multidrug regimens, which are often associated with drug toxicity and suboptimal outcomes. Achieving NTM culture negativity is one of the objectives of treatment and represents the most clinically important microbiologic endpoint in patients with NTM lung infection.

In one aspect, the present invention provides methods for treating a pulmonary nontuberculous mycobacterial (NTM) infection in a patient in need thereof. The method in one embodiment comprises administration to the patient a composition comprising a liposomal complexed aminoglycoside, or a pharmaceutically acceptable salt thereof for an administration period. The liposomal complexed aminoglycoside, in one embodiment, comprises the aminoglycoside or pharmaceutically acceptable salt thereof encapsulated in a plurality of liposomes. The plurality of liposomes in one embodiment, include a lipid component that consists of neutral lipids. In one embodiment, the neutral lipids comprise a phospholipid and a sterol. In a further embodiment, the phospholipid is a phosphatidylcholine. In even a further embodiment, the phosphatidylcholine is dipalmitoylphosphatidylcholine (DPPC). In even a further embodiment, the sterol is cholesterol. In one embodiment, the nontuberculous mycobacterial lung infection is a recalcitrant nontuberculous mycobacterial lung infection. The patient, in one embodiment, exhibits an increased number of meters walked in the 6MWT, as compared to prior to treatment and/or an NTM culture conversion to negative, during the administration period or after the administration period.

The therapeutic response can be any response that a user (e.g., a clinician) will recognize as an effective response to the therapy. The therapeutic response will generally be a reduction, inhibition, delay or prevention in growth of or reproduction of one or more NTM, or the killing of one or more NTM. A therapeutic response may also be reflected in an improvement in pulmonary function, for example forced expiratory volume in one second ($FEV_1$). In one embodiment, where a patient is treated for an NTM lung infection, the therapeutic response is measured as the change from baseline on the full semi quantitative scale for mycobacterial culture or an improvement in the distance walked in the 6 minute walk test (6MWT). It is further within the skill of one of ordinary skill in the art to determine appropriate treatment duration, appropriate doses, and any potential combination treatments, based upon an evaluation of therapeutic response.

The NTM lung infection treatable by the methods and compositions described herein, in one embodiment, is *M. avium*, *M. avium* subsp. *hominissuis* (MAH), *M. abscessus*, *M. chelonae*, *M. bolletii*, *M. kansasii*, *M. ulcerans*, *M. avium*, *M. avium* complex (MAC) (*M. avium* and *M. intracellulare*), *M. conspicuum*, *M. kansasii*, *M. peregrinum*, *M. immunogenum*, *M. xenopi*, *M. marinum*, *M. malmoense*, *M. marinum*, *M. mucogenicum*, *M. nonchromogenicum*, *M. scrofulaceum*, *M. simiae*, *M. smegmatis*, *M. szulgai*, *M. terrae*, *M. terrae* complex, *M. haemophilum*, *M. genavense*, *M. asiaticum*, *M. shimoidei*, *M. gordonae*, *M. nonchromogenicum*, *M. triplex*, *M. lentiflavum*, *M. celatum*, *M. fortuitum*, *M. fortuitum* complex (*M. fortuitum* and *M. chelonae*) or a combination thereof. In a further embodiment, the nontuberculous mycobacterial lung infection is *M. avium* complex (MAC) (*M. avium* and *M. intracellulare*), *M. abscessus* or *M. avium*. In a further embodiment, the *M. avium* infection is *M. avium* subsp. *hominissuis*. In one embodiment, the nontuberculous mycobacterial lung infection is *M. avium* complex (MAC) (*M. avium* and *M. intracellulare*). In another embodiment, the NTM lung infection is a recalcitrant nontuberculous mycobacterial lung infection.

As described throughout, the compositions and systems described herein are used to treat an infection caused by a nontuberculous *mycobacterium* (NTM). In one embodiment, the compositions and systems described herein are used to treat an infection caused by *Mycobacterium abscessus*, *Mycobacterium avium* or *M. avium* complex. In even a further embodiment, the *Mycobacterium avium* infection is *Mycobacterium avium* subsp. *hominissuis*.

In one embodiment, a patient is treated for a *Mycobacterium abscessus*, *M. kansasii*, *M. abscessus*, *M. fortuitum*, *Mycobacterium avium* or a *M. avium* complex (MAC) lung infection via inhalation delivery of a liposomal aminoglycoside composition. In a further embodiment, the aminoglycoside is amikacin sulfate and is administered once per day for in a single dosing session. In even a further embodiment, the NTM lung infection is MAC.

The NTM lung infection, in one embodiment, is associated with cavitary lesions. In one embodiment, the NTM lung infection is a nodular infection. In a further embodiment, the NTM lung infection is a nodular infection with minimal cavitary lesions.

In one embodiment, the aminoglycoside or pharmaceutically acceptable salt thereof, administered via the methods described herein, is selected from amikacin, apramycin, arbekacin, astromicin, capreomycin, dibekacin, framycetin, gentamicin, hygromycin B, isepamicin, kanamycin, neomycin, netilmicin, paromomycin, rhodestreptomycin, ribostamycin, sisomicin, spectinomycin, streptomycin, tobramycin, verdamicin, or a pharmaceutically acceptable salt thereof. In a further embodiment, the aminoglycoside is amikacin. In even a further embodiment, the amikacin is amikacin sulfate. In another embodiment, the aminoglycoside is selected from an aminoglycoside set forth in Table 2, below, a pharmaceutically acceptable salt thereof, or a combination thereof. For example, a a pharmaceutically acceptable salt such as a sulfate salt of one or more of the aminoglycosides set forth in Table 2 can be formulated in a liposomal composition and administered to a patient in need of NTM treatment, e.g., via pulmonary delivery by a nebulizer.

TABLE 2

Aminoglycosides for use with the present invention

| | | | |
|---|---|---|---|
| AC4437 | dibekacin | K-4619 | sisomicin |
| amikacin | dactimicin | isepamicin | rhodestreptomycin |
| arbekacin | etimicin | KA-5685 | sorbistin |
| apramycin | framycetin | kanamycin | spectinomycin |
| astromicin | gentamicin | neomycin | sporaricin |
| bekanamycin | H107 | netilmicin | streptomycin |
| boholmycin | hygromycin | paromomycin | tobramycin |
| brulamycin | hygromycin B | plazomicin | verdamicin |
| capreomycin | inosamycin | ribostamycin | vertilmicin |

In one embodiment, a pharmaceutical composition comprises a combination of aminoglycosides, or pharmaceutically acceptable salts thereof, e.g., a combination of two or more aminoglycosides, or pharmaceutically acceptable salts thereof, as set forth in Table 2. In one embodiment, the composition comprising the liposomal complexed aminoglycoside comprises from 1 to about 5 aminoglycosides, or pharmaceutically acceptable salts thereof. In an In another embodiment, the composition comprising the liposomal complexed aminoglycoside comprises at least 1, at least 2, at least 3, at least 4, at least 5, or at least 6, of the aminoglycosides set forth in table 2 (or pharmaceutically acceptable salts of the aminoglycosides. In another embodiment, a pharmaceutical composition comprises between 1 and 4 aminoglycosides, or pharmaceutically acceptable salts thereof. In a further embodiment, the combination comprises amikacin, e.g., as amikacin sulfate.

In one embodiment, the aminoglycoside is an aminoglycoside free base, or its salt, solvate, or other non-covalent derivative. In a further embodiment, the aminoglycoside is amikacin. Included as suitable aminoglycosides used in the drug compositions of the present invention are pharmaceutically acceptable addition salts and complexes of drugs. In cases where the compounds may have one or more chiral centers, unless specified, the present invention comprises each unique racemic compound, as well as each unique nonracemic compound. In cases in which the active agents have unsaturated carbon-carbon double bonds, both the cis (Z) and trans (E) isomers are within the scope of this invention. In cases where the active agents exist in tautomeric forms, such as keto-enol tautomers, each tautomeric form is contemplated as being included within the invention. Amikacin, in one embodiment, is present in the pharmaceutical composition as amikacin base, or amikacin salt, for example, amikacin sulfate or amikacin disulfate. In one embodiment, a combination of one or more of the above aminoglycosides is used in the compositions, systems and methods described herein.

The present invention provides in one aspect, a method for treating or providing prophylaxis against a pulmonary NTM infection. Treatment is achieved via delivery of a composition comprising a liposomal aminoglycoside composition by inhalation via nebulization of the composition. In one embodiment, the composition comprises an aminoglycoside encapsulated in a plurality of liposomes, e.g., an aminoglycoside selected from one or more of the aminoglycosides of Tables 1 and/or 2, or a pharmaceutically acceptable salt thereof.

The pharmaceutical composition, as provided herein, is a liposomal dispersion comprising an aminoglycoside complexed to a liposome, e.g., an aminoglycoside encapsulated in a plurality of liposomes. The pharmaceutical composition is a dispersion comprising a "liposomal complexed aminoglycoside" or an "aminoglycoside encapsulated in a liposome." A "liposomal complexed aminoglycoside" includes embodiments where the aminoglycoside (or combination of aminoglycosides) is encapsulated in a liposome, and includes any form of aminoglycoside composition where at least about 1% by weight of the aminoglycoside is associated with the liposome either as part of a complex with a liposome, or as a liposome where the aminoglycoside may be in the aqueous phase or the hydrophobic bilayer phase or at the interfacial headgroup region of the liposomal bilayer.

In one embodiment, the lipid component of the liposome or plurality of liposomes comprises electrically neutral lipids, positively charged lipids, negatively charged lipids, or a combination thereof. In another embodiment, the lipid component comprises electrically neutral lipids. In a further embodiment, the lipid component consists essentially of electrically neutral lipids. In even a further embodiment, the electrically neutral lipids comprise a sterol and a phospholipid. In even a further embodiment the sterol is cholesterol and the phospholipid is a neutral phosphatidylcholine. In one embodiment, the phosphatidylcholine is dipalmitoylphosphatidylcholine (DPPC).

As provided above, liposomal complexed aminoglycoside embodiments include embodiments where the aminoglycoside or pharmaceutically acceptable salt thereof is encapsulated in a plurality of liposomes. In addition, the liposomal complexed aminoglycoside describes any composition, solution or suspension where at least about 1% by weight of the aminoglycoside is associated with the lipid either as part of a complex with the liposome, or as a liposome where the aminoglycoside may be in the aqueous phase or the hydrophobic bilayer phase or at the interfacial headgroup region of the liposomal bilayer. In one embodiment, prior to nebulization, at least about 5%, at least about 10%, at least about 20%, at least about 25%, at least about 50%, at least about 75%, at least about 80%, at least about 85%, at least about 90% or at least about 95% of the aminoglycoside in the composition is so associated. Association, in one embodiment, is measured by separation through a filter where lipid and lipid-associated drug is retained (i.e., in the retentate) and free drug is in the filtrate.

The methods provided herein comprise administering to a patient in need thereof a composition comprising an aminoglycoside or pharmaceutically acceptable salt thereof encapsulated in a plurality of liposomes. One or more lipids can be used to form the plurality of liposomes. In one embodiment, the one or more lipids is synthetic, semi-synthetic or a naturally-occurring lipid, including a phospholipid, tocopherol, sterol, fatty acid, negatively-charged lipid, cationic lipid or a combination thereof. In one embodiment, the lipid component of the plurality of liposomes consists of electrically neutral lipids. In a further embodiment, the lipid component comprises DPPC and cholesterol.

In one embodiment, at least one phospholipid is present in the plurality of liposomes. The phospholipid, in one embodiment, is electrically net neutral. In one embodiment, the phospholipid is a phosphatidylcholine (PC), phosphatidylglycerol (PG), phosphatidylinositol (PI), phosphatidylserine (PS), phosphatidylethanolamine (PE), and phosphatidic acid (PA); the soya counterparts, soy phosphatidylcholine (SPC); SPG, SPS, SPI, SPE, and SPA; the hydrogenated egg and soya counterparts (e.g., HEPC, HSPC), phospholipids made up of ester linkages of fatty acids in the 2 and 3 of glycerol positions containing chains of 12 to 26 carbon atoms and different head groups in the 1 position of glycerol that include choline, glycerol, inositol, serine, ethanolamine, as well as the corresponding phosphatidic acids. The carbon chains on these fatty acids can be saturated or unsaturated, and the phospholipid may be made up of fatty acids of different chain lengths and different degrees of unsaturation.

In one embodiment, the lipid component of the plurality of liposomes includes dipalmitoylphosphatidylcholine (DPPC), a major constituent of naturally-occurring lung surfactant. In one embodiment, the lipid component of the plurality of liposomes comprises DPPC and cholesterol, or consists essentially of DPPC and cholesterol, or consists of DPPC and cholesterol. In a further embodiment, the DPPC and cholesterol have a mole ratio in the range of from about 19:1 to about 1:1, or about 9:1 to about 1:1, or about 4:1 to about 1:1, or about 2:1 to about 1:1, or about 1.86:1 to about 1:1. In even a further embodiment, the DPPC and cholesterol have a mole ratio of about 2:1 or about 1:1.

Other examples of lipids for use with the methods and compositions described herein include, but are not limited to, dimyristoylphosphatidycholine (DMPC), dimyristoylphosphatidylglycerol (DMPG), dipalmitoylphosphatidcholine (DPPC), dipalmitoylphosphatidylglycerol (DPPG), distearoylphosphatidylcholine (DSPC), distearoylphosphatidylglycerol (DSPG), dioleylphosphatidyl-ethanolamine (DOPE), mixed phospholipids such as palmitoylstearoylphosphatidyl-choline (PSPC), and single acylated phospholipids, for example, mono-oleoyl-phosphatidylethanolamine (MOPE).

In one embodiment, the lipid component of the plurality of liposomes comprises a sterol. In a further embodiment, the at least one lipid component comprises a sterol and a phospholipid, or consists essentially of a sterol and a phospholipid, or consists of a sterol and a phospholipid (e.g., a neutral phosphatidylcholine such as DPPC). Sterols for use with the invention include, but are not limited to, cholesterol, esters of cholesterol including cholesterol hemi-succinate, salts of cholesterol including cholesterol hydrogen sulfate and cholesterol sulfate, ergosterol, esters of ergosterol including ergosterol hemi-succinate, salts of ergosterol including ergosterol hydrogen sulfate and ergosterol sulfate, lanosterol, esters of lanosterol including lanosterol hemi-succinate, salts of lanosterol including lanosterol hydrogen sulfate, lanosterol sulfate and tocopherols. The tocopherols can include tocopherols, esters of tocopherols including tocopherol hemi-succinates, salts of tocopherols including tocopherol hydrogen sulfates and tocopherol sulfates. The term "sterol compound" includes sterols, tocopherols and the like.

In one embodiment, at least one cationic lipid (positively charged lipid) is provided in the lipid component of the plurality of liposomes, present in the liposomal aminoglycoside compositions described herein, for use in the method of treating an NTM pulmonary infection in a patient in need thereof. Cationic lipids amendable for use with the present invention include but are not limited to ammonium salts of fatty acids, pholipids and glycerides. The fatty acids include fatty acids of carbon chain lengths of 12 to 26 carbon atoms that are either saturated or unsaturated. Some specific examples include, but are not limited to, myristylamine, palmitylamine, laurylamine and stearylamine, dilauroyl ethylphosphocholine (DLEP), dimyristoyl ethylphosphocholine (DMEP), dipalmitoyl ethylphosphocholine (DPEP) and distearoyl ethylphosphocholine (DSEP), N-(2,3-di-(9-(Z)-octadecenyloxy)-prop-1-yl-N,N,N-trimethylammonium chloride (DOTMA), 1,2-bis(oleoyloxy)-3-(trimethylammonio) propane (DOTAP), and combinations thereof.

In one embodiment, at least one anionic lipid (negatively charged lipid) is provided in the lipid component of the plurality of liposomes, present in the liposomal aminoglycoside compositions described herein, for use in the method of treating an NTM pulmonary infection in a patient in need thereof. The negatively-charged lipids which can be used include phosphatidyl-glycerols (PGs), phosphatidic acids (PAs), phosphatidylinositols (PIs) and the phosphatidyl serines (PSs). Examples include but are not limited to DMPG, DPPG, DSPG, DMPA, DPPA, DSPA, DMPI, DPPI, DSPI, DMPS, DPPS, DSPS and combinations thereof.

Without wishing to be bound by theory, phosphatidylcholines, such as DPPC, aid in the uptake of the aminoglycoside agent by the cells in the lung (e.g., the alveolar macrophages) and helps to maintain the aminoglycoside agent in the lung. The negatively charged lipids such as the PGs, PAs, PSs and PIs, in addition to reducing particle aggregation, are thought to play a role in the sustained activity characteristics of the inhalation composition as well as in the transport of the composition across the lung (transcytosis) for systemic uptake. The sterol compounds, without wishing to be bound by theory, are thought to affect the release characteristics of the composition.

Liposomes are completely closed lipid bilayer membranes containing an entrapped aqueous volume. Liposomes may be unilamellar vesicles (possessing a single membrane bilayer) or multilamellar vesicles (onion-like structures characterized by multiple membrane bilayers, each separated from the next by an aqueous layer) or a combination thereof. The bilayer is composed of two lipid monolayers having a hydrophobic "tail" region and a hydrophilic "head" region. The structure of the membrane bilayer is such that the hydrophobic (nonpolar) "tails" of the lipid monolayers orient toward the center of the bilayer while the hydrophilic "heads" orient towards the aqueous phase.

The lipid to aminoglycoside ratio by weight (weight ratios are also referred to herein as "lipid:aminoglycoside") in the pharmaceutical composition provided herein, in one embodiment, is 3:1 or less, 2.5:1.0 or less, 2:1 or less, 1.5:1 or less, 1:1 or less or 0.75:1 or less. In one embodiment, the lipid:aminoglycoside weight ratio in the composition provided herein is 0.7:1.0 or about 0.7:1.0 by weight. In another embodiment, the L:D ratio in liposomes provided herein is 0.75:1 or less (by weight). In one embodiment, the lipid:aminoglycoside weight ratio (lipid to aminoglycoside weight ratio) is from about 0.10:1.0 to about 1.25:1.0, from about 0.25:1.0 to about 1.25:1.0, from about 0.50:1.0 to about 1.25:1.0 or from about 0.6:1 to about 1.25:1.0. In another embodiment, the lipid to aminoglycoside weight ratio is from about 0.1:1.0 to about 1.0:1.0, or from about 0.25:1.0 to about 1.0:1.0 or about 0.5:1 to 1:1.0.

The lipid to aminoglycoside weight ratio in the composition provided herein in another embodiment, is less than 3:1, less than 2.5:1.0, less than 2.0:1.0, less than 1.5:1.0, or less than 1.0:1.0. In a further embodiment, the lipid to aminoglycoside weight ratio is about 0.7:1.0 or less or about 0.7:1.0. In yet another embodiment, the lipid to aminoglycoside weight ratio is from about 0.5:1.0 to about 0.8:1.0.

In order to minimize dose volume and reduce patient dosing time, in one embodiment, it is important that liposomal entrapment of the aminoglycoside (e.g., the aminoglycoside amikacin) be highly efficient and that the lipid to aminoglycoside weight ratio be at as low a value as possible and/or practical while keeping the liposomes small enough to penetrate patient mucus and biofilms. In one embodiment, the L aminoglycoside weight ratio in the composition provided herein, i.e., the composition comprising an aminoglycoside encapsulated in a plurality of liposomes is 0.7:1.0, about 0.7:1.0 from about 0.5:1.0 to about 0.8:1.0 or from about 0.6:1.0 to about 0.8:1.0. In a further embodiment, the liposomes provided herein are small enough to effectively penetrate a bacterial biofilm. In even a further embodiment, the mean diameter of the plurality of liposomes, as measured by light scattering is from about 200 nm to about 400 nm, or from about 250 nm to about 400 nm, or from about 250 nm to about 300 nm, or from about 200 nm to about 300 nm. In even a further embodiment, the mean diameter of the plurality of liposomes, as measured by light scattering is from about 260 to about 280 nm.

In one embodiment, the liposomal compositions described herein are manufactured by one of the methods set forth in U.S. Patent Application Publication No. 2013/0330400 or U.S. Pat. No. 7,718,189, each of which is incorporated by reference in its entirety for all purposes. Liposomes can be produced by a variety of methods (see, e.g., Cullis et al. (1987)). In one embodiment, one or more of the methods described in U.S. Patent Application Publication No. 2008/0089927 are used herein to produce the aminoglycoside encapsulated lipid compositions (liposomal dispersion). The disclosure of U.S. Patent Application Publication No. 2008/0089927 is incorporated by reference in its entirety for all purposes. For example, in one embodiment, at least one lipid and an aminoglycoside are mixed with a coacervate (i.e., a separate liquid phase) to form the liposome composition. The coacervate can be formed to prior to mixing with the lipid, during mixing with the lipid or after mixing with the lipid. Additionally, the coacervate can be a coacervate of the active agent.

In one embodiment, the liposomal dispersion is formed by dissolving one or more lipids in an organic solvent forming a lipid solution, and the aminoglycoside coacervate forms from mixing an aqueous solution of the aminoglycoside with the lipid solution. In a further embodiment, the organic solvent is ethanol. In even a further embodiment, the lipid solution comprises a phospholipid and a sterol, e.g., DPPC and cholesterol.

In one embodiment, liposomes are produces by sonication, extrusion, homogenization, swelling, electroformation, inverted emulsion or a reverse evaporation method. Bangham's procedure (J. Mol. Biol. (1965)) produces ordinary multilamellar vesicles (MLVs). Lenk et al. (U.S. Pat. Nos. 4,522,803, 5,030,453 and 5,169,637), Fountain et al. (U.S. Pat. No. 4,588,578) and Cullis et al. (U.S. Pat. No. 4,975,282) disclose methods for producing multilamellar liposomes having substantially equal interlamellar solute distribution in each of their aqueous compartments. Paphadjopoulos et al., U.S. Pat. No. 4,235,871, discloses preparation of oligolamellar liposomes by reverse phase evaporation. Each of the methods is amenable for use with the present invention.

Unilamellar vesicles can be produced from MLVs by a number of techniques, for example, the extrusion techniques of U.S. Pat. No. 5,008,050 and U.S. Pat. No. 5,059,421. Sonication and homogenization cab be so used to produce smaller unilamellar liposomes from larger liposomes (see, for example, Paphadjopoulos et al. (1968); Deamer and Uster (1983); and Chapman et al. (1968)).

The liposome preparation of Bangham et al. (J. Mol. Biol. 13, 1965, pp. 238-252) involves suspending phospholipids in an organic solvent which is then evaporated to dryness leaving a phospholipid film on the reaction vessel. Next, an appropriate amount of aqueous phase is added, the mixture is allowed to "swell," and the resulting liposomes which consist of multilamellar vesicles (MLVs) are dispersed by mechanical means. This preparation provides the basis for the development of the small sonicated unilamellar vesicles described by Papahadjopoulos et al. (Biochim. Biophys. Acta. 135, 1967, pp. 624-638), and large unilamellar vesicles.

Techniques for producing large unilamellar vesicles (LUVs), such as, reverse phase evaporation, infusion procedures, and detergent dilution, can be used to produce liposomes for use in the pharmaceutical compositions provided herein. A review of these and other methods for producing liposomes may be found in the text Liposomes, Marc Ostro, ed., Marcel Dekker, Inc., New York, 1983, Chapter 1, which is incorporated herein by reference. See also Szoka, Jr. et al., (Ann. Rev. Biophys. Bioeng. 9, 1980, p. 467), which is also incorporated herein by reference in its entirety for all purposes.

Other techniques for making liposomes include those that form reverse-phase evaporation vesicles (REV), U.S. Pat. No. 4,235,871. Another class of liposomes that may be used is characterized as having substantially equal lamellar solute distribution. This class of liposomes is denominated as stable plurilamellar vesicles (SPLV) as defined in U.S. Pat. No. 4,522,803, and includes monophasic vesicles as described in U.S. Pat. No. 4,588,578, and frozen and thawed multilamellar vesicles (FATMLV) as described above.

A variety of sterols and their water soluble derivatives such as cholesterol hemisuccinate have been used to form liposomes; see, e.g., U.S. Pat. No. 4,721,612. Mayhew et al., PCT Publication No. WO 85/00968, described a method for reducing the toxicity of drugs by encapsulating them in liposomes comprising alpha-tocopherol and certain derivatives thereof. Also, a variety of tocopherols and their water soluble derivatives have been used to form liposomes, see PCT Publication No. 87/02219.

The pharmaceutical composition, in one embodiment, pre-nebulization, comprises liposomes with a mean diameter, that is measured by a light scattering method, of approximately 0.01 microns to approximately 3.0 microns, for example, in the range about 0.2 to about 1.0 microns. In one embodiment, the mean diameter of the liposomes in the composition is about 200 nm to about 300 nm, about 210 nm to about 290 nm, about 220 nm to about 280 nm, about 230 nm to about 280 nm, about 240 nm to about 280 nm, about 250 nm to about 280 nm or about 260 nm to about 280 nm. The sustained activity profile of the liposomal product can be regulated by the nature of the lipid membrane and by inclusion of other excipients in the composition.

In one embodiment, the method described herein comprises administering a liposomal complexed aminoglycoside composition, e.g., a liposomal complexed amikacin (e.g., amikacin sulfate) composition to a patient in need thereof via inhalation, for example, via a nebulizer. In one embodiment, the amount of aminoglycoside provided in the composition is about 450 mg, about 500 mg, about 550 mg, about 560 mg, about 570 mg, about 580 mg, about 590 mg, about 600 mg or about 610 mg. In another embodiment, the amount of aminoglycoside provided in the composition is from about 500 mg to about 600 mg, or from about 500 mg to about 650 mg, or from about 525 mg to about 625 mg, or from about 550 mg to about 600 mg. In one embodiment, the amount of aminoglycoside administered to the subject is about 560 mg and is provided in an 8 mL composition. In one embodiment, the amount of aminoglycoside administered to the subject is about 590 mg and is provided in an 8 mL composition. In one embodiment, the amount of aminoglycoside administered to the subject is about 600 mg and is provided in an 8 mL composition. In one embodiment, the aminoglycoside is amikacin and the amount of amikacin provided in the composition is about 450 mg, about 500 mg, about 550 mg, about 560 mg, about 570 mg, about 580 mg, about 590 mg, about 600 mg or about 610 mg. In another embodiment, the aminoglycoside is amikacin and the amount of amikacin provided in the composition is from about 500 mg to about 650 mg, or from about 525 mg to about 625 mg, or from about 550 mg to about 600 mg. In one embodiment, the aminoglycoside is amikacin and the amount of amikacin administered to the subject is about 560 mg, and is provided in an 8 mL composition. In one embodiment, the aminoglycoside is amikacin and the amount of amikacin administered to the subject is about 590 mg, and is provided in an 8 mL composition. In one embodiment, the aminoglycoside is amikacin and the amount of aminoglycoside administered to the subject is about 600 mg and is provided in an 8 mL composition.

In one embodiment, the methods described herein are carried out via the use of a system comprising a liposomal complexed aminoglycoside composition, for example, a liposomal encapsulated amikacin composition (e.g., amikacin sulfate) and a nebulizer. In one embodiment, the liposomal aminoglycoside composition provided herein comprises about 60 mg/mL aminoglycoside, about 65 mg/mL aminoglycoside, about 70 mg/mL aminoglycoside, about 75 mg/mL aminoglycoside, about 80 mg/mL aminoglycoside, about 85 mg/mL aminoglycoside, or about 90 mg/mL aminoglycoside. In a further embodiment, the aminoglycoside is amikacin, for example, as amikacin sulfate.

In one embodiment of the NTM treatment methods described herein, the liposomal aminoglycoside composition is administered to a patient in need thereof once per day in a single dosing session. In a further embodiment, the composition is administered as an aerosol via a nebulizer. In another embodiment, the method comprises administering to a patient in need thereof one of the aminoglycoside compositions described herein every other day or every three days. In yet another embodiment, the method comprises administering to a patient in need thereof one of the aminoglycoside compositions described herein twice per day.

The methods provided herein, in one embodiment, comprise administering to a patient in need thereof one of the compositions described herein (e.g., via a nebulizer) for an administration period comprising at least one 1 month, 2 months, 3 months, 4 months, 5 months or 6 months. In one embodiment, an administration period is followed by a period where no composition is administered (referred to as "off period"), which is followed by another administration period. The off period, in one embodiment is about 1 month, about 2 months, about 3 months, about four months, about five months or about 6 months.

In one embodiment, the administration period is from about 15 days to about 400 days, e.g., from about 45 days to about 300 days, or from about 45 days to about 270 days, or from about 80 days to about 200 days. In one embodiment, the administration period comprises administration of the composition to a patient in need thereof in a once daily dosing session.

In another embodiment, the NTM treatment method described herein comprises administration of a liposomal complexed aminoglycoside composition to a patient in need thereof via a once daily dosing session for an administration period. In a further embodiment, the administration period is from about 15 to about 275 days, or from about 20 to about 235 days, or from about 28 days to about 150 days. For example, the methods provided herein comprise administering to a patient in need thereof an aminoglycoside composition once per day in a single dosing session for an administration period of from about 15 to about 300 days, or from about 15 to about 250 days, or from about 15 to about 200 days, or from about 15 to about 150 days, or from about 15 to about 125 days or from about 15 to about 100 days. In another embodiment, the administration period is from about 50 days to about 200 days. During the administration period, in one embodiment, the patient in need thereof is administered the aminoglycoside composition via nebulization, and about 500 mg to about 1000 mg aminoglycoside is administered daily in a single dosing session, for example, about 500 mg aminoglycoside to about 700 mg aminoglycoside (e.g., about 590 mg aminoglycoside).

In one embodiment, an administration period is followed by an off period from about 15 to about 200 days, for example, from about 15 days to about 150 days, or from about 15 days to about 75 days, from about 15 days to about 35 days, or from about 20 days to about 35 days, or from about 25 days to about 75 days, or from about 35 days to about 75 days or from about 45 days to about 75 days. In another embodiment, the off period is about 28 days or about 56 days. In other embodiments, the off period is about 50, 51, 52, 53, 54, 55, 56, 57, 58, 59 or 60 days, while in other embodiments, the off period is about 56 days.

In one embodiment, the patient in need thereof is administered the liposomal complexed aminoglycoside composition in a treatment cycle comprising an administration period and an off period. In a further embodiment, the treatment cycle is implemented at least once. In a further embodiment, the treatment cycle is repeated at least twice, for example, two, three, four, five, six, seven, eight, nine or ten times. In another embodiment, the treatment cycle is repeated at least three times, for example, at least three, at least four, at least five or at least six times.

Various treatment cycles for patients with NTM lung infections are provided in Table 3, below. However, in another embodiment, the method provided herein does not comprise an off period and instead includes only an administration period. In a further embodiment, one of the administration periods set forth in Table 3 is used in the method provided herein. In a further embodiment, the patient is administered the liposomal aminoglycoside composition once daily during the administration period in a single dosing session.

TABLE 3

Treatment cycles of the present invention

| Administration period | Off period | Treatment cycle(s) | Composition |
|---|---|---|---|
| 15 to 500 days | 15 to 75 days | At least once | Amikacin (500 mg-600 mg), DPPC, cholesterol, (lipid to aminoglycoside ratio by weight of 0.75:1 or less, e.g., 0.1:1.0 to about 1.25:1.0) |
| 15 to 450 days | 15 to 75 days | At least once | Amikacin (500 mg-600 mg), DPPC, cholesterol, (lipid to aminoglycoside ratio by weight of 0.75:1 or less, e.g., 0.1:1.0 to about 1.25:1.0) |
| 15 to 400 days | 15 to 75 days | At least once | Amikacin (500 mg-600 mg), DPPC, cholesterol, (lipid to aminoglycoside ratio by weight of 0.75:1 or less, e.g., 0.1:1.0 to about 1.25:1.0) |
| 15 to 350 days | 15 to 75 days | At least once | Amikacin (500 mg-600 mg), DPPC, cholesterol, (lipid to aminoglycoside ratio by weight of 0.75:1 or less, e.g., 0.1:1.0 to about 1.25:1.0) |
| 15 to 325 days | 15 to 75 days | At least once | Amikacin (500 mg-600 mg), DPPC, cholesterol, (lipid to aminoglycoside ratio by weight of 0.75:1 or less, e.g., 0.1:1.0 to about 1.25:1.0) |
| 15 to 300 days | 15 to 75 days | At least once | Amikacin (500 mg-600 mg), DPPC, cholesterol, (lipid to aminoglycoside ratio by weight of 0.75:1 or less, e.g., 0.1:1.0 to about 1.25:1.0) |
| 15 to 275 days | 15 to 75 days | At least once | Amikacin (500 mg-600 mg), DPPC, cholesterol, (lipid to aminoglycoside ratio by weight of 0.75:1 or less, e.g., 0.1:1.0 to about 1.25:1.0) |
| 15 to 255 days | 15 to 75 days | At least once | Amikacin (500 mg-600 mg), DPPC, cholesterol, (lipid to aminoglycoside ratio by weight of 0.75:1 or less, e.g., 0.1:1.0 to about 1.25:1.0) |
| 15 to 225 days | 15 to 75 days | At least once | Amikacin (500 mg-600 mg), DPPC, cholesterol, (lipid to aminoglycoside ratio by weight of 0.75:1 or less, e.g., 0.1:1.0 to about 1.25:1.0) |
| 15 to 200 days | 15 to 75 days | At least once | Amikacin (500 mg-600 mg), DPPC, cholesterol, (lipid to aminoglycoside ratio by weight of 0.75:1 or less, e.g., 0.1:1.0 to about 1.25:1.0) |
| 15 to 175 days | 15 to 75 days | At least once | Amikacin (500 mg-600 mg), DPPC, cholesterol, (lipid to aminoglycoside ratio by weight of 0.75:1 or less, e.g., 0.1:1.0 to about 1.25:1.0) |
| 15 to 150 days | 15 to 75 days | At least once | Amikacin (500 mg-600 mg), DPPC, cholesterol, (lipid to aminoglycoside ratio by weight of 0.75:1 or less, e.g., 0.1:1.0 to about 1.25:1.0) |
| 15 to 125 days | 15 to 75 days | At least once | Amikacin (500 mg-600 mg), DPPC, cholesterol, (lipid to aminoglycoside ratio by weight of 0.75:1 or less, e.g., 0.1:1.0 to about 1.25:1.0) |
| 15 to 100 days | 15 to 75 days | At least once | Amikacin (about 590 mg), DPPC, cholesterol, (L:D by weight of about 0.7:1) |
| 15 to 75 days | 15 to 75 days | At least once | Amikacin (about 590 mg), DPPC, cholesterol, (L:D by weight of about 0.7:1) |
| 15 to 50 days | 15 to 75 days | At least once | Amikacin (about 590 mg), DPPC, cholesterol, (L:D by weight of about 0.7:1) |
| 20 to 100 days | 15 to 75 days | At least once | Amikacin (about 590 mg), DPPC, cholesterol, (L:D by weight of about 0.7:1) |

In one embodiment, the system provided herein comprises an about 8 mL liposomal amikacin composition and a nebulizer. In one embodiment, the density of the liposomal amikacin composition is about 1.05 gram/mL; and in one embodiment, approximately 8.4 grams of the liposomal amikacin composition per dose is present in the composition of the invention. In a further embodiment, the entire volume of the composition is administered to a subject in need thereof.

In one embodiment, the pharmaceutical composition provided herein comprises at least one aminoglycoside, at least one phospholipid and a sterol. In a further embodiment, the pharmaceutical composition comprises an aminoglycoside, DPPC and cholesterol. In one embodiment, the pharmaceutical composition is the composition provided in Table 4, below.

TABLE 4

Pharmaceutical Compositions

| Component | Concentration |
|---|---|
| Composition A (pH 6.0-7.0) | |
| Aminoglycoside | 60-80 mg/mL |
| Phospholipid | 30-40 mg/mL |
| Sterol | 10-20 mg/mL |
| Salt | 0.5%-5.0% |
| Composition B (pH 6.0-7.0) | |
| Amikacin Sulfate | 60-80 mg/mL |
| DPPC | 30-40 mg/mL |
| Cholesterol | 10-20 mg/mL |
| NaCl | 0.5%-5.0% |
| Composition C (pH 6.0-7.0) | |
| Amikacin Sulfate | 70-80 mg/mL |
| DPPC | 35-40 mg/mL |
| Cholesterol | 15-20 mg/mL |
| NaCl | 0.5%-5.0% |
| Composition D (pH ~6.5) | |
| Aminoglycoside | ~70 mg/mL |
| Phospholipid | ~32-35 mg/mL |
| Sterol | ~16-17 mg/mL |
| Salt | ~1.5% |
| Composition E (pH ~6.5) | |
| Amikacin Sulfate | ~70 mg/mL |
| DPPC | ~32-35 mg/mL |
| Cholesterol | ~16-17 mg/mL |
| NaCl | ~1.5% |
| Composition F (pH ~6.5) | |
| Amikacin Sulfate | ~70 mg/mL |
| DPPC | ~30-35 mg/mL |
| Cholesterol | ~15-17 mg/mL |
| NaCl | ~1.5% |

It should be noted that increasing aminoglycoside concentration alone may not result in a reduced dosing time. For example, in one embodiment, the lipid to drug ratio is fixed, and as amikacin concentration is increased (and therefore lipid concentration is increased, since the ratio of the two is fixed, for example at ~0.7:1 by weight), the viscosity of the solution also increases, which slows nebulization time.

As provided throughout, the methods described herein comprise administering to a patient in need of treatment of an NTM lung infection, an effective amount of a liposomal aminoglycoside composition via inhalation. In one embodiment, inhalation delivery is conducted via a nebulizer. The nebulizer provides an aerosol mist of the composition for delivery to the lungs of the patient.

In one embodiment, the system provided herein comprises a nebulizer selected from an electronic mesh nebulizer, pneumonic (jet) nebulizer, ultrasonic nebulizer, breath-enhanced nebulizer and breath-actuated nebulizer. In one embodiment, the nebulizer is portable.

In one embodiment, the method for treating an NTM infection is carried out via administration of a liposomal complexed aminoglycoside composition to a patient in need thereof via a nebulizer in once daily dosing sessions. In a further embodiment, the aminoglycoside is amikacin, e.g., amikacin sulfate. In a further embodiment, the lipid component of the liposomes comprises DPPC and cholesterol. In even a further embodiment, the nebulizer is one of the nebulizers described in U.S. Patent Application Publication No. 2013/0330400, incorporated by reference herein in its entirety for all purposes.

The principle of operation of a pneumonic nebulizer is generally known to those of ordinary skill in the art and is described, e.g., in Respiratory Care, Vol. 45, No. 6, pp. 609-622 (2000). Briefly, a pressurized gas supply is used as the driving force for liquid atomization in a pneumatic nebulizer. Compressed gas is delivered, which causes a region of negative pressure. The solution to be aerosolized is then delivered into the gas stream and is sheared into a liquid film. This film is unstable and breaks into droplets because of surface tension forces. Smaller particles, i.e., particles with the MMAD and FPF properties described above, can then be formed by placing a baffle in the aerosol stream. In one pneumonic nebulizer embodiment, gas and solution is mixed prior to leaving the exit port (nozzle) and interacting with the baffle. In another embodiment, mixing does not take place until the liquid and gas leave the exit port (nozzle). In one embodiment, the gas is air, $O_2$ and/or $CO_2$.

In one embodiment, droplet size and output rate can be tailored in a pneumonic nebulizer. However, consideration should be paid to the composition being nebulized, and whether the properties of the composition (e.g., % associated aminoglycoside) are altered due to the modification of the nebulizer. For example, in one embodiment, the gas velocity and/or pharmaceutical composition velocity is modified to achieve the output rate and droplet sizes of the present invention. Additionally or alternatively, the flow rate of the gas and/or solution can be tailored to achieve the droplet size and output rate of the invention. For example, an increase in gas velocity, in one embodiment, decreased droplet size. In one embodiment, the ratio of pharmaceutical composition flow to gas flow is tailored to achieve the droplet size and output rate of the invention. In one embodiment, an increase in the ratio of liquid to gas flow increases particle size.

In one embodiment, a pneumonic nebulizer output rate is increased by increasing the fill volume in the liquid reservoir. Without wishing to be bound by theory, the increase in output rate may be due to a reduction of dead volume in the nebulizer. Nebulization time, in one embodiment, is reduced by increasing the flow to power the nebulizer. See, e.g., Clay et al. (1983). Lancet 2, pp. 592-594 and Hess et al. (1996). Chest 110, pp. 498-505.

In one embodiment, a reservoir bag is used to capture aerosol during the nebulization process, and the aerosol is subsequently provided to the subject via inhalation. In another embodiment, the nebulizer provided herein includes a valved open-vent design. In this embodiment, when the patient inhales through the nebulizer, nebulizer output is increased. During the expiratory phase, a one-way valve diverts patient flow away from the nebulizer chamber.

In one embodiment, the nebulizer provided herein is a continuous nebulizer. In other words, refilling the nebulizer with the pharmaceutical composition while administering a dose is not needed. Rather, the nebulizer has at least an 8 mL capacity or at least a 10 mL capacity.

In one embodiment, the nebulizer provided herein does not use an air compressor and therefore does not generate an air flow. In one embodiment, aerosol is produced by the aerosol head which enters the mixing chamber of the device. When the patient inhales, air enters the mixing chamber via one-way inhalation valves in the back of the mixing chamber and carries the aerosol through the mouthpiece to the patient. On exhalation, the patient's breath flows through the one-way exhalation valve on the mouthpiece of the device. In one embodiment, the nebulizer continues to generate aerosol into the mixing chamber which is then drawn in by the subject on the next breath—and this cycle continues until the nebulizer medication reservoir is empty.

In one embodiment, the nebulization time of an effective amount of an aminoglycoside composition provided herein is less than 20 minutes, less than 18 minutes, less than 16 minutes or less than 15 minutes. In one embodiment, the nebulization time of an effective amount of an aminoglycoside composition provided herein is less than 15 minutes or less than 13 minutes. In one embodiment, the nebulization time of an effective amount of an aminoglycoside composition provided herein is about 13 minutes.

In one embodiment, the composition described herein is administered once daily to a patient in need thereof.

In another embodiment, a patient is treated for an NTM lung infection with one of the methods and/or compositions provided herein. In a further embodiment, the composition comprises a liposomal amikacin composition. In even a further embodiment, the composition comprises from about 500 mg to about 600 mg amikacin, DPPC and cholesterol, and the lipid to aminoglycoside weight ratio of the composition is 0.75:1.0 or less, e.g., about 0.7:1.0 or about 0.5:1.0 to about 0.8:1.0.

In one embodiment, the patient subjected to one of the treatment methods provided herein is a patient that was previously non-responsive to a different NTM treatment. In a further embodiment, the composition administered to the patient in need of treatment is one of the compositions set forth in Table 4, above.

In one embodiment, prior to nebulization of the aminoglycoside composition, about 70% to about 100% of the aminoglycoside present in the composition is liposomal complexed. In a further embodiment, the aminoglycoside is an aminoglycoside. In even a further embodiment, the aminoglycoside is amikacin. In another embodiment, prior to nebulization, about 80% to about 99%, or about 85% to about 99%, or about 90% to about 99% or about 95% to about 99% or about 96% to about 99% of the aminoglycoside present in the composition is liposomal complexed. In a further embodiment, the aminoglycoside is amikacin or tobramycin. In even a further embodiment, the aminoglycoside is amikacin. In another embodiment, prior to nebulization, about 98% of the aminoglycoside present in the composition is liposomal complexed. In a further embodiment, the aminoglycoside is amikacin or tobramycin. In even a further embodiment, the aminoglycoside is amikacin (e.g., as amikacin sulfate).

In one embodiment, upon nebulization, about 20% to about 50% of the liposomal complexed aminoglycoside agent is released, due to shear stress on the liposomes. In a further embodiment, the aminoglycoside agent is an amikacin. In another embodiment, upon nebulization, about 25% to about 45%, or about 30% to about 40% of the liposomal complexed aminoglycoside agent is released from the liposomal complex, due to shear stress on the liposomes. In a further embodiment, the aminoglycoside agent is amikacin. In even a further embodiment, the amikacin is amikacin sulfate.

Upon nebulization of the composition described herein, i.e., for administration to a patient in need of treatment of an NTM infection, an aerosolized composition is formed, and in one embodiment, the mass median aerodynamic diameter (MMAD) of the aerosolized composition is about 1.0 μm to about 4.2 μm as measured by the Anderson Cascade Impactor (ACI). In one embodiment, the MMAD of the aerosolized composition is about 3.2 μm to about 4.2 μm as measured by the ACI. In one embodiment, the MMAD of the aerosolized composition is about 1.0 μm to about 4.9 μm as measured by the Next Generation Impactor (NGI). In a further embodiment, the MMAD of the aerosolized composition is about 4.4 μm to about 4.9 μm as measured by the NGI.

The fine particle fraction (FPF) of the aerosolized composition, in one embodiment, is greater than or equal to about 64%, as measured by the Anderson Cascade Impactor (ACI), or greater than or equal to about 51%, as measured by the Next Generation Impactor (NGI). In one embodiment, embodiment, the FPF of the aerosolized composition is greater than or equal to about 70%, as measured by the ACI, greater than or equal to about 51%, as measured by the NGI, or greater than or equal to about 60%, as measured by the NGI.

Upon nebulization, the liposomes in the pharmaceutical composition leak drug. In one embodiment, the amount of liposomal complexed aminoglycoside post-nebulization is about 45% to about 85%, or about 50% to about 80% or about 51% to about 77%. These percentages are also referred to herein as "percent associated aminoglycoside post-nebulization." As provided herein, in one embodiment, the liposomes comprise an aminoglycoside, e.g., amikacin. In one embodiment, the percent associated aminoglycoside post-nebulization is from about 60% to about 70%. In a further embodiment, the aminoglycoside is amikacin. In another embodiment, the percent associated aminoglycoside post-nebulization is about 67%, or about 65% to about 70%. In a further embodiment, the aminoglycoside is amikacin. In even a further embodiment, the amikacin is amikacin sulfate.

In one embodiment, the percent associated aminoglycoside post-nebulization is measured by reclaiming the aerosol from the air by condensation in a cold-trap, and the liquid is subsequently assayed for free and encapsulated aminoglycoside (associated aminoglycoside).

In another embodiment, the methods provided herein are implemented for the treatment or prophylaxis of one or more NTM pulmonary infections in a cystic fibrosis patient. In a further embodiment, the composition administered to the patient in need of treatment is one of the compositions set forth in Table 4, above.

In one embodiment, the patient in need of treatment of the NTM pulmonary infection is a bronchiectasis patient. In one embodiment, the bronchiectasis is non-Cystic Fibrosis (CF) bronchiectasis. In another embodiment, the bronchiectasis is associated with CF in a patient in need of treatment.

In another embodiment, the patient in need of treatment of the NTM pulmonary infection is a COPD patient. In yet another embodiment, the patient in need of treatment of the NTM pulmonary infection is an asthma patient. In a further embodiment, the composition administered to the patient in need of treatment is one of the compositions set forth in Table 4, above.

In one embodiment, a patient in need of treatment with one of the methods described herein is a Cystic Fibrosis patient, a bronchiectasis patient, a ciliary dyskinesia patient, a chronic smoker, a chronic obstructive pulmonary disorder (COPD) patient, or a patient who has been previously non-responsive to treatment. In another embodiment, a cystic fibrosis patient is treated for an NTM pulmonary infection with one of the methods provided herein. In yet another embodiment, the patient is a bronchiectasis patient, a COPD patient or an asthma patient. The pulmonary NTM infection, in one embodiment, is MAC, *M. kansasii, M. abscessus*, or *M. fortuitum*. In a further embodiment, the pulmonary NTM infection is a MAC infection.

A patient subjected to the methods described herein, in one embodiment, has a comorbid condition. For example, in one embodiment, the patient in need of treatment with one of the methods described herein has diabetes, mitral valve disorder (e.g., mitral valve prolapse), acute bronchitis, pulmonary hypertension, pneumonia, asthma, trachea cancer, bronchus cancer, lung cancer, cystic fibrosis, pulmonary fibrosis, a larynx anomaly, a trachea anomaly, a bronchus anomaly, aspergillosis, HIV or bronchiectasis, in addition to the pulmonary NTM infection.

In one embodiment, a patient subjected to one of the NTM methods described herein exhibits an NTM culture conversion to negative during the administration period of the liposomal aminoglycoside composition, or after the administration period has concluded. The time to conversion, in one embodiment, is about 10 days, or about 20 days or about 30 days or about 40 days, or about 50 days, or about 60 days, or about 70 days, or about 80 days, or about 90 days, or about 100 days or about 110 days. In another embodiment, the time to conversion is from about 20 days to about 200 days, from about 20 days to about 190 days, from about 20 days to about 180 days, from about 20 days to about 160 days, from about 20 days to about 150 days, from about 20 days to about 140 days, from about 20 days to about 130 days, from about 20 days to about 120 days, from about 20 days to about 110 days, from about 30 days to about 110 days, or from about 30 days to about 100 days.

In some embodiments, the patient experiences an improvement in lung function for at least 15 days after the administration period ends, as compared to the $FEV_1$ of the patient prior to treatment. For example, the patient may experience an increase in $FEV_1$, an increase in blood oxygen saturation, or both. In some embodiments, the patient has an $FEV_1$ (after the administration period or treatment cycle) that is increased by at least 5% over the $FEV_1$ prior to the administration period. In other embodiments, $FEV_1$ is increased by 5 to 50% over the $FEV_1$ prior to the administration period. In other embodiments, $FEV_1$ is increased by 25 to 500 mL over $FEV_1$ prior to the administration period. In some embodiments, blood oxygen saturation is increased by at least 1% over oxygen saturation prior to the administration period.

In one embodiment, the 6-minute walk test (6MWT) is used to assess the effectiveness of the treatment methods provided herein. The 6MWT is used for the objective evaluation of functional exercise capacity and is a practical, simple test that measures the distance that a patient can walk in a period of 6 minutes (see American Thoracic Society. (2002). *Am J Respir Crit Care Med.* 166, pp. 111-117, incorporated by reference herein in its entirety for all purposes).

In one embodiment, a patient subjected to one of the NTM methods described herein exhibits an increased number of meters walked in the 6MWT, as compared to prior to undergoing the treatment method. The increased number of meters walked in the 6MWT, in one embodiment, is about 5 meters, about 10 meters, about 15 meters, about 20 meters, about 25 meters, about 30 meters, about 35 meters, about 40 meters, about 45 meters, or about 50 meters. In another embodiment, the increased number of meters walked in the 6MWT is at least about 5 meters, at least about 10 meters, at least about 15 meters, at least about 20 meters, at least about 25 meters, at least about 30 meters, at least about 35 meters, at least about 40 meters, at least about 45 meters, or at least about 50 meters. In yet another embodiment, the increased number of meters walked in the 6MWT is from about 5 meters to about 50 meters, or from about 5 meters to about 40 meters, or from about 5 meters to about 30 meters or from about 5 meters to about 25 meters.

In another embodiment, a patient subjected to one of the NTM methods described herein exhibits a greater number of meters walked in the 6MWT, as compared to a patient undergoing a non-liposomal aminoglycoside treatment. The greater number of meters walked in the 6MWT, as compared to a patient undergoing a non-liposomal aminoglycoside treatment, in one embodiment, is about 5 meters, about 10 meters, about 15 meters, about 20 meters, about 25 meters, about 30 meters, about 35 meters, about 40 meters, about 45 meters, about 50 meters, about 60 meters, about 70 meters or about 80 meters. In another embodiment, the greater number of meters walked in the 6MWT is at least about 5 meters, at least about 10 meters, at least about 15 meters, at least about 20 meters, at least about 25 meters, at least about 30 meters, at least about 35 meters, at least about 40 meters, at least about 45 meters, or at least about 50 meters. In yet another embodiment, the greater number of meters walked in the 6MWT is from about 5 meters to about 80 meters, or from about 5 meters to about 70 meters, or from about 5 meters to about 60 meters or from about 5 meters to about 50 meters.

In one embodiment, the liposomal aminoglycoside composition provided herein is administered to a patient in need of treatment of an NTM lung disease with an additional therapy.

In one embodiment, the liposomal aminoglycoside composition provided herein is administered to a patient in need of treatment of an NTM lung disease with one or more additional therapeutic agents. The one or more additional therapeutics agents in one embodiment, is administered orally. In another embodiment, the one or more additional therapeutics agents in one embodiment, is administered intravenously. In yet another embodiment, the one or more additional therapeutics agents in one embodiment, is administered via inhalation.

The one or more additional therapeutic agents in one embodiment, is a macrolide antibiotic. In a further embodiment, the macrolide antibiotic is azithromycin, clarithromycin, erythromycin, carbomycin A, josamycin, kitamycin, midecamycin, oleandomycin, solithromycin, spiramycin, troleandomycin, tylosin, roxithromycin, or a combination thereof. In a further embodiment, the macrolide antibiotic is administered orally.

In one embodiment, the one or more additional therapeutic agents is the macrolide antibiotic azithromycin, clarithromycin, erythromycin, or a combination thereof. In a further embodiment, the macrolide antibiotic is administered orally.

In another embodiment, the liposomal aminoglycoside composition provided herein is administered to a patient in need of treatment of an NTM lung disease with one or more additional therapeutic agents, and the one or more additional therapeutic agents is a rifamycin compound. In a further embodiment, the rifamycin is rifampin. In another embodiment, the rifamycin is rifabutin, rifapentine, rifaximin, or a combination thereof.

In yet embodiment, the one or more additional therapeutic agents is a quinolone. In a further embodiment, the quinolone is a fluoroquinolone. In another embodiment, the quinolone is ciprofloxacin, levofloxacin, gatifloxacin, enoxacin, levofloxacin, ofloxacin, moxifloxacin, trovafloxacin, or a combination thereof.

In one embodiment, a second therapeutic agent is administered to the patient in need of NTM treatment, and the second therapeutic agent is a second aminoglycoside. In a further embodiment, the second aminoglycoside is amikacin, apramycin, arbekacin, astromicin, bekanamycin, boholmycin, brulamycin, capreomycin, dibekacin, dactimicin, etimicin, framycetin, gentamicin, H107, hygromycin, hygromycin B, inosamycin, K-4619, isepamicin, KA-5685, kanamycin, neomycin, netilmicin, paromomycin, plazomicin, ribostamycin, sisomicin, rhodestreptomycin, sorbistin, spectinomycin, sporaricin, streptomycin, tobramycin, verdamicin, vertilmicin, a pharmaceutically acceptable salt thereof, or a combination thereof. In a further embodiment, the second aminoglycoside is administered intravenously or via inhalation. In one embodiment the second aminoglycoside is streptomycin.

In another embodiment, the liposomal aminoglycoside composition provided herein is administered to a patient in need of treatment of an NTM lung disease with one or more additional therapeutic agents, and the one or more additional therapeutic agents is ethambutol, isoniazid, cefoxitin or imipenem.

EXAMPLES

The present invention is further illustrated by reference to the following Examples. However, it should be noted that these Examples, like the embodiments described above, are illustrative and are not to be construed as restricting the scope of the invention in any way.

Example 1: Randomized-Double Blind Study of Liposomal Amikacin for Inhalation (LAI) in Patients with Non-Tuberculous *Mycobacterium* (NTM) Lung Disease (LD)

Figure 2:
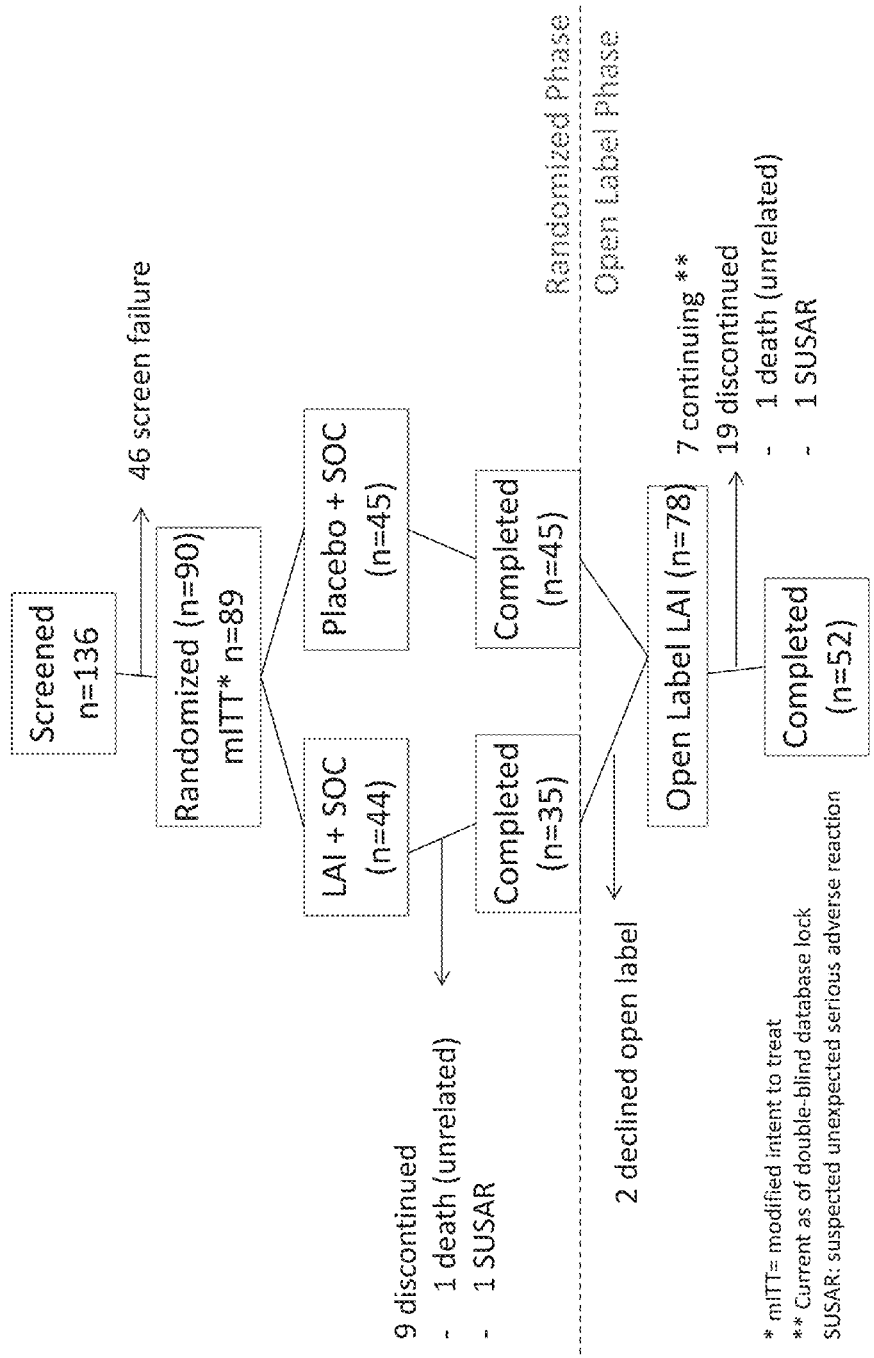
FIG. 2 shows the patient distribution for the randomized, double-blind, placebo controlled study of liposomal complexed amikacin in patients with recalcitrant nontuberculous mycobacterial lung infection, described in Example 1.

The increasing prevalence of NTM-LD is a public health concern and its management, particularly in cystic fibrosis patients, is complicated by prolonged use of multidrug regimens, drug toxicity, and poor response rates. LAI (also referred to herein as "Arikayce™" or "ARIKAYCE™") is a sustained-release lipid composition of amikacin in development for treatment of patients with recalcitrant NTM lung disease. This study evaluated the efficacy, safety, and tolerability of LAI in these patients in a randomized, double-blind (DB) study, conducted at 19 centers in North America. FIG. 1 is a flow chart showing the study design and FIG. 2 shows the patient distribution for the study.

The LAI composition had the following components:

| LAI composition | |
|---|---|
| Amikacin Sulfate | ~70 mg/mL |
| DPPC | ~30-35 mg/mL |
| Cholesterol | ~15-17 mg/mL |
| NaCl | ~1.5% |

Figure 3:
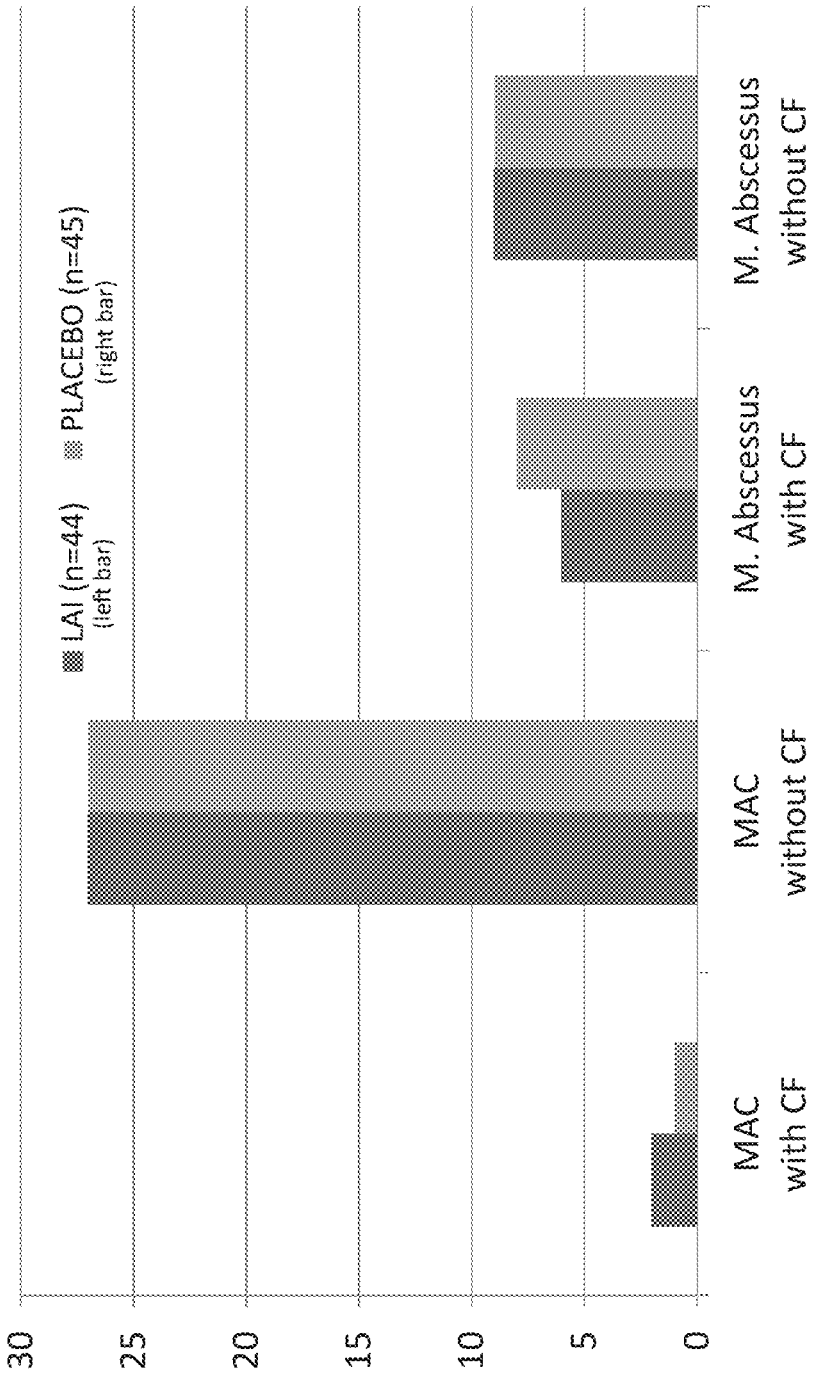
FIG. 3 shows the number of patients in each NTM treatment group.

Eligible NTM patients on a stable drug regimen were stratified based on presence or absence of cystic fibrosis (CF), and *Mycobacterium avium* complex (MAC) versus *Mycobacterium abscessus* (*M. abscessus*) lung disease, and randomized 1:1 to receive either once daily 590 mg LAI or placebo via eFlow® nebulizer system (PARI Pharma GmbH) for 84 days added to their ongoing stable drug regimen. FIG. 3 shows the number of patients in each group (randomized per strata). Patients were eligible for enrollment if they had pulmonary NTM infection refractory to American Thoracic Society/Infectious Disease Society of America (ATS/IDSA) guideline-based therapy for 6 months prior to screening.

After completing the double blind (DB) phase, patients who consented to the open-label (OL) phase received LAI 590 mg once daily, for 84 more days (FIGS. 1 and 2).

Of 136 screened patients, 90 were randomized (19% CF; 81% non-CF; 64% with MAC and 36% with *M. abscessus*). 54% of patients were >60 years of age; 31% were >40-60 years, and 14% were 18-40 years. The baseline mean age was 58.5 years (standard deviation, 15.83 years).

The study is complete, with 80 and 59 patients having completed the DB and OL phases, respectively. Demographics and baseline characteristics of the mITT population are provided below in Table 5.

TABLE 5

Demographics and Baseline Characteristics of mITT Population

| | LAI (n = 44) | Placebo (n = 45) | Overall (n = 89) |
|---|---|---|---|
| Gender, n (%) | | | |
| Male | 6 (13.6) | 5 (11.1) | 11 (12.4) |
| Female | 38 (86.4) | 40 (88.9) | 78 (87.6) |
| Race/Ethnicity, n (%) | | | |
| Caucasian (not of Hispanic Origin) | 42 (95.5) | 40 (88.9) | 82 (92.1) |
| Hispanic | 0 | 2 (4.4) | 2 (2.2) |
| African | 0 | 1 (2.2) | 1 (1.1) |
| Asian | 2 (4.5) | 2 (4.4) | 4 (4.5) |
| Other | 0 | 0 | 0 |
| Baseline Age, years | | | |
| n | 44 | 45 | 89 |
| Mean (SD) | 58.0 (16.61) | 59.1 (15.20) | 58.5 (15.83) |
| Median | 61.5 | 63.0 | 63.0 |
| Min, Max | 18, 85 | 19, 80 | 18, 85 |
| Baseline $FEV_1$ Percent Predicted | | | |
| n | 44 | 45 | 89 |
| Mean (SD) | 65.56 (21.339) | 62.56 (17.168) | 63.06 (19.239) |
| Median | 61.25 | 61.00 | 61.00 |
| Min, Max | 30.2, 114.9 | 34.4, 101.6 | 30.2, 114.9 |

The sample population enrolled in the mITT study exhibited the following: (1) comorbid lung disease, with 17 of the patients having cystic fibrosis; (2) a mean age of 59 years, including the younger cystic fibrosis patients; (3) lung abnormalities including 68 patients with cavitary lesions, and 21 patients with nodular disease which further includes minimal cavitary disease; (4) a mean body mass index (BMI) of 21.98, whereas comparable CDC data collected from between 2007 and 2010 reveals U.S average BMI of adult males to be 28.6 and adult females to be 28.7; and (5) an average baseline of ~441 m for all patients, with both arms having approximately the same mean baseline six-minute walk distance.

Sputum for semi-quantitative mycobacterial culture, smear status, signs/symptoms, pulmonary exacerbation occurrence, antimycobacterial drug rescue, six-minute walk distance (6MWD), computed tomography of the chest, spirometry, clinical/laboratory safety parameters, and quality of life measures were evaluated every 28 days. The primary endpoint was change from baseline on the semi-quantitative scale for mycobacterial culture; a secondary endpoint was the proportion of patients with NTM culture conversion to negative for LAI vs placebo at Day 84. All patients had a safety follow-up visit 28 days after the last dose of study drug, up to Day 196 for those in the OL phase.

Figure 4:
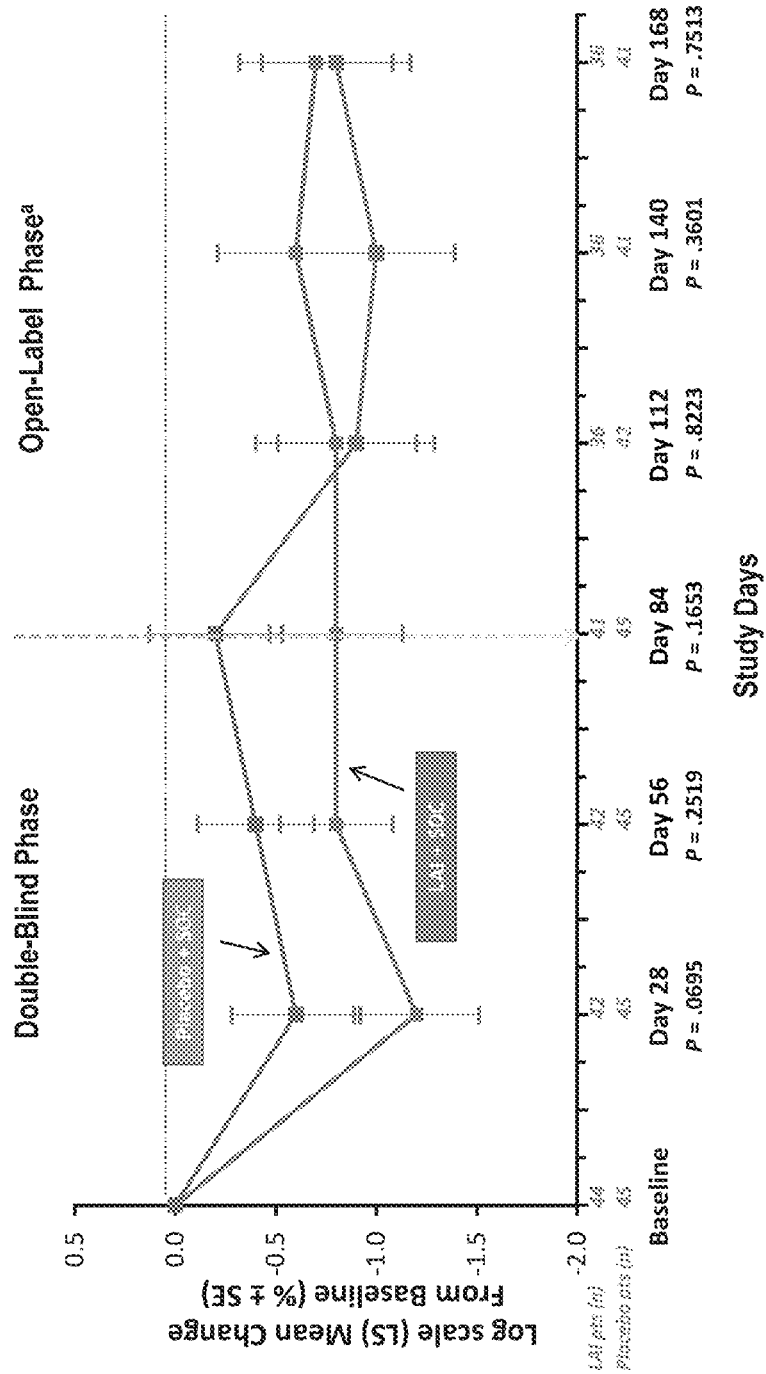
FIG. 4 shows the log scale (LS) mean change from baseline on the full semi quantitative scale for mycobacterial culture for the modified intent to treat patient (mITT) population as a function of study day for both the double-blind phase and the open-label phase of the study set forth in Example 1.

FIG. 4 is a graph showing the mean change from baseline on the full semi quantitative scale for mycobacterial culture (mITT population) as a function of study day in both the double-blind phase and the open-label phase of the study. As shown in the figure, patients treated with LAI showed at least a one-step reduction in the treatment arm versus the placebo arm in the double-blind phase.

The proportion of patients with negative sputum cultures for NTM in each subgroup by treatment arm at Day 84 and Day 168 (mITT population) are summarized in Tables 6-8. At Day 84, statistically significant between-group differences in patients achieving negative sputum cultures for NTM, in favor of LAI vs. placebo, were seen in patients with non-CF infection (P=0.01), MAC infection (P=0.017), females (P=0.004), Caucasians (P=0.031), and patients aged <63 years (P=0.041) (Table 6).

At Day 168, statistically significantly more patients with MAC infection in the prior LAI arm vs. prior placebo arm had negative sputum cultures for NTM (P=0.026) (Table 6). In subgroup analyses (Table 7 and Table 8) of patients with NTM lung infection refractory to guideline-based therapy, LAI appeared superior to placebo with regard to negative sputum cultures for NTM in patients with non-CF underlying lung disease and MAC infection. The subgroup of patients with non-CF MAC infection demonstrated a positive efficacy result within the timeframe of the study (i.e., 12-week double-blind phase and 12-week open-label phase)

Time to culture conversion showed statistically significantly greater proportion of patients in the LAI arm becoming culture negative at all visits in the double blind phase (Days 28, 56, and 84) (FIG. 5 top). Specifically, LAI achieved statistical significance in achieving a negative culture at Day 84, with 11 of 44 patients on LAI versus 3 of 45 patients on placebo (P=0.01) (FIG. 5 top). Compared with placebo, LAI demonstrated statistical significance with regard to the proportion of patients with MAC infections who achieved culture negativity at Day 56 (LAI, 10/29 patients vs. placebo, 2/28 patients; P=0.0144) and at Day 84 (LAI, 10/29 patients vs. placebo, 3/28 patients; P=0.0273) (FIG. 5 bottom).

In patients refractory to NTM-regimens for at least 6 months, LAI, an inhaled amikacin composition, lead to significantly greater culture conversion compared to placebo within 84 days. Patients with at least one NTM culture negative result are provided in FIG. 6.

TABLE 6

Proportion of Patients with negative sputum cultures for NTM in each subgroup by treatment arm at days 84 and 168 (mITT population)[a]

| Subgroups, n/n (%) | Day 84 (double-blind phase) | | | Day 168 (open-label phase) | | |
| --- | --- | --- | --- | --- | --- | --- |
| | LAI (n = 44) | Placebo (n = 45) | P value[b] | Prior LAI[c] (n = 35) | Prior placebo[c] (n = 43) | P value[b] |
| Infection type | | | | | | |
| MAC | 10/27 (37.0) | 3/28 (10.7) | .017 | 12/24 (50.0) | 6/27 (22.2) | .026 |
| MAB | 1/14 (7.1) | 0/17 | .317 | 1/11 (9.1) | 2/14 (14.3) | .691 |
| CF | 0/7 | 0/9 | NA | 1/6 (16.7) | 0/7 | .221 |
| Non-CF | 11/34 (32.4) | 3/36 (8.3) | .01 | 12/29 (41.4) | 8/34 (23.5) | .122 |
| Gender | | | | | | |
| Female | 11/36 (30.60) | 2/40 (5.0) | .004 | 12/31 (38.7) | 8/36 (22.2) | .137 |
| Male | 0/5 | 1/5 (20.0) | .414 | 1/4 (25.0) | 0/5 | .480 |
| Ethnicity | | | | | | |
| Caucasian | 10/39 (25.6) | 3/40 (7.5) | .031 | 13/33 (39.4) | 8/37 (21.6) | .107 |
| Non-Caucasian | 1/2 (50.0) | 0/5 | NA | 0/2 | 0/4 | N/A |
| Age | | | | | | |
| <63 years | 7/21 (33.3) | 2/22 (9.1) | .041 | 7/19 (36.8) | 3/20 (15.0) | .098 |
| >63 years | 4/20 (20.0) | 1/23 (4.3) | .108 | 6/16 (37.5) | 5/21 (23.8) | .367 |

CF, cystic fibrosis; LAI, liposomal amikacin for inhalation; MAB, *Mycobacterium avium* complex; mITT, modified intent-to-treat; NTM, nontuberculous mycobacteria; NA, not available.
[a]Missing values are excluded under the assumption of missing at random, for which missing baseline or post-baseline values are excluded but all non-missing data are included (ie, exclusion is not at subject-level but, rather, at time point-level).
[b]For pairwise comparisons of the LAI arm with the placebo arm, a stratified Cochran-Mantel-Haenszel test of treatment arm adjusting for the randomization strata was used.
[c]All patients received LAI in the open-label phase.

TABLE 7

Subgroup analysis of patients with MAC infection who achieved negative sputum cultures for NTM by treatment arm at days 84 and 168 168 (mITT population)[a]

| | Day 84 (double-blind phase) | | | Day 168 (open-label phase) | | |
|---|---|---|---|---|---|---|
| Subgroups, n/n (%) | LAI (n = 29) | Placebo (n = 28) | P value[b] | Prior LAI[c] (n = 24) | Prior placebo[c] (n = 28) | P value[b] |
| Infection type | | | | | | |
| CF | 0/2 | 0/1 | NA | 0/2 | 0/1 | N/A |
| Non-CF | 10/25 (40.0) | 3/27 (11.1) | .025 | 12/22 (54.6) | 6/26 (23.1) | .037 |
| Cavitary disease | 5/17 (29.4) | 2/20 (10.0) | .212 | 5/14 (35.7) | 2/19 (10.5) | .106 |
| Non-cavitary disease | 5/10 (50.0) | 1/8 (12.5) | .152 | 7/10 (70.0) | 4.8 (50.0) | .631 |
| Gender | | | | | | |
| Female | 10/25 (40.0) | 2/25 (8.0) | .018 | 12/22 (54.6) | 6/24 (25.0) | .069 |
| Male | 0/2 | 1/3 (33.3) | 1.000 | 0/2 | 0/3 | N/A |
| Ethnicity | | | | | | |
| Caucasian | 10/27 (37.0) | 3/25 (12.0) | .055 | 12/24 (50.0) | 6/24 (25.0) | .135 |
| Non-Caucasian | 0/0 | 0/3 | NA | 0/0 | 0/3 | NA |
| Age | | | | | | |
| <63 years | 6/13 (46.2) | 2/11 (18.2) | .211 | 6/13 (46.2) | 2/11 (18.2) | .211 |
| >63 years | 4/14 (28.6) | 1/17 (5.9) | .148 | 6/11 (54.6) | 4/16 (25.0) | .224 |

CF, cystic fibrosis; LAI, liposomal amikacin for inhalation; MAC, *Mycobacterium avium* complex; mITT, modified intent-to-treat; NA, not available.
[a]Missing values are excluded under the assumption of missing at random, for which missing baseline or post-baseline values are excluded but all non-missing data are included (ie, exclusion is not at subject-level but, rather, at time point-level).
[b]Pairwise comparisons of the LAI arm with the placebo arm were based on Fisher's Exact Test.
[c]All patients received LAI in the open-label phase.

TABLE 8

Subgroup analysis of patients with *M. abscessus* (MAB) infection who achieved negative sputum cultures for NTM by treatment arm at days 84 and 168 168 (mITT population)[a]

| | Day 84 (double-blind phase) | | | Day 168 (open-label phase) | | |
|---|---|---|---|---|---|---|
| Subgroups, n/n (%) | LAI (n = 15) | Placebo (n = 17) | P value[b] | Prior LAI[c] (n = 11) | Prior placebo[c] (n = 15) | P value[b] |
| Infection type | | | | | | |
| CF | 0/5 | 0/8 | NA | 1/4 (25.0) | 0/6 | 400 |
| Non-CF | 1/9 (11.1) | 0/9 | 1.000 | 0/7 | 2/8 (25.0) | .467 |
| Cavitary disease | 1/13 (7.7) | 0/15 | .464 | 1/10 (10.0) | 2/12 (16.7) | 1.000 |
| Non-cavitary disease | 0/1 | 0/2 | NA | 0/1 | 0/2 | N/A |
| Gender | | | | | | |
| Female | 1/11 (9.1) | 0/15 | .423 | 0/9 | 212 (16.7) | .486 |
| Male | 0/3 | 0/2 | NA | 1/2 (50.0) | 0/2 | 1.000 |
| Ethnicity | | | | | | |
| Caucasian | 0/12 | 0/15 | NA | 1/9 (11.1) | 2/13 (15.4) | 1.000 |
| Non-Caucasian | 1/2 (50.0) | 0/2 | 1.000 | 0/2 | 0/1 | NA |
| Age | | | | | | |
| <63 years | 1/8 (12.5) | 0/11 | .421 | 1/6 (16.7) | 1/9 (11.1) | 1.000 |
| >63 years | 0.6 | 0/6 | NA | 0/5 | 1/5 (20.0) | 1.000 |

CF, cystic fibrosis; LAI, liposomal amikacin for inhalation; MAB, *Mycobacterium abscessus*; MiTT, modified intent-to-treat; NA, not available.
[a]Missing values are excluded under the assumption of missing at random, for which missing baseline or post-baseline values are excluded but all non-missing data are included (ie, exclusion is not at subject-level but, rather, at time point-level).
[b]Pairwise comparisons of the LAI arm with the placebo arm were based on Fisher's Exact Test.
[c]All patients received LAI in the open-label phase.

Figure 7:
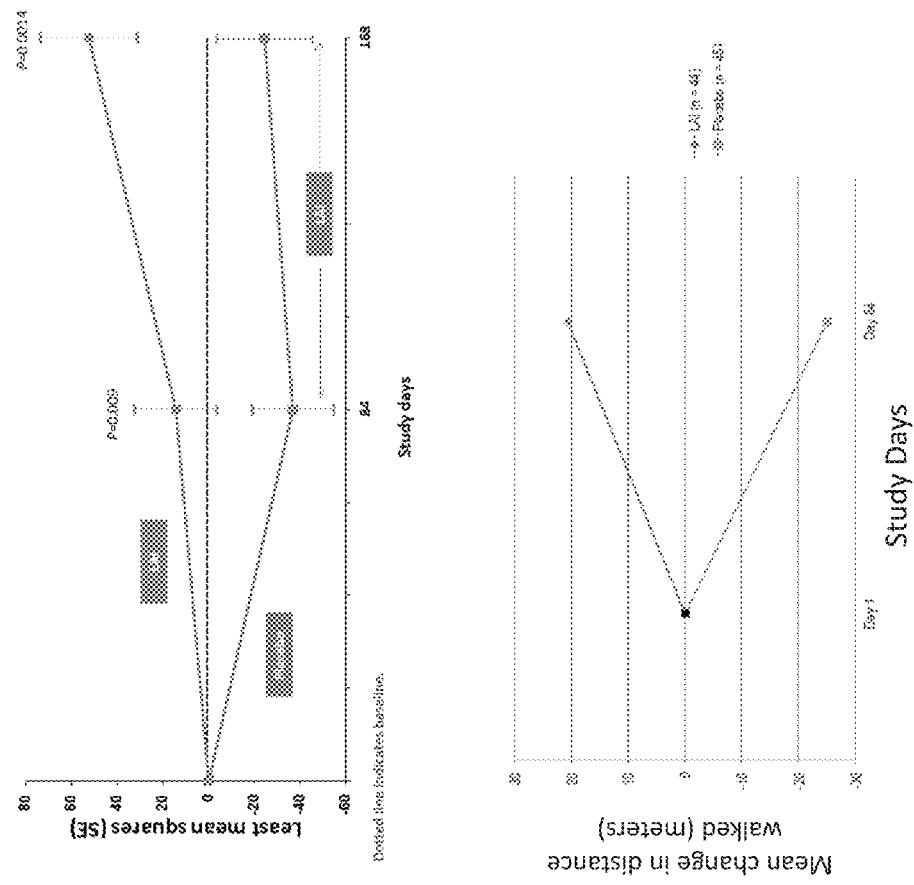
FIG. 7 (top) is a graph showing the change from baseline in the six-minute walk test at day 84 and day 168 (mITT population) and FIG. 7 (bottom) is a graph of the mean change from baseline in distance walked (meters) in the 6MWT in patients receiving LAI vs. placebo at day 84 (last observation carried forward, modified intent to treat population).
Figure 8:
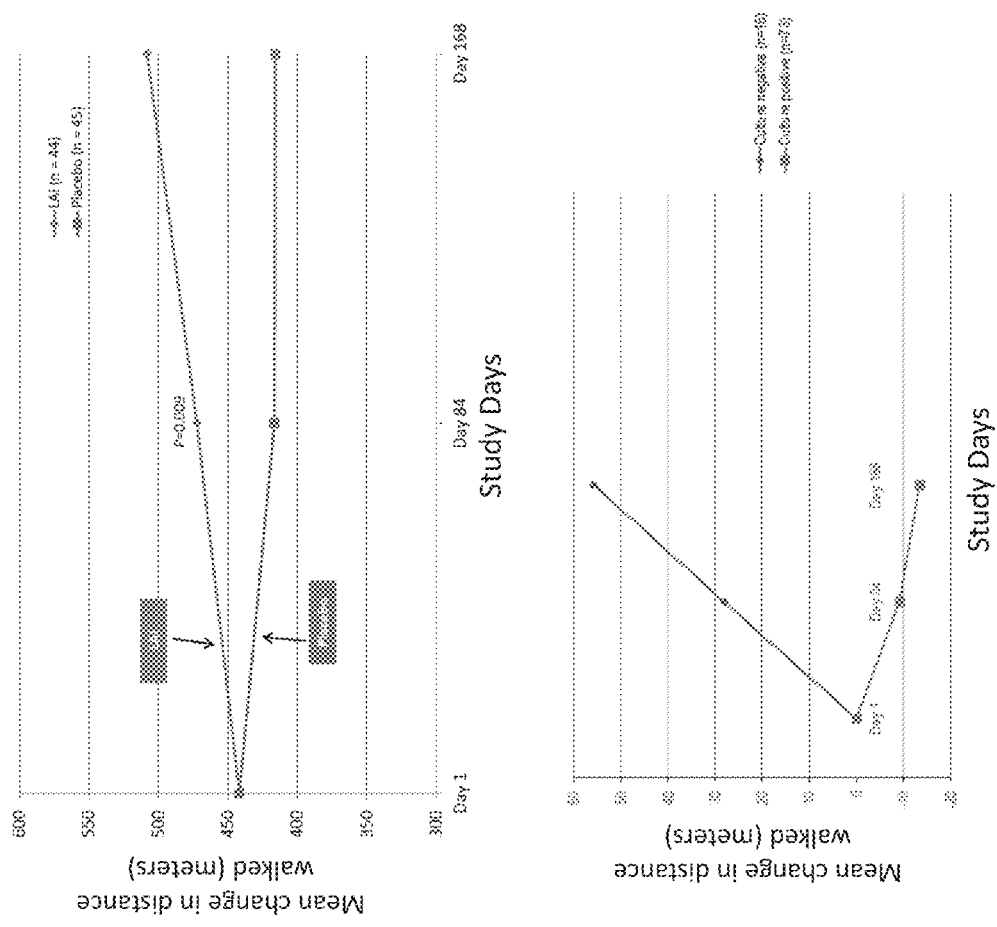
FIG. 8 (top) is a graph showing the average meters walked in the six-minute walk test at day 84 and day 168 (all patients).

The six-minute walk test (6MWT) assessed the impact of LAI on overall physical function or capacity. Results for the 6MWT endpoint (change from baseline from Day 1 to Day 84 at end of double blind study) are provided in FIG. 7 and FIG. 8. LAI demonstrated statistical significance in the 6MWT in the double-blind phase (LAI vs placebo: 23.895 vs-25.032 meters, P=0.009). The mean change from baseline to Day 84 in distance walked (meters) in the 6MWT was significantly higher for patients receiving LAI vs. placebo (20.64 m vs.-25.03 m) (FIG. 7 bottom). In the open-label phase, patients in the LAI arm continued to improve on the 6MWT and patients in the placebo group who started LAI showed a dramatic decline in the rate of deterioration (FIGS. 7 and 8). Further, a significant difference was seen in the mean change from baseline to Day 168 in the 6MWT score for patients with sustained culture-negative status to the end of the open-label phase vs. those without sustained culture-negative status (55.75 m vs.-13.42 m) (FIG. 8 bottom).

Patients with NTM lung infections refractory to treatment showed improvement in distance walked in the 6MWT when LAI was added to their background of guideline-based therapy. Patients with sustained culture-negative status during the study achieved better physical functional capacity as assessed by the 6MWT.

The sample population enrolled in the mITT study exhibited the following, prior to day 168, with regard to culture conversion, measured as three consecutive negative sputum cultures: (1) a total of 16 patients demonstrated culture conversion, all of which were non-cystic fibrosis; (2) 15 patients had MAC and 1 had *M. abscessus*; (3) 8 patients exhibited no treatment success despite greater than 24 months of non-LAI treatment methods, 4 patients exhibited no treatment success despite 12 to 24 months of non-LAI treatment methods, and 4 patients exhibited no treatment success despite 6 to 12 months of non-LAI treatment methods; (4) 7 patients exhibited nodular disease, 2 patients exhibited nodular disease and minimal cavitary lesions, and 7 patients exhibited cavitary lesions; (5) 11 patients started to convert at or prior to day 56 after beginning LAI treatment methods, 2 patients converted at day 84 after beginning LAI treatment methods, and 3 patients converted at day 112 after beginning LAI treatment methods; and (6) 6MWT for converters (n=16) vs. nonconverters (n=43) at day 168 was 89.34 meters (converters) vs. 3.85 meters (nonconverters), with a p-value of 0.0034.

No difference between arms in patients with hemoptysis, tinnitus, and hearing loss was found.

Moreover, it was found that patients entering the open label phase from LAI in the double blind phase (see FIG. 1 for study design) continued to improve. Additionally, patients entering open label phase from placebo demonstrate a dramatic decrease in their rate of decline. Most treatment emergent adverse events (TEAEs) were mild or moderate in severity, and the majority of TEAEs were respiratory in nature (Table 9). Local events and infective exacerbation of the underlying lung disease were the most common TEAEs. Few patients discontinued the study drug due to these events.

TABLE 9

Overview of Adverse Events Through End of Open-label Phase (Safety Population)

| | Double Blind Phase[a] | | Open-Label Phase[b] | |
|---|---|---|---|---|
| | LAI (n = 44) | Placebo (n = 45) | LAI[c] (n = 35) | Placebo[c] (n = 43) |
| Subjects with treatment-emergent adverse events (TEAEs), n(%) TEAEs, n | 41 (93.2) 240 | 40 (88.9) 140 | 31 (88.6) 107 | 42 (97.7) 160 |
| Subjects with TEAEs by maximum severity, n (%) | | | | |
| Grade 1: Mild | 12 (27.3) | 25 (55.6) | 16 (45.7) | 10 (23.3) |
| Grade 2: Moderate | 24 (54.5) | 10 (22.2) | 10 (28.6) | 24 (55.8) |
| Grade 3: Severe | 4 (9.1) | 5 (11.1) | 4 (11.4) | 8 (18.6) |
| Grade 4: Life-threatening or disabling | 0 | 0 | 0 | 0 |
| Grade 5: Death[d] | 1 (2.3) | 0 | 1 (2.9) | 0 |
| Subjects with TEAEs by seriousness, n (%) | | | | |
| Serious | 8 (18.2) | 4 (8.9) | 5 (14.3) | 5 (11.6) |
| Not serious | 33 (75.0) | 36 (80.0) | 26 (74.3) | 37 (86.0) |
| Treatment-emergent serious adverse events, n | 12 | 5 | 10 | 5 |
| Subjects with TEAEs by relationship to study drug, n (%) | | | | |
| Related | 3 (6.8) | 0 | 17 (48.6) | 26 (60.5) |
| Not related | 5 (11.4) | 4 (8.9) | 14 (40.0) | 16 (37.2) |
| Subjects with treatment-emergent audiovestibular adverse events, n (%) | 5 (11.4) | 5 (11.1) | 2 (5.7) | 2 (4.7) |
| Subjects with treatment-emergent renal adverse events, n(%) | 1 (2.3) | 0 | 1 (2.9) | 0 |
| Subjects with adverse events leading to study drug discontinuation, n (%) | 8 (18.2) | 0 | 6 (17.1) | 12 (27.9) |

Figure 9:
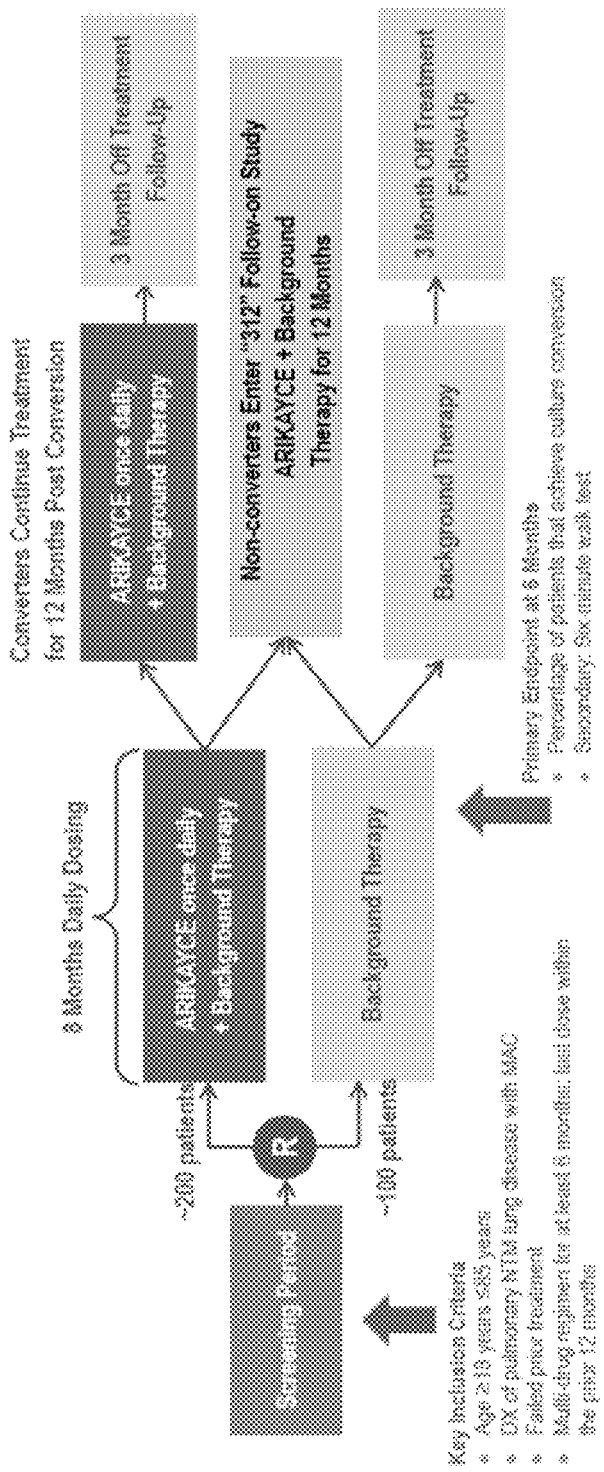
FIG. 9 shows the study design for a randomized, placebo controlled study of liposomal encapsulated amikacin (ARIKAYCE or LAI) in patients with Non-Cystic Fibrosis (Non-CF) *M. avium* complex (MAC) lung infection, described in Example 2.

Example 2: Study of Liposomal Amikacin for Inhalation (LAI) in Patients with Non-CF *M. avium* Complex (MAC) Lung Infection LAI (also referred to herein as "Arikayce™" or "ARIKAYCE™") is a sustained-release lipid composition of amikacin in development for treatment of patients with recalcitrant NTM lung disease. In this study, the efficacy, safety, and tolerability of LAI is assessed in non-Cystic Fibrosis patients having *M. avium* complex (MAC) lung infection. FIG. 9 is a flow chart showing the study design.

The LAI composition has the following components:

| LAI composition | |
|---|---|
| Amikacin Sulfate | ~70 mg/mL |
| DPPC | ~30-35 mg/mL |
| Cholesterol | ~15-17 mg/mL |
| NaCl | ~1.5% |

Table 10 provides the inclusion criteria for the study.

TABLE 10

| Inclusion Criteria for Study |
|---|
| Age ≥18 years ≤85 years |
| Diagnosis of pulmonary NTM MAC lung disease |
| Failed prior treatment |
| Multi-drug regimen for at least 6 months; last dose within the prior 12 months |

Patients are randomized 2:1 into two groups: (i) 590 mg LAI+background therapy and (ii) background therapy only). Each patient group is subjected to daily dosing for 8 months. Primary culture conversion is assessed at 6 months. 6MWT is also carried out for each patient at 6 months.

Culture converters continue treatment for 12 months post conversion.

All, documents, patents, patent applications, publications, product descriptions, and protocols which are cited throughout this application are incorporated herein by reference in their entireties for all purposes.

The embodiments illustrated and discussed in this specification are intended only to teach those skilled in the art the best way known to the inventors to make and use the invention. Modifications and variation of the above-described embodiments of the invention are possible without departing from the invention, as appreciated by those skilled in the art in light of the above teachings. It is therefore understood that, within the scope of the claims and their equivalents, the invention may be practiced otherwise than as specifically described. Accordingly, the foregoing descriptions and drawings are by way of example only and the disclosure is described in detail by the claims that follow.

The invention claimed is:

1. A method for treating a non-cystic fibrosis (CF) *Mycobacterium avium* complex (MAC) lung infection in a patient in need thereof, comprising:
    administering to the lungs of the patient a pharmaceutical composition comprising amikacin, or a pharmaceutically acceptable salt thereof, encapsulated in a plurality of liposomes, wherein the lipid component of the plurality of liposomes consists of an electrically neutral phospholipid and cholesterol,
    wherein administering to the lungs of the patient comprises aerosolizing the pharmaceutical composition to provide an aerosolized pharmaceutical composition comprising a mixture of free amikacin, or a pharmaceutically acceptable salt thereof, and liposomal complexed amikacin, or a pharmaceutically acceptable salt thereof, and administering the aerosolized pharmaceutical composition via a nebulizer to the lungs of the patient once daily in a single dosing session, for an administration period of at least 84 days,
    and wherein the treating comprises achieving a negative MAC sputum culture in the patient.

2. The method of claim 1, wherein the amikacin or pharmaceutically acceptable salt thereof is amikacin sulfate.

3. The method of claim 1, wherein the plurality of liposomes comprises unilamellar vesicles, multilamellar vesicles, or a mixture thereof.

4. The method of claim 1, wherein the electrically neutral phospholipid is an electrically neutral phosphatidylcholine.

5. The method of claim 4, wherein the electrically neutral phosphatidylcholine is dipalmitoylphosphatidylcholine (DPPC).

6. The method of claim 1, wherein the electrically neutral phospholipid comprises DPPC, and the plurality of liposomes comprise unilamellar vesicles, multilamellar vesicles, or a mixture thereof.

7. The method of claim 6, wherein the volume of the pharmaceutical composition is from about 8 mL to about 10 mL.

8. The method of claim 6, wherein the pharmaceutical composition comprises from about 500 mg to about 650 mg amikacin, or pharmaceutically acceptable salt thereof.

9. The method of claim 6, wherein the pharmaceutical composition is an aqueous dispersion.

10. The method claim 7, wherein the volume of the pharmaceutical composition is about 8 mL.

11. The method of claim 1, wherein during the single dosing session, the aerosolized pharmaceutical composition is administered in less than about 15 minutes.

12. The method of claim 1, wherein during the single dosing session, the aerosolized pharmaceutical composition is administered in about 10 minutes to about 14 minutes.

13. The method of claim 6, wherein about 25% to about 35% of the aerosolized pharmaceutical composition is deposited in the bronchial and alveolar regions of the patient's lungs.

14. The method of claim 6, wherein the patient in need of treatment has bronchiectasis.

15. The method of claim 6, wherein the patient in need of treatment was previously unresponsive to *Mycobacterium avium* complex (MAC) therapy.

16. The method of claim 6, wherein the patient experiences an improvement in forced expiratory volume in one second ($FEV_1$) for at least 15 days after the administration period ends, as compared to the $FEV_1$ of the patient prior to the administration period.

17. The method of claim 6, wherein the patient experiences an improvement in blood oxygen saturation for at least 15 days after the administration period ends, as compared to the blood oxygen saturation of the patient prior to the administration period.

18. The method of claim 16, wherein the patient's $FEV_1$ is increased at least 5% over the $FEV_1$ of the patient prior to the administration period.

19. The method of claim 16, wherein the patient's $FEV_1$ is increased at least 10% over the $FEV_1$ of the patient prior to the administration period.

20. The method of claim 16, wherein the patient's $FEV_1$ is increased at least 15% over the $FEV_1$ of the patient prior to the administration period.

21. The method of claim 16, wherein the patient's $FEV_1$ is increased by 5% to 50% over the $FEV_1$ prior to the administration period.

22. The method of claim 6, wherein the patient exhibits an increased number of meters walked in the 6 minute walk test (6MWT), as compared to the number of meters walked by the patient prior to undergoing the treatment method.

23. The method of claim 22, wherein the increased number of meters walked in the 6MWT is at least about 5 meters.

24. The method of claim 22, wherein the increased number of meters walked in the 6MWT is from about 5 meters to about 50 meters.

25. The method of claim 22, wherein the increased number of meters walked in the 6MWT is from about 15 meters to about 50 meters.

26. The method of claim 8, wherein the pharmaceutical composition comprises from about 550 mg to about 625 mg amikacin, or pharmaceutically acceptable salt thereof.

27. The method of claim 8, wherein the pharmaceutical composition comprises from about 550 mg to about 600 mg amikacin, or pharmaceutically acceptable salt thereof.

28. The method of claim 1, wherein achieving a negative MAC sputum culture in the patient comprises achieving at least three consecutive negative MAC sputum cultures.

29. The method of claim 1, wherein the administration period is at least about 6 months.

30. The method of claim 28, wherein the administration period is at least about 6 months.

* * * * *